(12) United States Patent
Felsenfeld et al.

(10) Patent No.: US 7,737,250 B2
(45) Date of Patent: Jun. 15, 2010

(54) PEPTIDES FOR TREATING AXONAL DAMAGE, INHIBITION OF NEUROTRANSMITTER RELEASE AND PAIN TRANSMISSION, AND BLOCKING CALCIUM INFLUX IN NEURONS

(75) Inventors: Dan P. Felsenfeld, New York, NY (US); Maria A. Diverse-Pierluissi, New York, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 681 days.

(21) Appl. No.: 10/561,015

(22) PCT Filed: Jun. 21, 2004

(86) PCT No.: PCT/US2004/019934

§ 371 (c)(1),
(2), (4) Date: Feb. 17, 2006

(87) PCT Pub. No.: WO2004/112728

PCT Pub. Date: Dec. 29, 2004

(65) Prior Publication Data

US 2006/0142189 A1    Jun. 29, 2006

Related U.S. Application Data

(60) Provisional application No. 60/480,092, filed on Jun. 19, 2003, provisional application No. 60/544,798, filed on Feb. 13, 2004.

(51) Int. Cl.
| | |
|---|---|
| *C07K 7/00* | (2006.01) |
| *C07K 14/00* | (2006.01) |
| *G01N 33/53* | (2006.01) |
| *G01N 33/567* | (2006.01) |
| *A61K 49/00* | (2006.01) |
| *C12N 5/06* | (2006.01) |
| *C12N 5/08* | (2006.01) |
| *C12N 5/00* | (2006.01) |
| *A01N 1/00* | (2006.01) |

(52) U.S. Cl. .................. 530/300; 435/7.21; 435/326; 435/366; 435/1.1; 424/9.1; 530/350

(58) Field of Classification Search ................. None
See application file for complete search history.

(56) References Cited

U.S. PATENT DOCUMENTS

| | | | |
|---|---|---|---|
| 5,840,689 A | 11/1998 | Daniloff | |
| 5,872,225 A | 2/1999 | Lemmon | |
| 6,025,140 A * | 2/2000 | Langel et al. | 435/6 |
| 6,313,265 B1 | 11/2001 | Phillips | |
| 6,432,404 B1 | 8/2002 | Gallatin | |
| 6,576,607 B1 * | 6/2003 | Schachner | 514/2 |

FOREIGN PATENT DOCUMENTS

WO    WO-00/29427    5/2000

OTHER PUBLICATIONS

Davis et al. J. Cell Biol. 1996, 135:1355-1367.*
Schmidt et al. Annu. Rev. Biomed. Eng. 2003. 5: 293-347.*
Hoke et al. Nat. Clin. Pract. Neurol. 2006: 448-454.*
't Hart et al. Curr. Opin. Neurol. 2003. 16: 375-383.*
Davis and Bennett J Biol Chem 1994;269:27163-27166.
De Angelis et al., J Biol Chem 2001;276:32738-32742.
Delcour, Ah, and Tsien RW. 1993. Science Feb. 12, 259 (5097): 980-84.
Derossi d. et al., Trends Cell Biol 1998;8:84-87.
Dickson et al. J Cell Biol 2002;157:1105-1112.
Dunlap K, et al. J Physiol. 1981, 317:519-535.
Gil OD et al., J. Cell. Biol Aug. 18, 2003, 162 (4) 719-30.
Herlitze S, et al. Nature. Mar. 21, 1996; 380(6571) 259-62.
Hille B. Trends Neurosci. Dec. 1994; 17(12):531-6.
Hortsch et al. Cell Adhes Commun 1998;5:61-73.
Hortsch M. et al., Molecular and Cellular Neuroscience 15, 1-10 (2000).
Ikeda SR. Nature. Mar. 21, 1996;380(6571):255-8.
Jenkins SM and Bennett V. (2001). J. Cell Biol. 155:739-45.
Kamiguchi and Yoshihara J. Neurosci 2001;21:9194-9203.
Kamiguchi and Lemmon J Neurosci 1998;18:3749-3756.
Kizhatil et al. J Neurosci 2002;22:7945-7958.
Mattson MP, et al., Neuromolecular Med. 2003;3(2): 65-94.
Maximov A., Bezprozvanny I. J Neurosci. 22:6939-52.
Miura et al. FEBS Lett 1991;289:91-95.
Mody I, et al., Trends Pharmacol Sci. Oct. 1995; 16(10): 356-9.
Needham et al. J Neurosci 2001;21:1490-1500.
Schaefer et al. J Cell Biol 2002;157:1223-1232.
Tuvia et al. J Cell Biol 1999;147:995-1007.
Zheng Z. et al., Curr Mol Med. Jun. 2003;3(4):361-72.
Zisch et al. J Neurosci Res 1997;47:655-65.
Kamiguchi et al. J Neurosci 1998;18;5311-21.
T. Garver et al., "Tyrosine Phosphorylation at a Site Highly Conserved in the L1 family of Cell Adhesion Molecules Abolishes Ankyrin..." The Journal of Cell Biology vol. 137, No. 3, May 5, 1997 pp. 703-714.

(Continued)

*Primary Examiner*—Christine J Saoud
*Assistant Examiner*—Chang-Yu Wang
(74) *Attorney, Agent, or Firm*—Fish & Richardson P.C.

(57) ABSTRACT

The present invention pertains to methods to promote outgrowth of, or extension across a substrate of, neuronal cells by inhibiting the interaction between the cytoplasmic tail of the L1-CAM cell surface adhesion molecule and the cytoskeletal protein ankyrin. The invention also pertains to a method to treat diseases characterized by axonal damage such as spinal cord injury, traumatic brain injury, stroke, and neurodegenerative disease by administration of novel peptides that inhibit the binding of the L1-CAM cytoplasmic tail to ankyrin, and to pharmaceutical compositions comprising such peptides. The invention further pertains to a method of blocking calcium flux to protect against neural cell death following stroke or traumatic head injury.

7 Claims, 20 Drawing Sheets

OTHER PUBLICATIONS

S. Tuvia et al., "The Phosphorylation State of the FIGQY Tyrosine of Neurofascin Determines . . ." Proc Natl. Acad. Sci. vol. 94 pp. 12957-12962, Nov. 1997.

X. Zhang et al., "Structural Requirements for Association of Neurofascin with Ankyrin" Journal of Biological Chemistry vol. 273, No. 46 Nov. 13 pp. 30785-30794.

Pollerberg GE et al., "Lateral Mobility of the Cell Adhesion Molecule L1 Within the Surface Membrane of Morphologically Undifferentiated and Differentiated Neuroblastoma Cells" Natl. Library of Medicine Eur J Neurosci 1990;2(8):712-717.

* cited by examiner

```
1    GCTAGCTATG GTCGTGATGC TGCGGTACGT GTGGCCTCTC CTCCTCTGCA GCCCTGCCT
61   GCTCATACAG ATTCCTGATG AATATAAAGG ACACCATGTA CTAGAGCCAC CTGTCATCAC
121  GGAACAGTCT CCACGGCGCC TGGTTGTCTT CCCAACAGAT GACATAAGCC TCAAATGTGA
181  AGCCAGAGGC AGACCCCAAG TGGAGTTCCG CTGGACGAAA GATGGCATCC ACTTCAAACC
241  TAAGGAAGAA TTGGGTGTAG TGGTACACGA GGCACCCTAT TCTGGCTCCT TCACCATCGA
301  AGGCAACAAC AGCTTTGCCC AGAGGTTTCA GGGCATCTAT CGCTGCTATG CCAGCAATAA
361  TCTAGGAACT GCCATGTCGC ATGAGATCCA GCTCGTGGCT GAGGGTGCCC CCAAATGGCC
421  GAAGGAGACT GTAAAACCCG TGGAAGTGGA GGAAGGAGAA TCAGTAGTTC TACCTTGCAA
481  TCCTCCACCC AGTGCAGCCC CACTTAGGAT CTACTGGATG AACAGCAAGA TTTTGCACAT
541  CAAACAAGAT GAGCGGGTGT CCATGGGCCA GAATGGAGAC CTATATTTTG CCAATGTGCT
601  TACCTCAGAC AATCATTCAG ACTACATCTG CAATGCCCAC TTCCCTGGCA CCCGGACCAT
661  CATTCAAAAG GAACCTATTG ACCTCCGGGT CAAGCCCACC AACAGCATGA TTGACCGGAA
721  GCCACGCCTG CTCTTCCCCA CAAACTCCAG CAGTCACCTC GTGGCCTTGC AGGGCCAGTC
781  ATTAATCCTG GAGTGCATTG CTGAGGGATT CCCTACACCC ACCATCAAGT GGCTGCACCC
841  CAGTGACCCT ATGCCAACAG ACCGTGTTAT CTACCAGAAC CATAACAAGA CACTGCAGCT
901  CCTCAATGTG GGCGAGGAAG ATGATGGCGA GTATACCTGC CTTGCTGAGA ACTCACTGGG
961  CAGTGCTCGG CATGCCTACT ATGTCACTGT GGAAGCTGCC CCATACTGGC TGCAGAAGCC
1021 CCAGAGTCAT TTGTATGGGC AGGAGAGAC TGCCCGCCTA GACTGCCAAG TCCAGGGCAG
1081 GCCCCAACCA GAGGTCACTT GGAGAATCAA CGGAATGTCT ATAGAGAAGG TGAACAAGGA
1141 CCAGAAGTAC CGGATTGAGC AGGGGTCTTT GATCCTGAGT AATGTGCAAC AAGTGACAC
1201 AATGGTGACC CAGTGTGAAG CTCGCAACCA GCATGGGCTC CTACTAGCCA ATGCCTATAT
1261 CTATGTTGTC CAGCTGCCAG CCAGGATCCT AACAAAAGAC AATCAGACAT ACATGGCAGT
1321 AGAGGGCAGT ACTGCTTACT TGCTGTGCAA AGCCTTTGGA GCTCCTGTTC CAGTGTCCA
1381 GTGGCTGGAT GAGGAAGGAA CCACAGTGCT TCAGGATGAA AGATTTTCC CCTATGCCAA
1441 TGGAACGCTG GGCATCAGAG ATCTCCAGGC CAATGACACT GGACGCTATT TCTGCCAGGC
1501 TGCCAATGAC CAGAACAATG TGACCATTTT GGCTAACCTA CAGGTTAAAG AAGCAACCCA
1561 GATCACACAA GGACCCCGGA GCACAATTGA GAAGAAAGGT GCAAGGGTGA CATTCACGTG
1621 CCAGGCCTCC TTTGACCCCT CTTTACAAGC CAGCATCACT TGGCGTGGAG ATGGGAGAGA
1681 CCTCCAGGAA CGTGGAGACA GTGACAAGTA TTTCATAGAA GATGGGCAAC TTGTCATCCA
1741 GAGCCTGGAC TACAGTGACC AGGGCAACTA CAGTTGTGTG GCCAGCACTG AACTGGATGA
1801 GGTGGAGAGC AGGGCACAAC TCTTAGTGGT GGGAAGCCCT GGGCCAGTGC CTCACCTGGA
1861 GCTGTCCGAC CGCCACTTGC TGAAGCAGAG CCAGGTGCAC TTGTCTTGGA GCCCTGCTGA
1921 AGACCACAAC TCTCCCATTG AGAAATATGA CATTGAATTT GAGGACAAGG AAATGGCTCC
1981 TGAGAAATGG TTCAGTCTAG GCAAGGTGCC AGGAAATCAG ACCTCTACTA CCCTCAAGCT
2041 GTCCCCCTAT GTCCACTATA CCTTTCGGGT CACTGCCATT AACAAATATG GTCCCGGAGA
2101 ACCCAGCCCT GTCTCTGAGA CTGTAGTCAC ACCTGAGGCA GCCCCAGAGA GAACCCTGT
2161 GGATGTGAGA GGGGAAGGAA ATGAGACCAA CAATATGGTC ATCACATGGA AGCCCCTTCG
2221 GTGGATGGAT TGGAATGCCC CCCAGATTCA GTACCGTGTA CAGTGGCGAC CACTGGGCAA
2281 ACAAGAGACC TGGAAGGAAC AGACCGTGAG CGACCCCTTC CTGGTGGTGT CTAACACTTC
2341 CACATTTGTG CCTTATGAGA TCAAAGTCCA GGCAGTGAAC AACCAGGGA AGGGCCCTGA
2401 GCCCAGGTC ACCATTGGCT ATTCAGGGGA AGACTACCCC CAGGTGAGCC CTGAGCTTGA
2461 AGACATCACA ATCTTCAACT CAAGCACTGT GCTGGTCAGG TGGAGGCCTG TGGACTTGGC
2521 CCAGGTTAAG GGCCACCTCA GGGGATACAA TGTAACGTAC TGGTGGAAGG GCAGTCAGAG
2581 AAAGCACAGC AAGAGGCATG TCCACAAAAG TCACATGGTG GTACCTGCGA ACACCACCAG
2641 TGCCATCCTC AGTGGTTTGC GTCCTTACAG CTCTTATCAT GTGGAGGTAC AGGCCTTTAA
2701 TGGGCGGGGC TTAGGGCCTG CAAGTGAATG GACCTTCAGC ACCCCAGAGG GAGTGCCTGG
```

FIGURE 7A

```
2761 CCACCCTGAG GCATTACATC TGGAGTGCCA GTCGGACACT AGCCTGCTAC TGCACTGGCA
2821 GCCACCACTC AGCCACAATG GAGTGCTCAC TGGCTACCTG CTCTCTTACC ATCCCTTGGA
2881 TGGGGAAAGC AAAGAGCAGT TGTTCTTCAA CCTTTCGGAC CCAGAGCTCC GGACTCATAA
2941 TCTCACCAAC CTCAACCCTG ATCTACAGTA CCGCTTCCAG CTTCAGGCCA CCACCCAACA
3001 GGGTCCTGGT GAGGCCATTG TGCGTGAAGG AGGCACTATG GCCCTATTTG GCAAGCCAGA
3061 TTTTGGCAAC ATTTCAGTCA CAGCAGGTGA AAACTACAGT GTGGTCTCCT GGGTCCCTCG
3121 GGAGGGCCAG TGCAATTTCA GGTTCCACAT CCTGTTCAAA GCCTTGCCAG AAGGGAAAGT
3181 GAGCCCTGAT CACCAGCCTC AGCCTCAATA TGTGAGCTAC AATCAGAGCT CCTACACACA
3241 GTGGGACCTA CAGCCTGACA CCAAATATGA GATCCACCTG ATGAGGGAGA AGGTCCTCTT
3301 GCACCATCTG GCTGTGAAGA CTAATGGCAC TGGCCCCGTG CGAGTGTCGA CTACCGGTAG
3361 CTTTGCCTCC GAGGGCTGGT TCATCGCCTT TGTCAGTGCT ATCATTCTCT TGCTCCTCAT
3421 CCTGCTCATC CTCTGCTTCA TCAAACGCAG CAAGGGCGGC AAATATTCAG TGAAGGACAA
3481 GGAGGACACT CAGGTAGATT CCGAGGCCCG GCCCATGAAA GACGAGACCT TCGGCGAGTA
3541 CAGGTCCCTG GAGAGTGACA ATGAAGAGAA GGCCTTCGGC AGCAGCCAGC CATCTCTCAA
3601 TGGAGACATC AAACCCCTAG GCAGTGATGA CAGTCTGGCT GATTATGGGG GCAGTGTGGA
3661 TGTCCAGTTC AATGAGGATG CTCTTTCAT CGGCCAATAC AGTGGCAAAA AAGAGAAGGA
3721 GGCAGCGGGA GGCAATGACA GCTCAGGGGC TACCTCTCCT ATCAATCCTG CAGTAGCCCT
3781 AGAA*TAG*CAA G̲C̲T̲C̲G̲A̲G̲
```

FIGURE 7B

| | | | | |
|---|---|---|---|---|
| 1 | MVVMLRYVWP | LLLCSPCLLI | QIPDEYKGHH | VLEPPVITEQ | SPRRLVVFPT |
| 51 | DDISLKCEAR | GRPQVEFRWT | KDGIHFKPKE | ELGVVVHEAP | YSGSFTIEGN |
| 101 | NSFAQRFQGI | YRCYASNNLG | TAMSHEIQLV | AEGAPKWPKE | TVKPVEVEEG |
| 151 | ESVVLPCNPP | PSAAPLRIYW | MNSKILHIKQ | DERVSMGQNG | DLYFANVLTS |
| 201 | DNHSDYICNA | HFPGTRTIIQ | KEPIDLRVKP | TNSMIDRKPR | LLFPTNSSSH |
| 251 | LVALQGQSLI | LECIAEGFPT | PTIKWLHPSD | PMPTDRVIYQ | NHNKTLQLLN |
| 301 | VGEEDDGEYT | CLAENSLGSA | RHAYYVTVEA | APYWLQKPQS | HLYGPGETAR |
| 351 | LDCQVQGRPQ | PEVTWRINGM | SIEKVNKDQK | YRIEQGSLIL | SNVQPSDTMV |
| 401 | TQCEARNQHG | LLLANAYIYV | VQLPARILTK | DNQTYMAVEG | STAYLLCKAF |
| 451 | GAPVPSVQWL | DEEGTTVLQD | ERFFPYANGT | LGIRDLQAND | TGRYFCQAAN |
| 501 | DQNNVTILAN | LQVKEATQIT | QGPRSTIEKK | GARVTFTCQA | SFDPSLQASI |
| 551 | TWRGDGRDLQ | ERGDSDKYFI | EDGQLVIQSL | DYSDQGNYSC | VASTELDEVE |
| 601 | SRAQLLVVGS | PGPVPHLELS | DRHLLKQSQV | HLSWSPAEDH | NSPIEKYDIE |
| 651 | FEDKEMAPEK | WFSLGKVPGN | QTSTTLKLSP | YVHYTFRVTA | INKYGPGEPS |
| 701 | PVSETVVTPE | AAPEKNPVDV | RGEGNETNNM | VITWKPLRWM | DWNAPQIQYR |
| 751 | VQWRPLGKQE | TWKEQTVSDP | FLVVSNTSTF | VPYEIKVQAV | NNQGKGPEPQ |
| 801 | VTIGYSGEDY | PQVSPELEDI | TIFNSSTVLV | RWRPVDLAQV | KGHLRGYNVT |
| 851 | YWWKGSQRKH | SKRHVHKSHM | VVPANTTSAI | LSGLRPYSSY | HVEVQAFNGR |
| 901 | GLGPASEWTF | STPEGVPGHP | EALHLECQSD | TSLLLHWQPP | LSHNGVLTGY |
| 951 | LLSYHPLDGE | SKEQLFFNLS | DPELRTHNLT | NLNPDLQYRF | QLQATTQQGP |

FIGURE 8A

```
1001    GEAIVREGGT  MALFGKPDFG  NISVTAGENY  SVVSWVPREG  QCNFRFHILF

1051    KALPEGKVSP  DHQPQPQYVS  YNQSSYTQWD  LQPDTKYEIH  LMREKVLLHH

1101    LAVKTNGTGP  VRVSTTGSFA  SEGWFIAFVS  AIILLLLILL  ILCFIKRSKG

1151    GKYSVKDKED  TQVDSEARPM  KDETFGEYRS  LESDNEEKAF  GSSQPSLNGD

1201    IKPLGSDDSL  ADYGGSVDVQ  FNEDGSFIGQ  YSGKKEKEAA  GGNDSSGATS

1251    PINPAVALE
```

FIGURE 8B

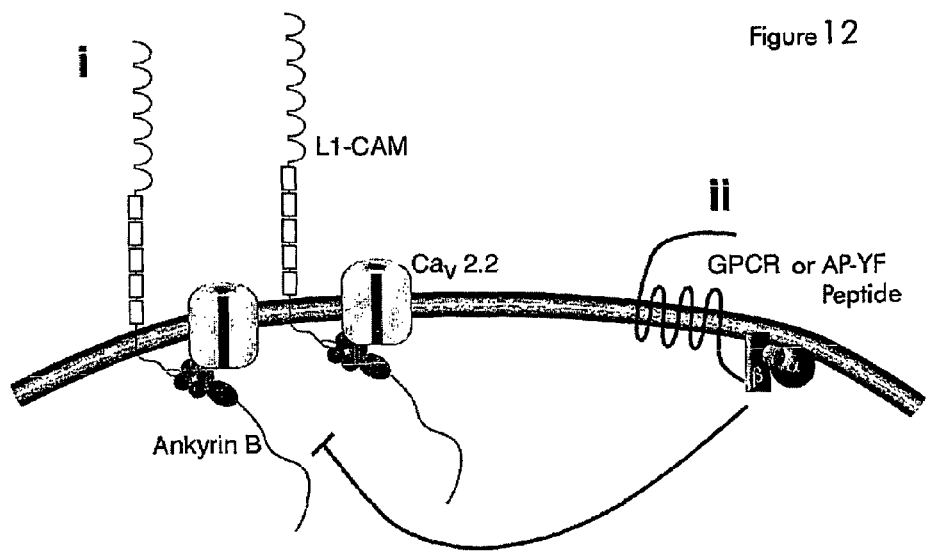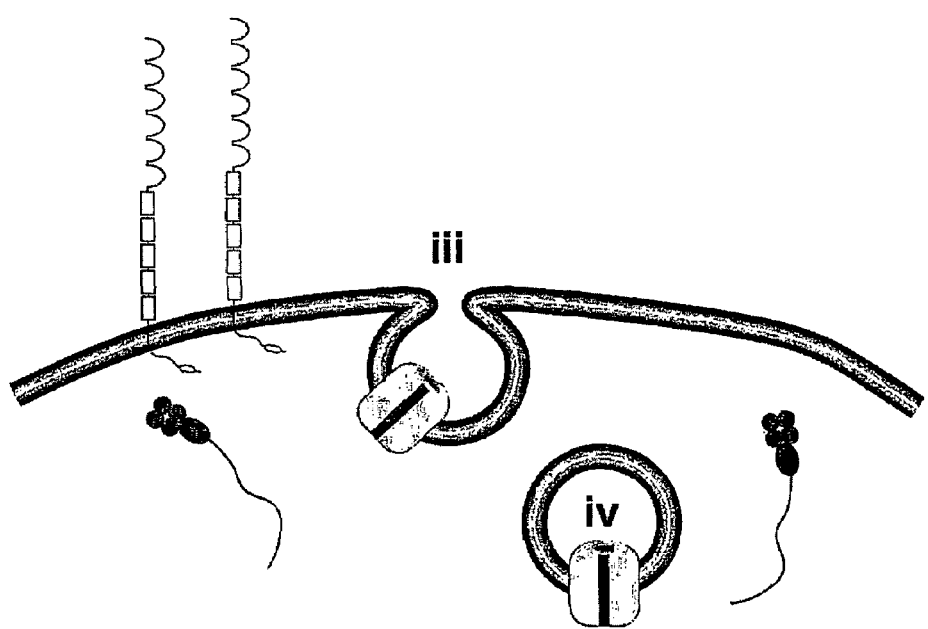
Figure 12

US 7,737,250 B2

PEPTIDES FOR TREATING AXONAL DAMAGE, INHIBITION OF NEUROTRANSMITTER RELEASE AND PAIN TRANSMISSION, AND BLOCKING CALCIUM INFLUX IN NEURONS

CROSS REFERENCE TO PRIOR APPLICATION

This is a U.S. National Phase application under 35 U.S.C. §371 of International Patent Application No. PCT/US2004/019934, filed Jun. 21, 2004, which claims priority to U.S. Provisional Patent Application Ser. No. 60/480,092, filed on Jun. 19, 2003 and U.S. Provisional Patent Application Ser. No. 60/544,798, filed on Feb. 13, 2004. The International Application was published on Dec. 29, 2004 as WO 2004/112728 A2 under PCT Article 21(2).

This application claims priority under 35 U.S.C. §119(e) to U.S. Provisional Applications Ser. Nos. 60/480,092 filed Jun. 19, 2003, and 60/544,798 filed Feb. 13, 2004 which are incorporated by reference herein in their entirety.

The research leading to this invention was supported, in part, by Grant No. GM63192-01 and Grant No. N537443 awarded by the National Institutes of Health. Accordingly, the United States government may have certain rights to this invention.

FIELD OF THE INVENTION

The present invention pertains to methods to promote outgrowth of, or extension across a substrate of neuronal cells. The invention also pertains to methods to block calcium signaling through neurons.

BACKGROUND OF THE INVENTION

The adhesion and migration of adherent cells depends on the function of cell-surface glycoproteins that mediate the adhesive contact between the cell surface and molecules in the cellular microenvironment. In quiescent, non-migratory cells, adhesion receptors are responsible for maintaining stable contact between the cell and its environment. As cells translocate, adhesion proteins transduce traction forces from the cytoskeleton across the cytoplasmic membrane to the substrate, permitting cells to pull against their environment. Thus, receptor-mediated traction-force generation depends on connections between adhesion receptors and the cytoskeleton. In addition, receptor-cytoskeleton interactions play a crucial role in the stabilization of adhesive complexes thus modulating binding avidity.

The establishment and maintenance of neuronal connections are essential features of nervous system function. The activity of adhesion proteins on the cell surface is essential to both of these processes. During development, the translocation of the neuronal growth cone depends critically on adhesion proteins that mediate the recognition of molecules in the extracellular environment (Tessier-Lavigne and Goodman. Science 1986;274:1123-1133). In the adult, many of the same adhesion proteins help maintain axon fascicles and synaptic contacts. Whereas receptors involved in adhesive contacts mediate largely static connections between adjacent cells, adhesion receptors in migrating cells serve to elaborate cellular traction forces between the cell and its environment (Harris et al. Science 1980;208: 177-179 and Galbraith and Sheetz J. Cell Biol 1999; 147:1313-1324). A variety of adhesion receptor families have been shown to serve as receptors for permissive, substrate-bound molecules that promote axon outgrowth, including integrins, Ig-CAM's and cadherins (Kamiguchi and Yoshihara J. Neurosci 2001;21:91941-9203). This common activity raises the possibility of a common traction-based mechanism for transducing permissive cues. However, while the biophysical basis of integrin-mediated traction-force generation and adhesion is fairly well characterized (Felsenfeld et al. Nature 1996;383:438-440; Choquet et al. Cell 1997;88:39-48; Galbraith and Sheetz. Proc Natl Acad Sci USA 1997;94:9114-9118; and Yauch et al. J Exp Med 1997;186:1347-1355), little is known about the differential regulation of adhesion and migration in other families of adhesion receptors.

Immunoglobulin-family cell adhesion molecules (Ig-CAMs) have been implicated in the guided growth of neuronal processes during development (Kamiguchi and Lemmon. Curr Opin Cell Biol 2000; 12:598-605 and Rutishauser J Cell Biol 2000; 149:757-760). In the vertebrate central nervous system, L1-CAM, an Ig-CAM, plays an essential role in the growth and guidance of axons towards their targets (Daline et al. Nat Genet 1997;17:346-349 and Cohen et al. Curr Biol 1998;8:26-33). L1-CAM mutations in humans lead to a variety of developmental defects including corpus callosum hyperplasia, mental retardation, adducted thumbs, spastic paraplegia and hydrocephalus (CRASH syndrome), suggesting that L1-CAM plays a crucial role in the development of the central nervous system (Fransen et al. Eur J Hum Genet 1995;3:273-284). Moreover, the capacity of substrate-immobilized L1-CAM-ligands to promote neurite extension in vitro through interactions with cell-surface L1-CAM (Lemmon et al. Neuron 1989;2:1597-1603; Kuhn et al. J Cell Biol 1991;115:1113-1126; and Felsenfeld et al. Neuron 1994; 12:675-690) raises the possibility that L1-CAM on the growth cone may mediate the generation of traction forces in a mechanism similar to that observed for integrins in other cell types. In addition, L1-CAM may play other roles in the development and maintenance of the nervous system, including the stabilization of axon fascicles in the mature animal (Dahme et al. Nat Genet 1997;17:346-349). To accomplish each of these diverse functions, the movement of L1-CAM in the plane of the membrane must be regulated across the cell surface.

The regulation of adhesion receptor distribution, movement, and function in adhesion and migration depends on the connection between these glycoproteins and components of the cytoskeleton. L1-CAM interacts with as many as four cytosolic binding partners through two discrete sites in the cytoplasmic tail (Kamiguchi et al. J Neurosci 1998; 18:5311-5321; Zhang et al. J Biol Chem 1998;273:30785-30794; Dickson et al. J Cell Biol 2002;157:1105-1112; and Kizhatil et al. J Neurosci 2002;22:7945-7958). The binding of L1-CAMs to members of the ankyrin family of cytoskeletal adaptor proteins is perhaps the best characterized of these interactions (Davis and Bennett J Biol Chem 1994;269: 27163-27166; Garver et al. J Cell Biol 1997;137:703-714; and Hortsch et al. Cell Adhes Commun 1998;5:61-73). In vertebrates, three distinct genes encoding ankyrin family members, ankyrinB, ankyrinG and ankyrinR, have been identified with distinct but overlapping expression patterns (Bennett and Baines Physiol Rev 2001;81:1353-1392). In the nervous system and heart, ankyrins appear to play a crucial role in the organization of cellular structures involved in signaling (Lambert et al. J Neurosci 1997; 17:7025-7036 and Tuvia et al. J Cell Biol 1999; 147:995-1008). The L1-CAM family member neurofascin binds to ankyrin through a motif that is highly conserved among L1-CAM-family members near the carboxy-terminus of the cytoplasmic tail (Garver et al. J Cell Biol 1997; 137:703-714). The ankyrin binding site, mapped based on the interaction between neurofascin and ankyrinG, is comprised of a 12 amino acid motif, QFNEDGSFIGQY (SEQ ID NO: 1), which includes a carboxy-terminal tyrosine and is identical in neurofascin and L1-CAM from rat (Miura et al. FEBS Lett 1991;289:91-95 and Zhang et al. J Biol Chem 1998;273:30785-20794). Ankyrin binds to this motif in its dephosphorylated state (Garver et al., supra). In addition, when phosphorylated, this site serves as a binding partner for the protein doublecortin (Kizhatil et al., supra), a protein which has been implicated in the migration of neuronal progenitors to their proper lamina in the mature cerebral cortex (Francis et al. Neuron 1999;23:247-256 and Gleeson et al. Neuron 1999;23:257-271). Mutations at this site in human L1-CAM lead to a similar disruption in ankyrin binding (Needham et al. J Neurosci 2001;21:1490-1500). However, the drosophila L1-CAM homolog neuroglian, while requiring the FIGQY (SEQ ID NO: 8) motif for ankyrin recruitment, appears to be regulated primarily through ligation of the extracellular domain (Hortsch et al., supra). At a functional level, the binding of ankyrin to L1-CAMs like neurofascin plays a critical role in L1-CAM-mediated cell adhesion (Tuvia et al. Proc Natl Acad Sci USA 1997;94:12957-12962).

In addition to ankyrin binding, a distinct phosphorylation site (YRSLE; SEQ ID NO: 7) upstream of the ankyrin site binds both the μ2 chain of the AP-2 clathrin complex (Kamiguchi and Lemmon J Neurosci 1998;18:3749-3756 and Schaefer et al. J Cell Biol 2002; 157: 1223-1232) and ERM proteins (Dickson et al. J Cell Biol 2002; 157:1105-1112). The binding to AP-2 appears to play a critical role in the endocytosis and recycling of L1-CAM at the back of the growth cone, a process essential to the function of L1-CAM in growth cone migration (Kamiguchi and Yoshihara. J Neurosci 2001;21:9194-9203).

Axonal damage characterizes diseases such as spinal cord injury, traumatic brain injury, stroke, and neurodegenerative disease. Spinal cord injury affects millions of individuals worldwide, resulting in severe impairment of the physical function of affected persons (e.g., as seen in paraplegia and quadriplegia). Traumatic brain injury is a major health problem in all developed countries. Stroke is the second largest cause of death worldwide, and the main cause of long-term neurological disability. Neurodegenerative disease is of increasing concern with the aging of the population of the developed world. Currently available therapies are unable to repair the axonal damage. Therefore, the need exists in the art for therapies to repair neuronal damage, which therapies depend upon the ability to promote the outgrowth of spinal cord neurons to reestablish the damaged neuronal connections.

The outline of the sensory pathway is well known in the art. From the source of pain, pain messages move through peripheral sensory neurons and up the dorsal root ganglion of the spinal cord, where they stimulate interneurons in a relay destined for the brain. Pain messages can be blocked, enhanced, or modified at the relay between the peripheral neuron and the interneuron before progressing to the brain. From the spinal cord, the signal reaches the thalamus and cortex of the brain, where the location, intensity, and nature of the pain is decoded. Once the brain has interpreted the pain signal, the brain sends pain-suppressing chemicals to the pain source and triggers other related responses.

Neurotransmission between cells can be regulated by voltage-gated calcium channels, which mediate calcium influx in response to membrane depolarization. Voltage-dependent calcium channels are the primary trigger for electrically stimulated release of chemical transmitters in the nervous system that lead to stimulation of specific neuronal pathways. Electrical currents are used in neurons to rapidly transmit signals. All cells have a resting potential: an electrical charge across the plasma membrane, where the exterior of the cell is positive and the interior negative, due to the concentrations of different populations of charged ions. In neurons, voltage gated channels open or close in an "all-or-none" fashion in response to changes in the charge (measured in volts) across the plasma membrane of the cell. Activity- and receptor-dependent redistribution of ionotropic receptors has been widely studied in the post-synaptic density (Zhu J J et al., Cell. 2002 Aug. 23; 110(4): 443-55. Rao A, Craig A M., Neuron. 1997 Oct.; 19(4): 801-12.), but such studies have not previously been extended to proteins in the presynaptic active zones.

Dunlap and Fischbach (Dunlap K, et al. J. Physiol. 1981, 317: 519-5335) have suggested that transmitter-mediated shortening of the duration of the action potential could be due to a decrease in calcium conductance or a decrease in the number of functional channels in the membrane. Inhibition of $Ca^{2+}$ channels can be voltage-dependent, and is mediated by G protein beta-gamma subunits (Ikeda S R. Nature. 1996 Mar. 21; 380(6571): 255-8.; Herlitze S, et al. Nature. 1996 Mar. 21; 380(6571): 258-62.). In addition, kinases such as protein kinase C and tyrosine kinases have been shown to inhibit $Ca^{2+}$ channels (Hille B. Trends Neurosci. 1994 Dec.; 17(12): 531-6). Subsequent work has established that G protein-dependent inhibition of calcium current is in part a result of a decrease in the open probability of the channel, reducing current density (Delcour, Ah, and Tsien R W. 1993. Science February. 12, 259 (5097):989-4.). The idea that changes in channel density could underlie calcium channel modulation has not previously been tested. Alteration of a presynaptic calcium channel plasma membrane density to modulate calcium channel function will be useful in the control of neuronal signal propagation.

Chronic pain affects millions of individuals; it results in severe impairment of a patient's physical function and is often associated with psychological depression. Currently available therapies teach the use of analgesics to treat the symptoms of pain that result from the activation of pain pathways. These analgesics become less effective over time as patients become sensitized. Therefore, the need exists in the art for novel therapies for chronic pain that block pain pathway signals before they reach the brain.

Stroke and traumatic head injury result in similar pathological processes in the brain. In traumatic head injury, neurons die because they are crushed, setting off an inflammatory cascade that triggers further neuronal apoptosis. In stroke, the infarct results a similar cascade in the brain. Progressive inflammation and cell death downstream of the primary event is mediated by calcium flux across the neuronal cell membrane. Calcium flux through L type channels across the neuronal membrane and release from calcium stores leads to apoptosis. By blocking the calcium flux, one may block the cell death resulting from a or stroke traumatic head injury (Mattson M P, et al., Neuromolecular Med. 2003;3(2):65-94; Mody I, et al., Trends Pharmacol Sci. 1995; Oct.; 16(10):356-9; Zheng Z. et al., Curr Mol Med. 2003 Jun.;3(4):361-72). Thus, there exists in the art the need for novel methods to locally block calcium flux in the brain, in order to minimize apoptotic neuronal cell death immediately after stroke and traumatic head injury.

SUMMARY OF THE INVENTION

The present invention is directed towards a method for promoting outgrowth of a mammalian neuron comprising inhibiting the binding of an ankyrin protein of said neuron to an L1-CAM protein, by contacting said neuron with a peptide comprising the amino acid sequence set forth in SEQ ID NO: 2. In one aspect, the present invention is directed towards a method for treating diseases characterized by axonal damage selected from spinal cord injury, traumatic brain injury, stroke, and neurodegenerative disease, which comprises administering to a mammal in need of such treatment an effective amount for treating said diseases of a peptide comprising the sequence set forth in SEQ ID NO: 2, preferably in a human.

In a related aspect, the invention is directed towards a pharmaceutical composition for treating diseases characterized by axonal damage selected from spinal cord injury, traumatic brain injury, stroke, and neurodegenerative disease comprising peptide comprising the sequence set forth in SEQ ID NO: 2 and a pharmaceutically acceptable carrier. In another aspect, the invention is directed towards an isolated peptide comprising an amino acid sequence consisting of SEQ ID NO: 2 or isolated nucleic acid encoding the peptide. A further aspect may be an isolated peptide comprising an amino acid sequence consisting of SEQ ID NO: 2 linked to an isolated peptide comprising an amino acid sequence of SEQ ID NO: 6, wherein said peptides are linked by a disulfide bond.

In another aspect, the invention is directed towards a method of inhibiting neuronal signaling in a mammal which comprises disrupting the interaction between L1-CAM, ankyrin, and voltage-gated calcium channels, by contacting a neuron with a peptide comprising the amino acid sequence set forth in SEQ ID NO: 2. A related aspect is directed towards a method for treating pain in a mammal comprising disrupting the interaction between L1-CAM, ankyrin, and voltage-gated calcium channels in a subject in need of such treatment, which comprises administering an amount effective for the treatment of pain of a peptide comprising the sequence set forth in SEQ ID NO: 2, especially wherein said pain comprises chronic pain and the subject is a human In a related aspect the composition for the treatment of pain may be administered composition locally in the vicinity of the affected neurons, with an osmotic pump, to a region of the dorsal spinal cord.

In yet another aspect, the invention is directed towards a method for preventing neuronal cell death after an ischemic attack or stroke in a mammal comprising disrupting the interaction between L1-CAM, ankyrin, and voltage-gated calcium channels in a subject in need of such treatment which comprises administering to a subject in need of such treatment for an amount effective for the prevention of neuronal cell death of a peptide comprising the amino acid sequence set forth in SEQ ID NO: 2 in a subject in need of such treatment. In another aspect, the invention is directed towards a method for blocking neuronal calcium flux in a mammal comprising disrupting the interaction between L1-CAM, ankyrin, and voltage gated calcium in a subject in need of such treatment.

These and other aspects of the present invention will be apparent to those of ordinary skill in the art in light of the present description, claims, and drawings.

BRIEF DESCRIPTION OF THE DRAWINGS

FIGS. 7(A and B) depict the L1-CAM encoding nucleotide sequence (SEQ ID NO: 4). In FIG. 7A, the NheI site used to facilitate cloning of the sequence is in bold and underlined and the start codon (ATG) for translation of the L1-CAM protein is in bold and italicized. In FIG. 7A, the stop codon (TAG) signaling the end of translation of the L1-CAM protein is in bold and italicized and the XhoI site used to facilitate cloning of the sequence is in bold and underlined.

FIGS. 8(A and B) depict the amino acid sequence of the translated L1-CAM protein (SEQ ID NO: 5). The signal peptide, which is removed during procession to yield the mature L1-CAM protein, is underlined. Residues for which the amino acid sequence is different from that of endogenous rat L1-CAM (Miura et al. FEBS Lett. 1999;289:91-95, Genbank Accession # Q05695) are in bold and italicized. The "RSLE" mini-exon is indicated in bold.

FIG. 12 depicts a model of the complex involved in the retention of Ca$_v$2.2 channels at the plasma membrane.

DETAILED DESCRIPTION OF THE INVENTION

Definitions

Figure 1:
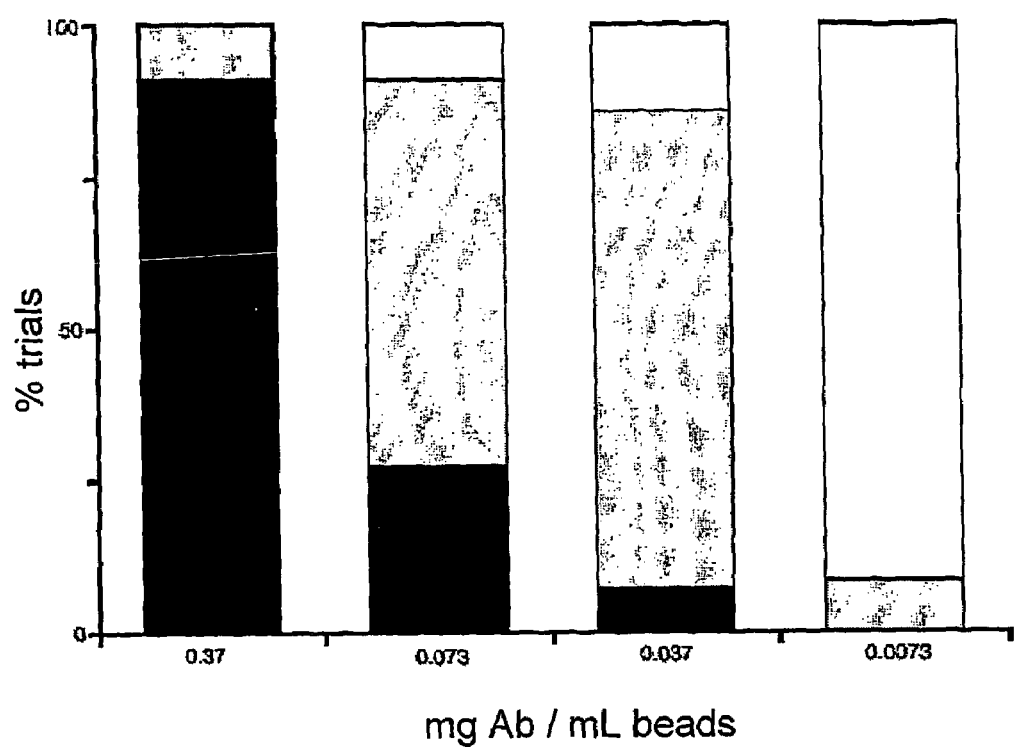
FIG. 1 is a bar graph of data for the binding of anti-myc antibody-coated beads to the cell surface of cultured rat neurons expressing myc-L1-CAM. The bar graph depicts the percentage of trials (% trials) versus concentration of 9E10 antibody bound to latex beads (mg Ab/mL beads). White bars indicate no binding of the beads to the cell surface. Grey bars indicate binding of beads to the cell surface, where the bound beads were not resistant to subsequent lateral displacement. Black bars indicate binding of beads to the cell surface, where the bound beads were resistant to subsequent lateral displacement.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

As used herein, the term "isolated" means that the referenced material is removed from its native environment, e.g., a cell. Thus, an isolated biological material can be free of some or all cellular components, i.e., components of the cells in which the native material is occurs naturally (e.g., cytoplasmic or membrane component). A material shall be deemed isolated if it is present in a cell extract or if it is present in a heterologous cell or cell extract. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organeue, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

As used herein the term "outgrowth" refers to extension, by a neuronal cell, of a cellular projection where such extension is mediated by the transduction of traction-forces generated by the neuronal growth cone cytoskeleton across the cell membrane to an extracellular substrate. Such cellular projections include, for example, lamella, axons, and dendrites. The extracellular substrate may be, for example, the surface of a tissue culture dish in vitro; the surface of another cell in vivo; or an extracellular matrix (ECM) in vivo. Such outgrowth may be associated, for example, with migratory cell behavior or axon guidance.

As used herein, "chronic pain" is defined as a: a state of physical, emotional, or mental lack of well-being or physical, emotional, or mental uneasiness that ranges from mild discomfort or dull distress to acute often unbearable agony, may be generalized or localized, and is the consequence of being injured or hurt physically or mentally or of some derangement of or lack of equilibrium in the physical or mental functions (as through disease), and that usually produces a reaction of wanting to avoid, escape, or destroy the causative factor and its effects; or b: a basic bodily sensation that is induced by a noxious stimulus, is received by naked nerve endings, is characterized by physical discomfort (as pricking, throbbing, or aching), and typically leads to evasive action that is c: marked by long duration, by frequent recurrence over a long time, and often by slowly progressing seriousness. (Miriam-Webster online medical dictionary 2003) This type of pain is resistant to most medical treatment and can often cause psychological problems.

The term "inhibiting" in regards to neuronal signaling is defined as reducing or suppressing the activity of a neuron or its ability to propagate an action potential.

The term "G-protein coupled receptors" or "GPCR" as defined herein as one of the major classes of proteins that transduce a signal within a cell. These receptors characteristically have seven-transmembrane domains and are made up of hetero- or homodimers. Extracellular ligands bind the GPCR to transmit a signal to the interior of the cell which results in a biological or physiological property change.

The term "G-protein" is defined herein to denote a protein that binds to and activates a "G-protein coupled receptor."

The term "Voltage gated calcium channel" as defined herein refers to a channel in a cell membrane whose opening is governed by the membrane potential. This channel will let calcium ions pass.

"Disrupting" in regards to an interaction between L1-CAM, ankryin, and voltage-gated calcium channels, is defined herein as the process of 1. breaking apart the interaction between any or all of the components that results in 2. voltage-gated calcium channel movement away from the plasma membrane into cytoplasmic vesicles.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

In accordance with the present invention there may be employed conventional molecular biology, microbiology, cell culture, protein expression and purification, antibody, and recombinant DNA techniques well known to those of ordinary skill in the art. Such techniques are explained fully in the literature. See, e.g., Sambrook, Fritsch and Maniatis, *Molecular Cloning: A Laboratory Manual,* Second Edition (Cold Spring Harbor Laboratory Press, New York: 1989); *DNA Cloning: A Practical Approach*, Volumes I and II (Glover ed.:1985); *Oligonucleotide Synthiesis* (Gait ed.: 1984); *Nucleic Acid Hybridization* (Hames & Higgins eds.: 1985); *Transcription And Translation* (Hames & Higgins, eds.:1984); *Animal Cell Culture* (Freshney, ed.:1986); *Immobilized Cells And Enzymes* (IRL Press: 1986); Perbal, *A Practical Guide To Molecular Cloning* (1984); Ausubel et al., eds. *Current Protocols in Molecular Biology*, (John Wiley & Sons, Inc.: 1994); and Harlow and Lane. *Antibodies: A Laboratory Manual* (Cold Spring Harbor Laboratory Press: 1988).

The present invention is based on the discovery that modulation of L1-CAM adhesion receptor-ankyrin cytoskeleton interactions plays an essential role in the regulation of neuronal outgrowth.

The function of adhesion receptors in both cell adhesion and migration depends critically on interactions with the cytoskeleton. During cell adhesion, cytoskeletal interactions stabilize receptors to strengthen adhesive contacts. In contrast, during cell migration, adhesion proteins are believed to interact with dynamic components of the cytoskeleton, permitting the transmission of traction forces through the receptor to the extracellular environment.

The L1-cell adhesion molecule (L1-CAM) is a member of the immunoglobin (Ig) super-family that plays a crucial role in both the migration of neuronal growth cones and the static adhesion between neighboring axons. The present invention is based on new findings regarding the regulation of L1-CAM function in neuronal outgrowth and cell adhesion.

A "mobile" adhesion receptor allows a cell to migrate, whereas a "stationary" version of the same adhesion receptor keeps the cell in place. L1-CAM is an adhesion receptor of the L1 family which promotes both growth cone extension in the developing central nervous system and cell adhesion mediated maintenance of axon bundles in mature neurons. L1-CAM switches its own kinetic behavior to modulate cell movements by interacting with other cellular components. "Stationary" L1-CAM, which is associated with adhesion depends in interaction with another protein called ankyrin to keep the cell stationary.

There are two ways to disrupt the binding between L1-CAM and ankyrin. The first is with a peptide derived from the L1-CAM cytoplasmic tail that mimics the ankyrin binding site (SEQ ID NO: 2). The second is with growth factors that indirectly phosphorylate the tail of L1-CAM. Release of the L1-CAM-ankyrin binding increases the amount of L1-CAM moving back along the upper surface of the cell, or "retrograde movement". The direction of retrograde receptor movement seen on the upper surface of the cell is thought to reflect the direction of traction forces generated on the lower surface that the cell is adhering to. It has recently been discovered that that release of stationary L1-CAM by the peptides of the invention comprising amino acids of SEQ ID NO: 2 produced greater neurite extension through growth cone migration.

During development, neurons may switch from migration in the growth cone to adhesion in the axon and synapse by increasingly dephosphorylating L1-CAM (and therefore promoting ankyrin binding). Thus, the peptides of the invention which interfere with L1-CAM-ankyrin binding may be used therapeutically to promote neuronal outgrowth in a patient in need of such treatment. Patients in need of such treatment are spinal cord injury, traumatic brain damage, neurodegeneration, etc.

In particular, the present invention provides methods to promote neuronal outgrowth or promote extension of a neuronal cell across a substrate by inhibiting the interaction of L1-CAM with ankyrin. This inhibition promotes retrograde movement of L1-CAM in association with retrograde moving components of the cytoskeleton, and permits the transduction of the traction forces involved in neural outgrowth from the neuronal cytoplasm to the exterior substrate.

The novel peptide of the invention is a peptide derived from the ankyrin binding domain of the L1 family members in which the carboxy-terminal tyrosine is substituted with phenylalanine and comprises the amino acid sequence QFNEDGSFIGQF (SEQ ID NO: 2). This amino acid sequence was derived from the 12 amino acid conserved region of the L1-CAM cytoplasmic tail that has been shown to be required for ankyrin binding to other L1-CAM family members (Zhang et al. J Biol Chem 1998;273:30785-30794). The tyrosine to phenylalanine substitution mimics the dephosphorylated, ankyrin-binding protein motif.

Peptides derived from the ankyrin binding domain of other L1 family members with a tyrosine to phenylalanine C-terminal substitution may also be used in the invention (Hortsch M. et al., Molecular and Cellular Neuroscience 15, 1-10 (2000)). The peptide comprising SEQ ID NO: 2 may be used with amino acid targeting sequences that allow translocation of the peptide across the plasma membrane and into the cytoplasm of cells. A non-limiting example is RQIKIWFQN-RRMKWKK (SEQ ID NO: 6), a 16 amino acid penetratin domain of the drosophila protein antennapedia, one of the penetration class of peptides with translocating properties capable of carrying hydrophilic compounds across the plasma membrane (Derossi D. et al., Trends Cell Biol 1998; 8:84-87). This class of peptides can be directly linked to SEQ ID NO: 2 to create, for example, "AP-YF" or RQIKIWFQN-RRMKWKKQFNEDGSFIGQF (SEQ ID NO: 3) for the direct targeting of the peptide of the present invention to the cytoplasm of cells. Non-limiting examples of penetration domains for use in the present invention are disclosed in Derossi et al. Trends Cell Biol 1998;8:84-87.

In an alternate embodiment, a peptide comprising the amino acid sequence QFNEDGSFIGQF (SEQ ID NO: 2) and disulphide-bridged to a delivery peptide such as the antennapedia domain (SEQ ID NO: 6) may be disulfide bonded through cysteine residues added to the N- or C-terminal ends of the existing peptides. For example, SEQ ID NO: 6 may be disulfide bonded through an additional C terminal cysteine residue RQIKIWFQNRRMKVKK$\underline{S}$ (SEQ ID NO: 24) to an additional N terminal cysteine residue attached to SEQ ID NO: 2 $\underline{S}$QFNEDGSFIGQF (SEQ ID NO: 25). Alternatively, SEQ ID NO: 2 may be disulfide bonded through an additional C terminal cysteine residue QPNEDGSFIGQF$\underline{S}$ (SEQ ID NO: 26) to an additional n terminal cysteine residue attached to SEQ ID NO: 6. $\underline{S}$RQIKIWFQNRRMKWKK (SEQ ID NO: 27). Once in the cytosol, the di-sulfide bond is reduced, dissociating the peptide complex into its component peptides. Thereafter, the free peptide comprising the amino acid sequence QFNEDGSFIGQF (SEQ ID NO: 2) is trapped within the cell, and can no longer pass through the plasma membrane. The use of the peptide of the invention (SEQ ID NO: 2) disulphide-bridged to a delivery peptide such as the antennapedia domain (SEQ ID NO: 6) limits the diffusion of the peptide to the diameter of a few cells. Once the peptide enters a cell it is reduced and the peptide of the present invention (SEQ ID NO: 2) cannot escape. Thus, an effective local concentration can be achieved in neurons at a lower administered dosage, with a smaller diameter of effective distribution.

The invention also provides isolated nucleic acids (RNA and DNA) encoding the peptides of the present invention, and sequence conservative variants thereof. "Sequence conservative variants" of the polypeptides of the present invention are those in which a change in one or more nucleotides in a given codon position (triplet) results in no change in the amino acid encoded at that position, as is know by those of ordinary skill in the art.

The novel peptide of the present invention can be used for promoting neuronal outgrowth, and for promoting extension of neuronal cells across a substrate, which inhibit the interaction of L1-CAM with ankyrin and promote directed movement of L1-CAM on the cell surface of neurons.

The ability to directly modulate L1-CAM-ankyrin binding using the peptide compounds of the invention has important implications in the treatment of various disease states characterized by axonal damage such as spinal cord injury, traumatic brain injury, stroke, and neurodegenerative disease. In these conditions, the axons of a neural cell may be severed or degraded. The neuron is alive but will be degraded from the site of injury back to the undamaged cell body. The use of the peptides of the invention enables neuronal outgrowth of the damaged axon out towards its proper connection. Thus, the present invention also provides a method for the treatment of spinal cord injury by administering an amount effective to treat spinal cord injury, traumatic brain injury, stroke, and neurodegenerative disease of the peptides of the invention to a subject in need of such treatment. By inhibiting the binding of L1-CAM and ankyrin, the peptides promote outgrowth of spinal cord neurons and promote the re-establishment of the damaged neuronal connections. In addition, the invention also provides pharmaceutical compositions for the treatment of spinal cord injury, traumatic brain injury, stroke, and neurodegenerative disease, which comprise the novel inhibitory peptides. Delivery of these peptides may be accomplished intrathecally to the spine or directly to the brain through the use of an osmotic pump.

In another aspect, the present invention is based on the discovery that voltage gated calcium channels are anchored at the plasma membrane of neuronal cells by an interaction with L1-CAM and ankyrin. Thus, disruption of the interaction by the peptide of the invention will block calcium signaling.

In neurotransmission, the arrival of an action potential opens calcium channels on the plasma membrane of a presynaptic neuron. This results in an influx of calcium ions into the cytoplasm, which triggers the fusion of cytoplasmic neurotransmitter-containing vesicles with the plasma membrane, resulting in neurotransmitter release into the synapse. Thus, the ability to block calcium influx at the presynaptic membrane can provide a means to control neural signaling. Specifically, voltage gated calcium channels must be located at the plasma membrane to regulate the flow of calcium ions into a neuron. Therefore, by removing calcium channels from the plasma membrane, action potentials arriving at a presynaptic neuron cannot stimulate a calcium influx, vesicle fusion cannot occur, and neurotransmitter will not be released into the synaptic cleft.

In the larger context of the sensory pathway, stimulation of peripheral sensory neurons triggers action potentials that send signals through sequential neurons leading to the brain. In a patient with chronic pain, signals carried by a subset of sensory neurons that mediate the transmission of painful stimuli activate (through synapses) relay neurons in the spinal cord that ultimately target higher centers in the brain where the pain is perceived. In such a patient, a specific blockade of neurotransmitter release at one of these intermediate synapses (e.g. by removal of the calcium channels from the presynaptic neuronal-cell membrane) prevents undesirable incoming sensory messages from reaching the brain.

The present invention is directed to methods of inhibiting neuronal signaling by disrupting the interaction between L1-CAM, ankyrin, and voltage-gated calcium channels. The present invention is based on the discovery that activation of G protein-coupled receptors alters the distribution of a subset of voltage gated calcium channels, the $Ca_v2.2$ channels. In dorsal root ganglion (DRG) neurons, an initial punctate distribution of $Ca_v2.2$ channels in the membrane was rapidly (within 2s) reduced by application of the neurotransmitter norepinephrine (NE) which function through G-protein coupled receptors. The time course for removal and reappearance of the channels in the membrane parallels the time course of transmitter-mediated inhibition of calcium current and desensitization of the response suggesting its role in neural signaling inhibition. Reduction in surface labeled calcium $Ca_v2.2$ channels was associated with a transient increase in cytoplasmic labeled channels suggesting that the $Ca_v2.2$ channels have moved in response to NE and $Ca_v2.2$ channels colocalized with markers for clathrin-coated vesicles in the cytoplasm, suggesting that they are in cytoplasmic vesicles. These results suggest that upon application of NE, $Ca_v2.2$ channels are removed from the plasma membrane and sequestered into clathrincoated vesicles in the cytoplasm. As these presynaptic $Ca_v2.2$ channels will not function in neurotransmission if removed from the cell surface, this finding suggested the design of novel methods to inhibit the propagation of neuronal signals.

One such method to inhibit the propagation of neuronal signals is to use the peptides of the invention described above. Pretreatment of DRG neurons with the AP-YF peptide (SEQ ID NO: 3), known to disrupt the interaction between L1-CAM and ankyrin (Gil O D et al, J. Cell. Biol. 2003, Aug. 18, 162 (4) 719-30), induces removal of $Ca_v2.2$ channels to the cytoplasm in a manner similar to that mediated by NE and other G proteins.

In particular, the present invention provides novel peptides for inhibiting neuronal signaling by disrupting the interaction between L1-CAM, ankyrin, and voltage-gated calcium channels, resulting in calcium channel translocation from the cell surface to the cytoplasm. The novel peptides of the invention comprise the amino acid sequence QPNEDGSFIGQF (SEQ ID NO: 2), the amino acid sequence of the L1-CAM ankyrin binding domain in which the carboxy-terminal tyrosine has been changed to phenylalanine.

The disruption of the L1-CAM-ankyrin interaction by the AP-YF peptide (SEQ ID NO: 3) inhibits $Ca_v2.2$ current through a cell and its ability to secrete Substance P (for pain), a polypeptide neurotransmitter that transmits pain impulses from peripheral receptors to the central nervous system a neuropeptide important in the transmission of painful stimuli. This evidence establishes an essential role for the interaction between L1-CAM, ankyrin, and voltage-gated calcium channels in the maintenance of $Ca_v2.2$ at the plasma membrane and in the secretion of Substance P in pain transmission.

In particular, the present invention provides methods for inhibiting neuronal signaling in pain transmission by disrupting the interaction between L1-CAM, ankyrin, and voltage-gated calcium channels. In particular, this method comprises the direct disruption of the interaction between L1-CAM, ankyrin, and voltage-gated calcium channels in the neuron by contacting neurons with a peptide comprising the amino acid sequence as set forth in SEQ ID NO: 2. Disruption of this interaction relocates the calcium channels to the cytoplasm of the cell, thus, inhibiting the movement of current through $Ca_v2.2$, blocking Substance P release into the synapse stopping the pain transmission from reaching the brain.

Thus, the invention is further directed to a method for treating pain by administering an amount effective to treat pain of a peptide comprising the sequence set forth in SEQ ID NO: 2 to a mammalian subject in need of such treatment. Chronic pain is a significant medical problem and difficult to treat due to bodily sensitization to otentially addictive analgesics and opiates. Thus, the present invention provides a novel method for treating chronic pain with no risk of sensitization or addiction. The treatment can be carried out by administering the peptides, via osmotic pump, preferably to the region of the dorsal spinal cord where synapses between primary sensory neurons and spinal cord relay neurons are located. The administration will disable calcium channel function, resulting in the cessation of the Substance P-mediated pain sensation signal to the brain.

Yet another embodiment of the present invention regards the use of the peptides of the invention comprising SEQ ID NO: 2 for blocking calcium flux leading to apoptosis. In particular, this method comprises the direct disruption of the interaction between L1-CAM, ankyrin, and voltage-gated calcium channels in the neuron by contacting neurons with a peptide comprising the amino acid sequence as set forth in SEQ ID NO: 2. Disruption of this interaction relocates the calcium channels to the cytoplasm of the cell, blocking calcium flux and calcium signaling.

Calcium flux across the neuronal cell membrane mediates progressive inflammation and neuronal cell death resulting from stroke or traumatic head injury. Specifically, calcium flux through L type channels across the neuronal membrane and release from calcium stores leads to neuronal cell apoptosis or cell death. By blocking the calcium flux, cell death is blocked resulting from a stroke or traumatic head injury (Mattson M P, et al., Neuromolecular Med. 2003;3(2):65-94; Mody I, et al., Trends Pharmacol Sci. 1995 Oct.; 16(10):356-9; Zheng Z. et al., Curr Mol Med. 2003 Jun.; 3(4):361-72). The peptide of the invention comprising SEQ ID NO: 2 may be used to temporarily block calcium flux in neurons in a specific location. Thus, the peptide of the invention comprising SEQ ID NO: 2 may be used in the prophylaxis of stroke or traumatic head injury induced neuronal death in a patient in need of such treatment within the first 24 hours of the event. Administration of the peptide may be bolus via catheter, as the patient will likely be operated upon within the first 24 hours post injury.

Stereoisomers (e.g., D-amino acids) of the twenty conventional amino acids, unnatural amino acids such as a,a-disubstituted amino acids, N-alkyl amino acids, lactic acid, and other unconventional amino acids may also be suitable components for the peptide compounds of the present invention. Examples of unconventional amino acids include, but are not limited to: β-alanine, 3-pyridylalanine, 4-hydroxyproline, O-phosphoserine, N-methylglycine, N-acetylserine, N-formylmethionine, 3-methylhistidine, 5-hydroxylysine, nor-leucine, and other similar amino acids and imino acids.

Preparation of the Peptide Compounds of the Invention

Peptide synthesis: The peptides of the invention may be prepared by classical methods known in the art. These standard methods include exclusive solid phase synthesis, partial solid phase synthesis methods, fragment condensation, classical solution synthesis, and recombinant DNA technology [See, e.g., Merrifield J. Am. Chem. Soc. 1963 85:2149].

A preferred method for peptide synthesis is solid phase synthesis. Solid phase peptide synthesis procedures are well-known in the art [see, e.g., Stewart *Solid Phase Peptide Syntheses* (Freeman and Co.: San Francisco) 1969; 2002/2003 General Catalog from Novabiochem Corp, San Diego, USA; Goodman *Synthesis of Peptides and Peptidomimetics* (Houben-Weyl, Stuttgart) 2002].

These solid phase synthesis methods can also be used to synthesize peptides in which amino acids other than the 20 naturally occurring, genetically encoded amino acids are substituted at one, two, or more positions of any of the compounds of the invention. Synthetic amino acids that can be substituted into the peptides of the present invention include, but are not limited to, N-methyl, L-hydroxypropyl, L-3,4-dihydroxyphenylalanyl, δ amino acids such as L-δ-hydroxylysyl and D-δ-methylalanyl, L-α-methylalanyl, β amino acids, and isoquinolyl. D-amino acids and non-naturally occurring synthetic amino acids can also be incorporated into the peptides of the present invention.

In addition, the peptides of the present invention can be produced recombinantly using appropriate microbial, yeast, insect or mammalian expression systems well known for those of ordinary skill in the art, using nucleic acids encoding the peptides.

Use of Inhibitory Peptides of the Invention

The peptide compounds of the invention are useful in vitro as tools for understanding the biological importance of L1-CAM binding to ankyrin, including evaluation of the many factors thought to influence, and be influenced by, neuronal cell adhesion and migration (e.g., the mechanism of neuronal traction force generation). The present peptides are also useful in the development of other compounds that inhibit the binding of L1-CAM to ankyrin and promote neuronal outgrowth, because the present compounds provide important structure-activity-relationship information that facilitate that development.

The peptides of the invention can also be utilized as commercial reagents for various medical research and diagnostic purposes. Such uses can include, for example, use as a calibration standard for quantiting the activities of candidate L1-CAM-ankyrin binding inhibitory peptides in a variety of functional assays, and use to maintain the outgrowth in vitro cultured neuronal cell lines.

In yet another aspect of the present invention, methods of treatment and manufacture of a pharmaceutical composition are provided. The peptide compounds of the invention may be administered to mammals, including humans, to inhibit the binding of L1-CAM to ankyrin in vivo. Thus, the present invention encompasses methods for therapeutic treatment of disorders associated with neuronal damage (e.g., spinal cord injury, stroke, traumatic brain injury, and neurodegenerative diseases), which methods comprise administering a peptide of the invention in amounts effective to stimulate neuronal outgrowth in vitro. Thus, the present invention encompasses methods for prevention of neuronal cell death due to stroke or traumatic head injury by administering an amount of the peptide of the invention to prevent neuronal cell death in vivo in a mammal in need of such treatment. For example, the peptides of this invention will find use in the prevention of neuronal cell death due to calcium signaling of apoptosis triggered by stroke or traumatic brain injury.

As peptide drugs have a very short half life in live tissues and [bodily fluids] (about 4 hours), and diffusion of the administered peptide will be in 3 dimensions not limited by cell boundaries, administration of the peptide can be visualized as starting from a point source and diffusions out to the surrounding environment where peptides can bind. This model suggests that a steep concentration gradient is where the peptide is most concentrated at the tip of the cannula created at the site of injection of the peptide. The rate of diffusion may be tested experimentally, for example, by injecting a labeled peptide into spinal cord cerebrospinal fluid (CSF) at a fixed rate. CSF is then collected from different sites at fixed time intervals. The tissue is rapidly fixed and the spinal cord region is sectioned to determine how much peptide is bound locally in the subdural space. This may be determined directly by immunohistochemistry. For example, the penetration domain peptide (SEQ ID NO: 6) conjugated to a myc epitope a small peptide tag attached to identify the location of peptides or proteins may be administered to the CSF of a rat via an osmotic pump using a cannula, CSF samples taken at [a distance] to determine the standing gradient in the cerebrospinal fluid the rat will then be anesthetized, perfusion fixed, sacrificed and the spinal cord tissue surrounding the cannula tip sectioned to directly detect peptide binding by immunohistochemistry with an anti-myc antibody against the myc-tagged penetration peptide. As the peptide was degraded, the epitope would similarly degrade, so one would be able to easily determine the effective range and concentration of active peptide.

As the effective peptide concentration in a rat is directly analogous to that of a human, the rate of diffusion and effective half-life of the peptides of the invention may be determined experimentally. Previous experiments performed with antibodies have demonstrated very little diffusion; as antibodies are proteins these results are analogous to the activity of small peptides. (Roonprapunt C., et al., Journal of Neurotrauma, Vol. 20, No. 9, 2003). Thus, the important determination is the concentration at the tip of the cannula, as rapid degradation of the peptides render them ineffective at a distance. If the prediction is correct, the administered peptide would be undetectable at a short distance from the injection site (i.e. greater than 100 cell bodies=about 5 mm; Roonprapunt C., et al., Journal of Neurotrauma, Vol. 20, No. 9, 2003).

The use of the peptide of the invention (SEQ ID NO: 2) disulphide-bridged to a delivery peptide such as the antennapedia domain (SEQ ID NO: 6) circumvents issues of undesirable peptide diffusion by limiting the diffusion to the diameter of a few cells: once the peptide enters a cell it is reduced and the functional domain peptide of the invention cannot escape. Thus a higher effective concentration could be obtained with a lower delivery dosage.

In one embodiment, the peptides of this invention may be used to treat spinal cord injury in mammals. Specifically, the peptides of the invention may be used for the treatment of damage to axonal processes in the spinal cord. Preferred modes of administration of the therapeutic peptides are intrathecal at the site of spinal cord injury or in the brain, such as by bolus administration or by using a cannula with an osmotic pump. A preferred mode of administration of the therapeutic peptide is intrathecally: to target the location in the dorsal spinal cord—where synapses between the pain-carrying primary sensory neurons communicate with spinal cord neurons carrying the signal to the brain—by inserting a cannula with an osmotic pump in the vicinity of the affected neurons. Bolus administration intrathecally may be within the first 24 hours post stroke or traumatic brain injury. Intrathecal administration may be possible as the patient may already be undergoing invasive surgery; this method of administration may be location-specific to the area of inflammation and neural cell death, which may be found by MRI. As spiral cord injury generally results from a traumatic event, administration within 24 hours would be possible by bolus during post traumatic surgery. These preferred modes of administration will minimize non-specific effects on ankyrin function in the maintenance of cell structure in other tissues.

Based on values determined from experiments in mice, a typical dosage for treatment of a human subject will be in the range of 1-10 µg of peptide delivered into the sub-dural space adjacent to the site of injury by cannula at a rate of 1.5 ml/hr for a period of approximately 4 weeks following injury. Exact duration of treatment may be modified by the skilled practitioner based upon the general physical state of the patient, the severity of injury, and any clinical observations of improvement in motor and/or sensory function in the affected areas. Results from animal models will also provide information on appropriate treatment durations.

For all of the peptide compounds, as further studies are conducted, information will emerge regarding appropriate dosage levels for treatment of various conditions in various patients, and the ordinary skilled worker, considering that the exact range would be dependent upon therapeutic context, age, and general health of the recipient, will be able to ascertain proper dosing. The selected dosage depends upon the desired therapeutic effect, on the route of administration, and on the duration of the treatment desired. The dosing schedule may vary, depending on the circulation half-life, and the formulation used.

Based on results from animal model systems or results from direct assessment of peptide concentration in human cerebrospinal fluid, peptide dosage may need to be adjusted to maintain an effective concentration at the site of injury in the range of 1-10 mg/ml of peptide. All concentrations within this range are expected to promote neurite outgrowth. Within this range, exact dosage for a particular patient will be determined by the skilled practitioner based upon the general physical state of the patient and the severity of injury, and may be modified during the course of treatment based upon clinical observation of degree of improvement in motor and/or sensory function of the particular patient.

Thus, the present invention encompasses methods for therapeutic treatment of disorders associated with chronic pain by administering an amount of the peptide of the invention to alleviate pain in vivo in a mammal in need of such treatment. For example, the peptides of this invention will find use in the treatment of chronic pain.

Peptides of the invention may be used in conjunction with other therapeutics. For example, in spinal cord injury, therapeutics may target suppressing the initial inflammatory cascade as well as addressing the disconnect between the upper and lower part of the neurons. Thus, the peptides of the present invention may be utilized in conjuction with anti-inflammatory agent, and either neurotrophic growth factors or neuronal stem cells.

Pharmaceutical Compositions

In yet another aspect of the present invention, pharmaceutical compositions of the above inhibitory peptide compounds are provided. Conditions alleviated or modulated by the administration of such compositions include those indicated above. Such pharmaceutical compositions may be for intrathecal administration routes of administration and can be formulated in appropriate dosage forms. In general, comprehended by the invention are pharmaceutical compositions comprising the inhibitory peptide, or derivative products, of the invention together with pharmaceutically acceptable diluents, preservatives, solubilizers, emulsifiers, adjuvants and/or carriers. Such compositions include diluents of various buffer content (e.g.,.Tris-HCl, acetate, phosphate), pH and ionic strength; additives such as detergents and solubilizing agents (e.g., Tween 20, Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid, water, and DMSO (dimethyl sulfoxide) may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form.

The compounds may be formulated in a variety of ways and may be used by themselves or in conjunction with other drugs. The formulation will be in a physiologically acceptable medium, which should be readily acceptable as a medium for repetitive introduction or continuous introduction into the host. Convenient media include saline, phosphate buffered saline, lactated Ringer's solution, 5% dextrose in water, polyethyleneglycol and the like.

Where there has already been an onset of stroke, desirably, an initial bolus may be administered to the patient intrathecally. Therefore, it will be preferable to introduce the bolus using, for example, a cannula. The same media which are used for the infusion may also be used for the bolus, although other media may be used as well, such as normal saline, ¼ normal saline, ½ normal saline, lactated Ringer's solution, 5% dextrose in water, and polyethyleneglycol. The concentration in the bolus will generally be from about 0.5% to 5%, more usually from about 1% to 2%.

Preferably, the bolus is administered within a relatively short time after the stroke, within about 24 hours, broadly from about zero to twelve hours, preferably from about zero to six hours.

After administration of the bolus, various means may be employed for maintaining a relatively constant concentration of the peptides of the present invention in the patient. A pump may be implanted in the patient, so as to continuously provide the desired level of drug. Various pumps are commercially available, such as the Alzet osmotic pump, model 2MLI, Alza Corp., Palo Alto, Calif.

EXAMPLES

The present invention is described further below by means of the following examples. However, the use of these and other examples anywhere in the specification is illustrative only, and in no way limits the scope and meaning of the invention or of any exemplified form.

Example 1

Assembly of Expression Constructs pL1-CAM: This expression vector contains a nucleotide sequence (FIG. 7; SEQ ID NO: 4) encoding the L1-CAM protein (FIG. 8; SEQ ID NO:5) inserted into the NheI and XhoI sites of pIRES2-EGFP (Clontech). This expression construct provides for the expression of both L1-CAM and enhanced green fluorescent protein (EGFP) from a single bicistronic transcript containing an internal ribosomal entry site (IRES), where expression is regulated by a cytomegalovirus (CMV) promoter.

The L1-CAM-encoding nucleotide sequence (SEQ ID NO: 4) represents a variant of the nucleotide sequence for rat L1-CAM. The L1-CAM protein (SEQ ID NO: 5) encoded by the nucleotide sequence (SEQ ID NO: 4) is 99.44% identical to the rat L1-CAM protein previously reported by Miura et al. FEBS Lett. 1999;289:91-95 (Genbank Accession # Q05695). The two amino acid sequences differ at only 7 positions (see FIG. 8). Three of these changes are in the 21 amino acid signal sequence, and therefore are not present in the mature protein (such that the mature protein amino acid sequences are 99.7% identical). The remaining four positions of are within mature protein; in all cases the differences are conservative, or residue is the same is the equivalent position in mouse L1-CAM, or both. Therefore, for the purposes of these experiments, the L1-CAM protein is functionally equivalent to the mature rat L1-CAM protein. Accordingly, the described examples could also be performed using the nucleotide sequence that encodes the rat L1-CAM protein (see Genbank Accession # Q05695).

pMyc-L1-CAM: The rat L1-CAM-encoding nucleotide sequence (SEQ ID NO: 4) of the L1-CAM construct was modified by PCR to include a 10 amino-acid myc epitope (EQKLISEEDL; SEQ ID NO: 9) 4 amino acids after the predicted amino terminus of the mature protein (IPDEQKLISEEDLYKGHH (SEQ ID NO: 10); 9 inserted amino acids indicated in bold case). The insertion is upstream of miniexon 2 which has been shown to play a role in L1-binding to neural ligands (De Angelis et al. J Biol Chem 2001;276: 32738-32742).

Introduction of the myc epitope was carried out using a 2-step PCR protocol. First, two independent PCR reactions using the L1-CAM-encoding nucleotide sequence (SEQ ID NO: 4) as a template were carried out to generate two products. The first reaction used the primers A (5'-ATT ACC CGG GCT AGC TAT GGT CGT GAT GCT GCG G-3'; SEQ ID NO: 11) and BL (5'-TAG ATC CTC TTC ACT TAT TAA CTT CTG TTC ATC AGG AAT CTG TAT-3'; SEQ ID NO: 12) to generate a PCR product with the myc-epitope encoding sequences at its 3' end. The second reaction used the primers BU (5'-CAG AAG TIA ATA AGT GAA GAG GAT CTA TAT AAA GGA CAC CAT GTA-3'; SEQ ID NO: 13) and C (5'-CTT CCA CAG TGA CAT AGT AGG CAT-3'; SEQ ID NO:14) to generate a PCR product with the myc-epitope encoding sequences at its 5'end.

The products from each reaction were purified, mixed and subject to a second step of PCR using the primers A and C. This step yields a single product with the myc epitope in the middle and restriction sites (Xma1, Sph1) at either end of the product. This PCR product was then digested with Xma1 and Sph1, and ligated into Xma1 and Sph1 digested pL1-CAM construct, in order to replace the 5' end of the untagged-L1-CAM-encoding nucleotide sequence with this myc-tagged-L1-CAM-encoding sequence.

This expression construct provides for the expression of both myc-L1-CAM and enhanced green fluorescent protein (EGFP) from a single bicistronic transcript containing an internal ribosomal entry site (IRES), where expression is regulated by a cytomegalovirus (CMV) promoter.

pMyc-L1-CAM-YF, pMyc-L1-CAM-YH, pMyc-L1-CAM-STOP: Mutations in the cytoplasmic tail of the L1-CAM sequences were introduced directly into the pMyc-L1-CAM expression construct using the QuikChange™ Site-Directed Mutagenesis kit (Stratagene). This mutagenesis provided for Y to F, or Y to H, amino acid substitutions at tyrosine 1229 by replacing the codon TAC with TTC (Y to F in pMyc-L1-CAM-YF), or CAC (Y to H in pMyc-L1-CAM-YH), respectively. For the STOP mutant, at stop codon was introduced after 4 amino acids of the cytoplasmic tail, in order to generate a truncated L1-CAM protein, which is inserted in the plasma membrane, but which lacks the L1-CAM cytoplasmic region.

Mutagenesis was performed according to manufacturer's instructions using the following primer sets: For pMyc-L1-CAM-YF, the mutagenesis primers were YF-upper (5'-GGC TCT TTC ATC GGT CAA TTC AGT GGC AAA AAA-3'; SEQ ID NO: 15) and YF-lower (5'-TTT TTT GCC ACT GAA TTG ACC GAT GAA AGA GCC-3'; SEQ ID NO: 16). For pMyc-L1-CAM-YH, the mutagenesis primers were YH-upper (5'-GGC TCT TTC ATC GGT CAA CAC AGT GGC AAA AAA-3'; SEQ ID NO: 17) and YH-lower (5'-TTT TTT GCC ACT GTG TTG ACC GAT GAA AGA GCC-3'; SEQ ID NO: 18). For pMyc-L1-CAM-YH, the mutagenesis primers were Stop-upper (5'-TTC ATC AAA CGC AGT TAG GGT GGC AAA TAC TCA G-3'; SEQ ID NO: 19) and Stop-lower (5'-CTG AGT ATT TGC CAC CCT AAC TGC GTT TGA TGA A-3'; SEQ ID NO: 20).

These expression constructs provide for the expression of both myc-L1-CAM-YF, myc-L1-CAM-YH, or myc-L1-

CAM-STOP and enhanced green fluorescent protein (EGFP) from a single bicistronic transcript containing an internal ribosomal entry site (IRES), where expression is regulated by a cytomegalovirus (CMV) promoter.

pL1-CAM-GFP: In order to generate pL1-CAM-GFP, the sequences encoding the C-terminal portion of L1-CAM were first amplified via PCR. The primers used in this PCR introduced flanking HindIII sites. The 3' HindIII site was introduced upstream of the stop codon so as to permit in frame fusion of the L1-CAM coding region with the GFP coding region. This PCR was performed on pL1-CAM as template using the primers Upper (5'-CCG CGG AAGCTT GAG GTA CAG GCC TTT AAT GG-3'; SEQ ID NO: 21) and Lower (5'-GGG CCC AAGCTT TTC TAG GGC TAC TGC AGG-3'; SEQ ID NO: 22), where the HindIII sites are underlined, and the rat L1-CAM-encoding sequences are in bold. This PCR product was then digested with HindIII and inserted into a HindIII-digested GFP2 Fusion Protein Expression Vector (Biosignal; Perkin Elmer). Insert orientation was subsequently verified by restriction digest using Xho1 and Sal1 enzymes. This intermediate construct was called pL1-CAM-GFP-INT.

The remaining L1-CAM encoding sequences were excised from a pBS-L1-CAM construct by digestion with NotI and AgeI. pBS-L1-CAM contains the L1-CAM-encoding nucleotide sequence (SEQ ID NO: 4) inserted into the multiple cloning site of the pBluescript vector (Stratagene). NotI cuts 5' of the start codon (ATG) for L1-CAM translation, while the AgeI site cuts within the sequences encompassed by the primers Upper and Lower (used for the PCR, above).

pL1-CAM-GFP-INT was digested with NotI and AgeI, and then ligated with the excised NotI-AgeI fragment from pBS-L1-CAM to form the final pL1-CAM-GFP construct. This expression construct provides for the expression of a L1-CAM-GFP fusion protein.

Example 2

Expression of Wild-type and Mutant L1-CAM in in vitro Cultured Rat Neurons

Materials and Methods

Cell culture aid transfection: ND-7 cells were generated by poly-ethylene glycol-mediated fusion of N18Tg2 neuroblastoma cells (German Collection of Microorganisms and Cell Cultures, Braunschweig, Germany) with dorsal root ganglion (DRG) cells harvested from neonatal rat. These parent cell lines were cultured in vitro by standard techniques well established in the art (see, e.g., *Animal Cell Culture* (Freshney, ed.: 1986). ND-7 cells were routinely cultured in L15 medium (Gibco), supplemented with penicillin, streptomycin, L-glutamine, and vitamins (all available from Cell and Molecular Technologies), containing 10% bovine calf serum (Hyclone), and buffered for $CO_2$. Cultured ND-7 cells were plated on sialanized and laminin-coated coverslips 24 hours prior to transfection. Plated cells were transfected with pMyc-L1-CAM, pMyc-L1-CAM-YF or pMyc-L1-CAM-YH expression constructs using Lipofectamine plus (Invitrogen) according to manufacturer's instructions. Transfected cells were cultured for 24-36 hours, and then fixed for immunohistochemistry. Cells transfected with the bicistronic expression constructs express a single mRNA encoding both the myc-L1-CAM proteins and EGFP, such that transfected cells were identified by EGFP fluorescence.

Immunohistochemishly: Cells were fixed for 10 minutes using 1% paraformaldehyde in PHEM (60 mM PIPES, 25 mM HEPES, 10 mM EGTA and 2 mM $MgCl_2$). For ankyrin staining, cells were permeabilized for 6 minutes in PHEM containing 0.1% Triton-X100 and 0.05 mM glycine. Fixed cells were blocked using 0.05 mM glycine, 1% BSA and 1% normal donkey serum (Jackson Immunochemicals) in PHEM. All subsequent incubations were carried out in 0.05 mM glycine in PHP-M.

The myc-L1-CAM variants were detected using a monoclonal anti-myc mouse antibody, 9E10 (Developmental Studies Hybridoma Bank, University of Iowa; se also Evan et al. Mol Cell Biol 1985;5:3610-3616). Ankyrin was detected using a monoclonal anti-ankyrinB mouse antibody (BD PharMingen). Endogenous rat L1-CAM was detected in untransfected ND-7 cells using a polyclonal anti-L1-CAM rabbit antibody. This polyclonal antiserum was generated using standard techniques well established in the art (see, for example Harlow and Lane. *Antibodies: A Laboratory Manual* (Cold Spring Harbor Laboratory Press: 1988)), by immunizing rabbits with purified mouse L1-CAM protein (Genbank Accession # AAF22153). This antiserum detects both mouse and rat L1-CAM proteins. Primary antibodies where then detected with either donkey anti-rabbit or donkey anti-mouse secondary antibodies conjugated to indocarbocyanin Cy3 (Jackson ImmunoResearch). In negative control samples, fixed cells were incubated with secondary antibody only.

Fluorescent signal of bound secondary-antibodies was then visualized using a Zeiss Axiovert 100TV microscope using a 100× plan neofluor objective (NA 1.4). Micrographs were collected using a cooled CCD camera (Coolsnap HQ; Roper Scientific) under the control of Isee imaging software (Isee Imaging). Images were subsequently processed in Photoshop (Adobe) to maximize contrast and subject to an unsharp mask.

Results and Discussion

Full-length rat L1-CAM including the neuron-specific RSLE exon was expressed in ND-7 cells (rat DRG/neuroblastoma hybrid; Dunn et al. Brain Res 1991;545:80-86) to provide a controlled background on which to characterize L1-CAM function. Indirect immunofluorescence assays confirmed that these adherent cells express both endogenous L1-CAM on the cell surface and ankyrin B in the cytoplasm. ND-7 cells were transfected transiently with pMyc-L1-CAM, pMyc-L1-CAM-YF, or pMyc-L1-CAM-YH expression constructs to permit the detection of the ectopic L1-CAM proteins in the context of the endogenous L1-CAM. Expression of the myc-tagged L1-CAM proteins was detected by indirect immunofluorescence using an anti-myc antibody (9E10). Myc-L1-CAM appeared on the cell surface of transfected cells with a distribution that was similar to that of endogenous L1-CAM. Mutant forms of L1-CAM encoding single amino acid substitutions at tyrosine 1229, including myc-L1-CAM-YF and myc-L1-CAM-YH were similarly indistinguishable in distribution from endogenous protein. The similarity in distribution of the epitope-tagged L1-CAM proteins and the endogenous protein indicates that the ectopic myc-L1-CAM proteins were appropriately transported and distributed on the cell surface. Furthermore, the expression levels of the myc-L1-CAM variants correlated well with EGFP expression in transfected cells.

Example 3

L1-CAM Cytoskeleton Interactions Depend on L1-CAM Crosslinking

Material and Methods

Cell culture and transfection: ND-7 cells (rat neuroblastoma/DRG hybrid cells) were cultured as described in Example 2. 24 hours prior to transfection, cultured cells were plated on coverslips coated with poly-D-lysine and laminin sealed to the bottom of 35 mm culture dishes (Mattek Corp.). Plated cells were transfected with the pL1-CAM or pMyc-L1-CAM expression constructs using Lipofectamine plus (Invitrogen) according to manufacturer's instructions. Transfected cells were cultured for 24-36 hours, and then used for live microscopy. For laser trap and video microscopy, the medium was replaced with phenol red-free serum-free L15 medium (air buffered) with 20 mM HEPES, 0.1% BSA, 0.5% ovalbumin. Cells transfected with the bicistronic expression constructs express a single mRNA encoding both the myc-L1-CAM proteins and EGFP, such that transfected cells were identified by EGFP fluorescence.

Bead preparation: Beads were prepared as follows (described previously, e.g., in Choquet et al. Cell 1997;88:39-48 and Felsenfeld et al. Nat Cell Bio 1999;1:200-206): 1 μm carboxylated latex microspheres (Polyscience) were covalently coupled to ovalbumin (fraction VII; Sigma) using a carbodiimide linkage to neutralize the bead surface. Ovalbumin-coated beads were subsequently derivatized with Sulpho-NHS-LC-biotin (Pierce). Beads at this stage were used fresh or stored for up to two weeks at 4° C. Biotinylated beads were subsequently incubated with an excess of neutravidin (Molecular Probes) overnight at 4° C. Beads were washed extensively and a small aliquot (15 μl; based on starting concentration) was incubated with various concentrations of biotinylated 9E10 monoclonal anti-myc mouse antibody (Developmental Studies Hybridoma Bank, University of Iowa) for 1 hr at room temp or overnight at 4° C. the concentration of antibody is described in units of mg Ab/mL beads, where this ratio refers to the amount of unbound antibody added per starting volume of beads during bead preparation. Unreacted sites were blocked with biotin-BSA (BSA-biotinamidocaproyl; Sigma). Beads were sonicated for 5 seconds in a 0° C. bath sonicator prior to experiments.

Video microscopy, laser tweezers, and data analysis: The 9E10-coated latex beads were then placed and held with an optical gradient laser trap on the surface of transfected cells at a distance of between 0.5 and 1 μm from the leading edge for 2 seconds. The laser trap consisted of a Titanium Sapphire (Coherent; model 890) solid state laser pumped by a 5 W frequency-doubled Neodymnium Vanadate laser (Verdi; Coherent) and tuned to 800 nm. This wavelength was previously determined to generate the fewest heating artifacts in live cells (Svoboda and Block. Biomol Struct 1994;23:-247-285 and Choquet et al. Cell 1997;88:39-48). Laser power at the output of the Titanium Sapphire laser was 40 mW, and prepared beads were placed and held on the cell surface for less than 3 sec to further reduce the possibility of heating artifacts. Laser light was introduced through the television port of the Axiovert microscope.

For cytoskeleton attachment assays, bound beads were retested with a second pulse from the laser trap applied approximately 0.5 bead diameters from the bead center.

Video microscopy was carried out on a Zeiss Axiovert 100 TV according to techniques well known in the art. Transfected cells on laminin-coated coverslips were cultured in sealed chambers permitting illumination with a high-resolution, oil immersion condenser. Images were collected and laser trap formed through a 100× plan neofluor NA1.4 objective.

Each trial consisted of a single bead placed on the surface or a single cell. Binding was scored based on the percentage of beads that remained attached to the cell surface for >10 seconds. Bound beads were then subjected to a second pulse to test lateral displacement. In these cytoskeletal attachment assays, lateral movement of beads less than 0.2 μm was scored as rigidly attached. Thus, rigid beads were described as the percentage of beads that were resistant to lateral displacement of greater than 0.2 μM.

Video images of bead movement were collected using a newvicon camera (Dage MTI; VE-1000N) and background subtraction and contrast enhancement were carried using a Hamamatsu Argus 20 image processor. Raw data were recorded to sVHS video tape for subsequent analysis. Video recordings were subsequently digitized onto an Intel processor-based computer running the Isee imaging software (Isee Imaging) running under Red Hat Linux 7.1. Quantification of bead movement was carried out in Isee. Diffusional analysis was carried out using a custom spreadsheet in Excel (Microsoft). This spreadsheet carries out 4 operations: first, it scales the data from pixel measurements to nm using the appropriate scale factor (determined by the magnification used to observe bead movement); second, it subtracts the first point from all of the data, to set the origin at 0,0 (x,y coordinates); third, it rotates (in two dimensional space) the data around the origin so that the orientation of the cell is the same from trial to trial (here, the data was set so that the cells all face to the left); and fourth, the spreadsheet calculates the mean square displacement (MSD) data which are used to calculate diffusion coefficients and bead velocity. Individual traces were scored blind for classes of behavior. Statistical analysis of percentages of trials was carried out using chi-squared analysis or a Fisher's exact probability test.

MSD values were calculated as previously described (see Qian et al, 1991; Biophysical Journal 60 p910). For these calculations, the squared displacement ($a^2+b^2$; where $a=x_{n+t}-x_n$, $b=a=y_{n+t}-y_n$ for any two points separated by time t) of the bead was calculated between two points in the data set. The mean of the squared displacements was calculated for each time interval t=1 to m, where m is the time interval that equals 10% of the length of the data set. The mean displacement was plotted with respect to time giving a curve with a linear or quadratic shape, depending on the behavior of the bead. Diffusion rates and velocity were calculated by fitting the curve with the equation $MSD=4Dt+v^2t^2$, where D is the diffusion coefficient, v is the velocity and t is time. D and v were calculated for each bead independently and presented as averages or as individual values, as described in each case.

Results and Discussion

To begin to characterize the regulation of L1-cytoskeleton interactions, the lateral mobility of cell-surface L1-CAM in cultured cell lines was examined. Quantifying directly the movement of receptors on the upper surface of the cell provides an accurate reflection of receptor function along the lower surface where cells exert traction forces during migration (Galbraith and Sheetz J Cell Biol 1999; 147:1313-1324). For these assays, rat ND-7 cells were transfected with the pL1-CAM or pMyc-L1-CAM expression constructs. Thereby, full-length rat L1-CAM including the neuron-specific RSLE exon was expressed in ND-7 cells to provide a controlled background on which to characterize L1-CAM function. ND-7 cells spread and polarize, producing large lamella (>15 μm across), making them well suited to observation by video microscopy.

Latex beads (1 μm) coated with 9E10, an anti-myc antibody, were placed and held with an optical gradient laser trap on the cell surface of transfected cells at a distance of between 0.5 and 1 μm from the leading edge for 2 seconds.

Following placement with a laser trap, latex beads coated with anti-myc antibodies bound to cell-surface myc-L1-CAM in a concentration-dependent manner (FIG. 1, white bars indicate no binding, grey and black bars indicate binding). Bead binding to the cell surface varied with antibody concentration and fell off dramatically between 0.037 and 0.0073 mg/ml beads (FIG. 1). Additionally, binding of beads coated with a high concentration of 9E10 (0.58 mg/ml beads) to cells transfected with pL1-CAM (which lacks the myc epitope) was 0-20% (for each individual experiment), indicating that bead binding is selective for myc-tagged L1-CAM on the cell surface.

Bound beads were subject to a second pulse from the laser trap to test the resistance of the bead-myc-L1-CAM complexes to lateral displacement. The observed resistance to lateral movement can be interpreted as an indication of cytoskeletal attachment of bead-bound L1-CAM protein (Choquet et al. Cell 1997;88:39-48 and Felsenfeld et al. Nat Cell Biol 1999;1:200-206). At the highest concentration of antibody (0.37 mg antibody/ml beads), the majority of beads were resistant to lateral displacement (black bars; FIG. 1). The percentage of beads which were bound to the cell surface but not resistant to displacement (grey bars; FIG. 1) increased with decreasing antibody concentration. Moreover, bead rigidity on the cell surface was entirely abolished in the presence of 2 μM cytochalasin D, a concentration that completely suppresses F-actin in the periphery of ND-7 cells. These results suggest that extracellular crosslinking of L1-CAM by antibody regulates the association between L1-CAM and the actin cytoskeleton, consistent with results from studies of other L1 family members (Dubreuil et al. J Cell Biol 1996; 133:647-655).

Example 4

L1-CAM Engages in Three Distinct Classes of Movement on the Cell Surface,

Material and Methods

Cell culture and transfection: ND-7 cells (rat neuroblastoma/DRG hybrid cells) were cultured, plated, and transfected with the pMyc-L1-CAM expression construct as described in Example 3, supra.

Bead preparation: Beads were prepared as described in Example 3, supra. In all cases beads were coated with 9E10 at a concentration of 0.58 mg antibody /ml beads.

Video microscopy, laser tweezers, and data analysis: Video microscopy, laser tweezers and data analysis was performed as described in Example 3, supra. For analysis, all data sets were rotated to orient the cell with its leading edge facing left. Data sets for individual beads were then expressed as plotted X vs. Y coordinates (in Jim), as plotted X or Y coordinates (in μm) versus time (in seconds), and as plotted mean squared displacement (MSD) values (in $μm^2$) versus time (in seconds). The diffusion coefficients (D, in $μm^2$ per second "$μm^2s^{-1}$", and velocities (v, in μm per second "$μm\ s^{-1}$") were also calculated.

Results

Discussion

To analyze directly the behavior of L1-CAM on the upper surface of ND-7 cells, the movement of beads bound by antibody to cell-surface myc-L1-CAM was recorded. Beads coated with 9E10 bound to the cell surface and underwent rapid diffusion, retrograde movement, or remained stationary.

For diffusing beads, the trajectory lacked any detectible directed movement with respect to the leading edge. Similarly, mean square displacement for diffusing beads was linear with respect to time, consistent with diffusion in the absence of directed movement. The average rate of diffusion (0.082 $μm^2s^{-1}$; n=13) was consistent with the random movement of L1-CAM in the bilayer, largely in the absence of cytoskeletal or other interactions which would immobilize the protein(s) bound to the bead.

In contrast, beads bound to retrograde-moving L1-CAM showed little or no diffusion and instead moved away from the leading edge of the cell with a uniform velocity and direction. This directed movement occurred largely in the absence of movement parallel to the leading edge. Retrograde movement of L1 was often proceeded by a brief (<10 s), diffusive latency period. The velocity of retrograde-moving beads ranged from 0.6-2.2 μm/min, similar to the velocity of other cell-surface adhesion proteins,(see, e.g., Felsenfeld et al. Nature 1996;383:438-440 and Lambert et al. J Cell Biol 2002; 157:469-479). Moreover, retrograde movement of membrane ruffles on the surface of the lamella, often taken as a fiduciary marker of retrograde actin flow (Lin and Forscher. Neuron 1995;14:763-771), occurred at a similar rate to L1-bound beads. The velocity and direction of bead movement is, therefore, consistent with an interaction between L1 and treadmilling actin in the cytosol of the lamella.

Figure 2A:
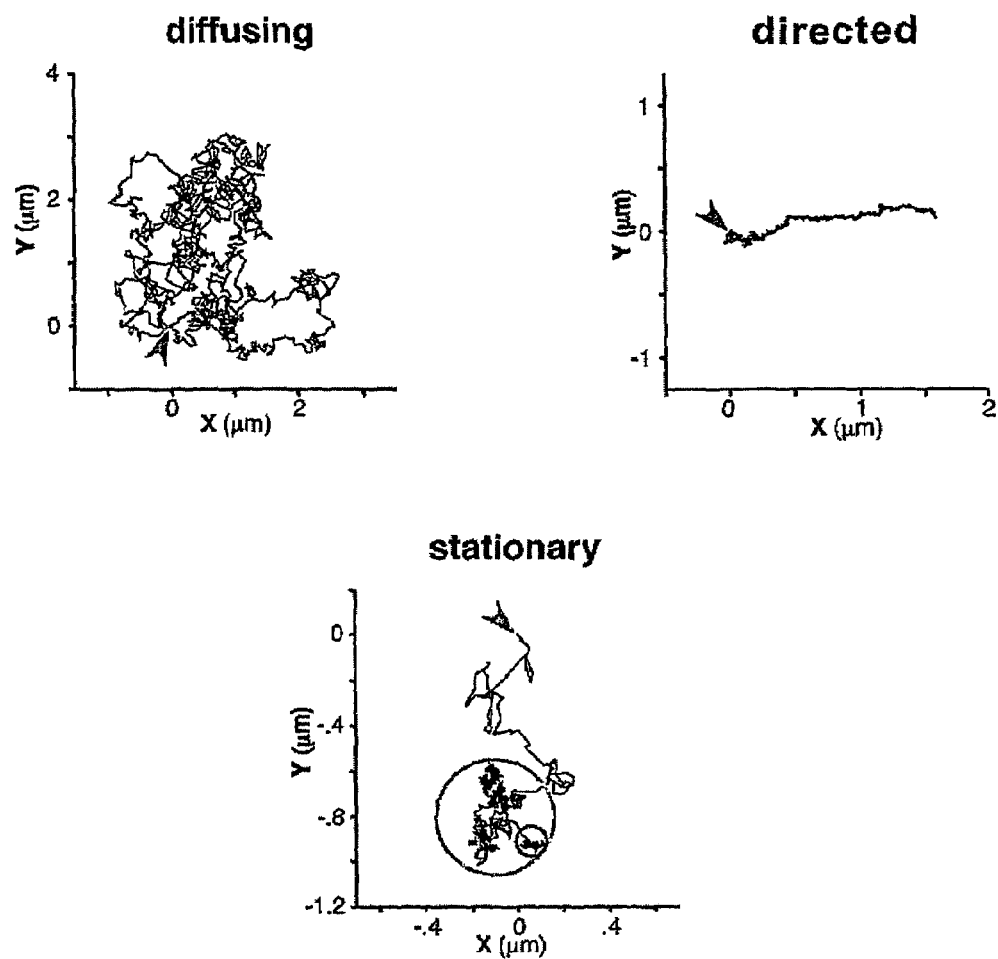
FIGS. 2(A and B) depicts data for the movement of anti-myc antibody coated beads bound to myc-L1-CAM on the surface of cultured rat neurons. "Diffusing" indicates a bead showing diffusion; "directed" indicates a bead showing directed retrograde movement; and "stationary" indicates a bead showing stationary behavior. All data sets were rotated to orient the cell with its leading edge facing the left edge of the page. 2A. Plots of Y coordinates (in μm) versus X coordinates (in μm). The origin of each bead is indicated by an arrow head. For "stationary", episodes of stationary behavior are indicated by a large and a small circle. 2B. Plots of X or Y coordinates ("X,Y" in μm) versus time (in seconds). Movement perpendicular ($\perp$, fine trace) and movement parallel ($\|$, thick trace) to the leading edge are represented by independent lines. For "stationary" the grey bar indicates the period of time used for calculations of mean squared displacement ("MSD" in μm for C.). C. Plots of mean squared displacement ("MSD" in μm) versus time (in seconds). The black line shows the measured MSD. For "stationary", the plotted MSD corresponds to the period of time indicated by the grey bar in B. "stationary".
Figure 2B:
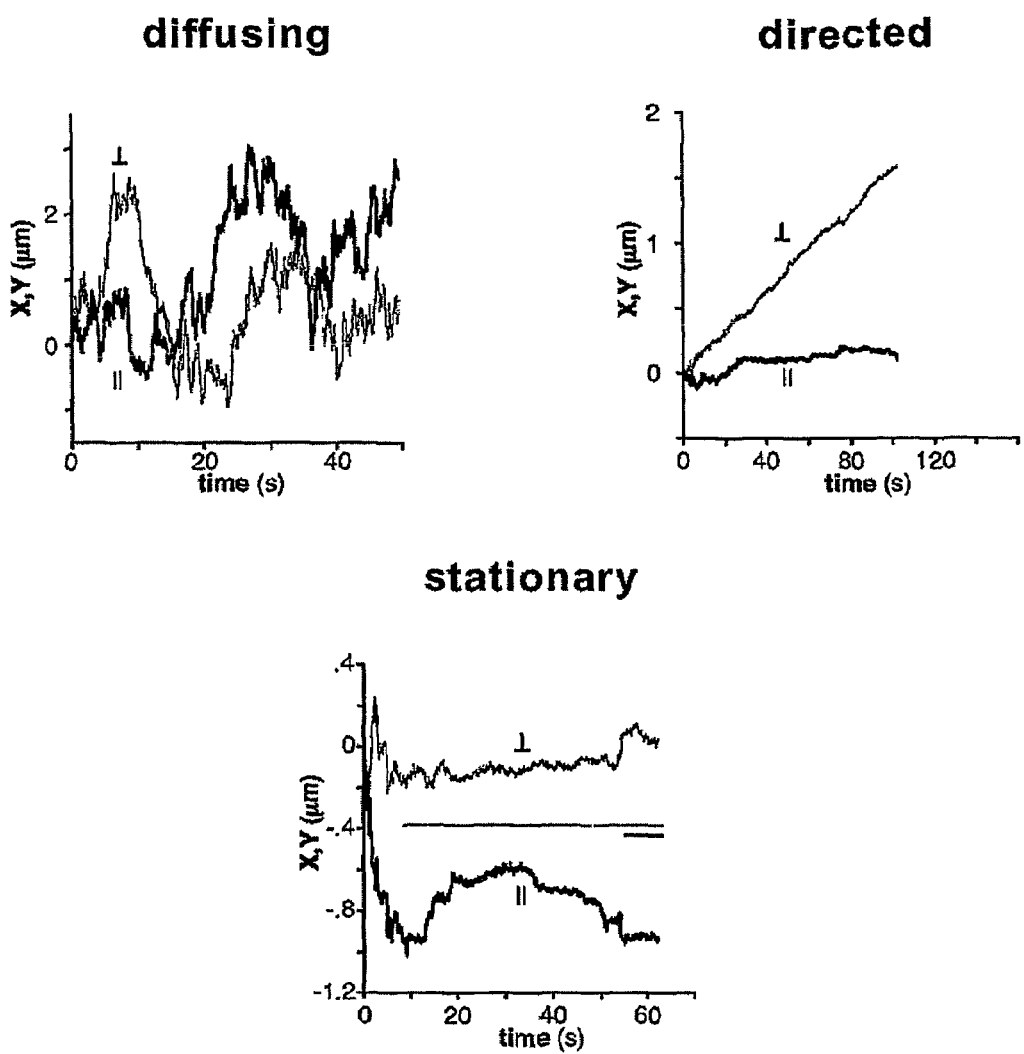
Figure 2C:
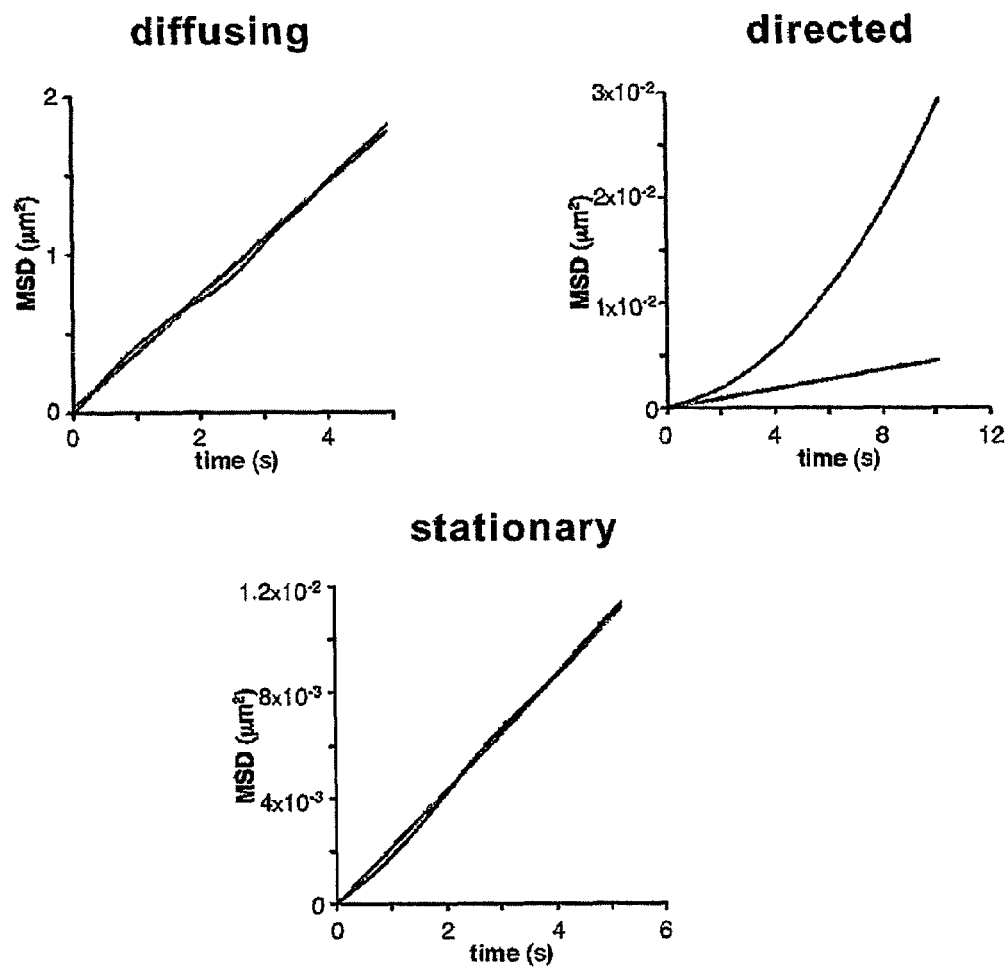

In addition to diffusion and retrograde movement, L1-CAM displayed a distinct stationary behavior characterized by a low rate of diffusion in the absence of detectible directed movement. The stationary behavior was transient and appeared to punctuate periods of diffusion. In some cases, beads underwent periods of mixed diffusion/stationary behavior during the latency period that preceded directed movement. Periods of stationary behavior appeared as plateaus with reduced noise in plots of displacement vs. time (e.g., seconds 55-60 in FIG. 2B, "stationary"), consistent with a decreased rate of diffusion.

Analysis of data sets with a high ratio of stationary behavior to diffusion (e.g., large circle in FIG. 2A, "stationary") revealed a reduced diffusion coefficient compared to freely diffusing particles with little or no directed component. In some cases, the MSD came to a plateau at longer time points, consistent with bounded diffusion, in which receptors diffuse freely over short distances and times but are corralled at greater distances. In cells expressing wild-type L1-CAM, 9E10-coated beads underwent retrograde transport on the cell surface in 68.9% of trials while 28.6% displayed stationary behavior (see Example 5, FIG. 3). Together, these results demonstrate that L1-CAM is capable of three distinct classes of behavior on the cell surface, including diffusion, retrograde movement, and stationary behavior in the absence of directed movement. These distinct behaviors are consistent with interactions between L1-CAM and both dynamic and static components of the cytoskeleton.

Example 5

Ankyrin Binding Mediates L1-CAM Stationary Behavior

Material and Methods

Cell culture and transfection: ND-7 cells (rat neuroblastoma/DRG hybrid cells) were plated and transfected with pMyc-L1-CAM, pMyc-L1-CAM-YF, pMyc-L1-CAM-YH, or pMyc-L1-CAM-STOP expression constructs as described in Example 3, supra.

In some instances, ND-7 cells transfected with pMyc-L1-CAM were treated with the cytoskeletal inhibitor cytochalasin D (2 µM; Sigma) or nocadazole (1 µM; Sigma). For these experiments treatment with DMSO (0.01%) vehicle alone served as the negative control.

In some instances, ND-7 cells transfected with pMyc-L1-CAM were treated with neural growth factor (NGF) to stimulate phosphorylation of tyrosine 1229 (Y1229) of the L1-CAM cytoplasmic domain, and thereby inhibit ankyrin binding. For these assays, cells were treated with 100 ng/mL NGF (Gibco) for 1 hour prior to the assay.

Bead preparation: Beads were prepared as described in Example 3, supra. In all cases beads were-coated with 9E10 at a concentration of 0.58 mg antibody/ml beads.

Video microscopy, laser tweezers and data analysis: Video microscopy, laser tweezers and data analysis was performed as described in Example 3, supra. For analysis, all data sets were rotated to orient the cell with its leading edge facing left. Data sets for individual beads were then expressed as plotted Y vs. X coordinates (in µm), as plotted X or Y coordinates (in µm) versus time (in seconds), and as plotted mean squared displacement (MSD) values (in $\mu m^2$) versus time (in seconds). Based on these analyses, beads were classified as showing diffusion, directed retrograde movement, or stationary behavior. The results are reported as the % of trials showing each behavior, where % of trials is the number of beads displaying each behavior/total number of trials.

Results and Discussion

Figure 3A:
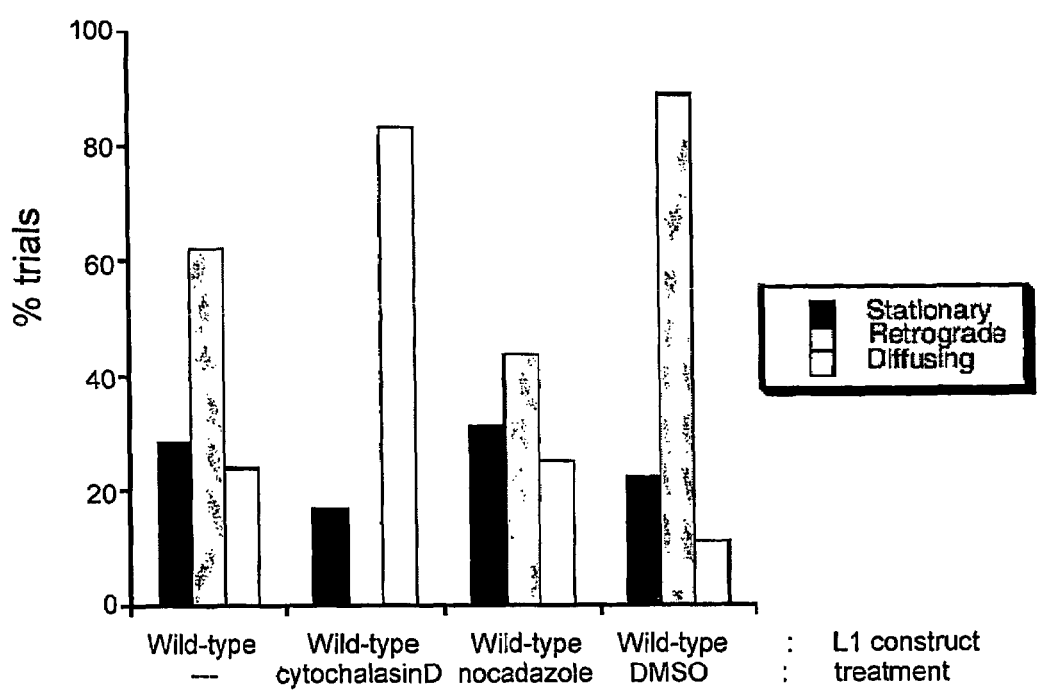
FIGS. 3(A and B) depict bar graphs showing the percentage of trials (% trials) showing stationary (black bars), retrograde movement (grey bars), or diffusing (white bars) behavior of L1-CAM-bound beads on cultured neuronal cells expressing myc-L1-CAM ("Wild-type"), myc-L1-CAM-STOP ("Stop"), myc-L1-CAM-YF ("YF"), or myc-L1-CAM-YH ("YH") and subjected to treatment with cytochalasinD, nocadazole, DMSO, or NGF or left untreated ("—"). The data are representative of results from three independent experiments.

To identify the mechanism underlying the directed and stationary behavior of L1-CAM on the cell surface, the movement of L1-CAM in the presence of various cytoskeletal inhibitors was observed (FIG. 3A). In ND-7 cells expressing wild-type L1-CAM, 28.6% of trials were stationary, 61.9% retrograde and 9.5% diff-used to the exclusion of other identifiable behavior (n=21). Cytochalasin D treatment (2 µM) eliminated retrograde movement (stationary 16.7%, retrograde 0%, diffusing 83.3%; n=12). In contrast, nocadazole treatment (1 µM) inhibited retrograde movement slightly while leaving stationary behavior and diffusion unaffected (stationary 31.25%; retrograde 43.75%; diffusing 25%; n=16). Treatment with DMSO alone at the same concentration used to dilute cytochalasin D and nocadazole caused a slight increase in retrograde movement (stationary 22.2%, retrograde 88.8%; diffusing 11.1%; n=9).

Thus, Cytochalasin D, at a concentration that completely suppresses F-actin in the periphery of ND-7 cells (2 µM), abolishes the retrograde movement of L1-CAM (n=12, p<0.01). In contrast, stationary behavior was still observed in a small percentage of trials, suggesting that this behavior is either actin independent or mediated by non-dynamnic pools of actin that are less sensitive to cytochalasin D treatment. In contrast, both retrograde movement and stationary behavior were observed in the presence of nocadazole (1 µM, a concentration that blocks microtubule polymerization in ND-7), although the frequency of retrograde movement was diminished as compared to untreated control cells (n=16, p<0.22). Treatment with DMSO alone at the same concentration used in the dilution of cytochalasin D and nocadazole resulted in a slight increase in retrograde movement, perhaps due to changes in membrane fluidity. These results suggest that retrograde movement of cell-surface L1-CAM is actin-mediated, although microtubules may also contribute indirectly to this process.

To determine whether the low diffusive states of L1-CAM on the cell surface are mediated directly by the L1-CAM cytoplasmic tail, a truncation mutant of L1-CAM was generated that interrupts the cytoplasmic tail with a stop mutation 4 amino acids after the predicted transmembrane domain. Beads bound to truncated L1-CAM on the cell surface diffused in 100% of trials (FIG. 3B; n=17, p<0.01), indicating that both retrograde movement and stationary behavior depend on interactions between the L1-CAM cytoplasmic tail and the cytoskeleton.

To examine directly the role of L1-CAM cytoskeleton interactions in L1-CAM movement on the upper surface, a series of point mutations was introduced into the region of the L1-CAM cytoplasmic tail that has been implicated in ankyrin binding. Mutant constructs were generated encoding single amino acid substitutions for tyrosine 1229 to either phenylalanine (myc-L1-CAM-YF), a mutation which induces constitutive ankyrin binding in other vertebrate L1 family members (Garver et al. J Cell Biol 1997;137:703-714 and Tuvia et al. J Cell Biol 1999;147:995-1008); or to histidine (myc-L1-CAM-YH) a mutation which inhibits ankyrin binding (Garver et al., supra; Tuvia et al., supra; and Needham et al. J Neurosci 2001;21:1490-1500). Each of these constructs was expressed in ND-7 cells and displayed cell-surface distribution comparable to that seen for wild-type myc-L1-CAM expressed in the same background (see Example 2).

Figure 3B:
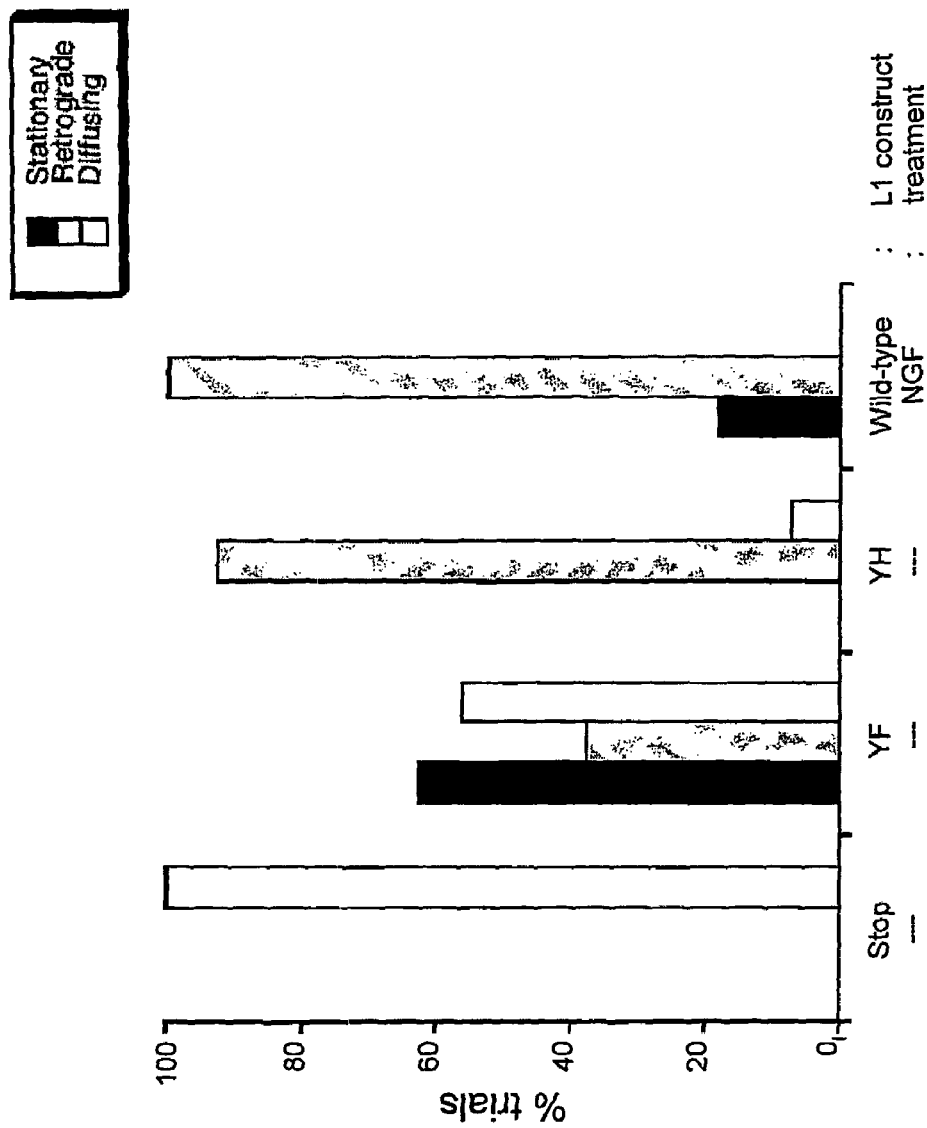

In culture, 9E10 beads placed on the upper surface of the cell with a laser trap bound with a frequency similar to that seen in cells expressing wild-type myc-tagged L1-CAM. In cells expressing the YF mutant L1-CAM (YF), 62.5% of trials were stationary and 37.5% were retrograde-moving (0% diffused; n=16; FIG. 3B). In cells expressing the YH mutant of L1-CAM (YH), 0% were stationary, 92.9% were retrograde-moving and 7.1% diffusing (n=14). Finally, in cells expressing wild-type L1-CAM treated with NGF to stimulate phosphorylation of Y1229, inhibiting ankyrin binding, 18.2% of trials displayed some form of stationary behavior while 100% underwent retrograde transport on the cell surface (0%. diffusing; n=11).

Thus, like wild-type L1-CAM, L1-CAM-YF displayed a combination of diffusive, retrograde-moving and static behaviors. However, the ratio of these behaviors was different from that of the wild-type receptor, showing an increase in the percentage of trials exhibiting stationary behavior (62.5%) with a commensurate decrease in retrograde movement (37.5%; FIG. 3B; n=16, p<0.01). In contrast, beads bound to the L1-CAM-YH mutant showed a large increase in the percentage of trials undergoing retrograde movement (92.9%) and a complete loss of stationary behavior (FIG. 3B; n=14, p<0.011). These results suggest that L1-CAM stationary behavior is mediated by ankyrin binding, whereas the retrograde movement of L1-CAM on the cell surface is ankyrin-independent.

Finally, in ND-7 cells expressing myc-L1-CAM that were treated with NGF to stimulate phosphorylation of L1-CAM tyrosine 1229 (thereby inhibiting ankyrin binding), only 18.2% of trials displayed some form of stationary behavior and 0% were diffusing, while 100% underwent retrograde transport on the cell surface (n=11; FIG. 3). Note that the combined total exceeding 100% reflects the fact that, for some trials, beads exhibit both forms of behavior over the course of observation.

These results indicate that L1-CAM stationary behavior is mediated by ankyrin binding, whereas the retrograde movement of L1 on the cell surface is ankyrin-independent. Thus, these results indicate that L1-CAM-ankyrin interactions mediate the stationary behavior of cell-surface L1-CAM. Moreover, the increase in the percentage of beads undergoing retrograde movement in conditions that perturb ankyrin binding indicates that ankyrin binding negatively modulates L1-CAM-mediated traction-force generation.

Example 6

Growth Factor Treatment Inhibits AnkyrinB Binding to L1-CAM

Material and Methods

Cell culture aid transfection: Human kidney 293 cells were cultured in DMEM medium (Gibco) supplemented with penicillin, streptomycin, L-glutamine, and 10% fetal bovine serum (Hyclone). The pMyc-L1-CAM or pL1-CAM-GFP expression constructs were transfected into cultured human kidney 293 cells using Lipofectamine plus (Invitrogen) according to manufacturer instructions. Cells were cultured for 24-48 hours and then used, or cultured continuously in the presence of 0.5 µg.mL G418 (Gibco) to select for stably transfected cells lines, to generate stable pooled lines of L1-CAM-expressing cells.

In some instances, transfected 293 cells were treated with neural growth factor (NGF) or epidermal growth factor (EGF) to stimulate phosphorylation of tyrosine 1229 (Y1229) of the L1-CAM cytoplasmic domain, and thereby inhibit ankyrin binding. In these cases, cells were treated with 50 ng/mL EGF (Gibco) or 100 ng/mL NGF (Gibco) for 1 hour prior to the assay.

Immunohistochemistry: Transfected cells were fixed for 10 minutes using 1% paraformaldehyde in PHEM (60 mM PIPES, 25 mM HEPES, 10 mM EGTA, and 2 mM $MgCl_2$). The cells were permeabilized for 6 minutes in PHEM containing 0.1% Triton-X100 and 0.05 mM glycine. Fixed and permeabilized cells were blocked using 0.05 mM glycine, 1% BSA and 1% normal donkey serum (Jackson Immunochernicals) in PHEM. All subsequent incubations were carried out in 0.05 mM glycine in PHEM.

Ankyrin and L1-CAM were detected by indirect immunofluorescence in double-labeled confocal sections through cell aggregates to permit the visualization of L1 and ankyrinB at the cell membrane. Expression of myc-L1-CAM was detected using a polyclonal anti-L1-CAM rabbit antibody. This polyclonal antiserum was generated using standard techniques well established in the art (see, for example Harlow and Lane. *Antibodies: A Laboratory Manual* (Cold Spring Harbor Laboratory Press: 1988)), by immunizing rabbits with purified mouse L1-CAM protein (Genbank Accession number AAF22153). This antiserum detects both mouse and rat L1-CAM proteins. (Note the 293 cells do not express endogenous L1-CAM, so that this antibody will only detect myc-L1-CAM). Ankyrin was detected using a monoclonal anti-ankyrinB mouse antibody (BD PharMingen). Anti-rabbit and anti-mouse secondary antibodies conjugated to Cy3 or Cy5 (Jackson Immunochemicals) were provided as cross-adsorbed against other species to ensure minimal cross reactivity to other species.

Laser scanning confocal micrographs (Olympus) were collected at a plane intersecting the cell-cell junctions of transfected cells. Excitation was accomplished using single lines from either an argon or a krypton laser (488 nm for GFP or green dyes, 568 nm for Cy3; 647 nm for Cy5). Emission filters used were 510 nm long pass for GFP; 605 nm band pass for Cy3, 100 nm band pass for Cy5. Control images collected by exciting fluorophores with the inappropriate laser line revealed no detectible crosstalk between channels (i.e., each excitation wavelength was specific for its target secondary antibody).

Quantification of ankyrin immunolocalization: Confocal micrographs were then used to quantify the degree of ankyrin localization to the cell membrane of myc-L1-CAM expressing cells. Images were analyzed using ImageJ (NIH) under Macintosh OSX. The method for quantifying ankyrinB localization to the membrane uses densitometry of a line scan perpendicular to and crossing a cell-cell junction. Densitometry was carried out using a 5 pixel-wide line scan normal to the interface between two L1-positive cells.

The densitometry intensity profile of the scanned line was used to determine a minimum ankyrinB signal for comparison to the value of the ankyrinB signal at the point where the maximum signal in the L1-CAM channel occurs. Signal maxima for ankyrin staining at the junction between cells was determined at the position of the maximal L1-CAM staining to ensure that membrane rather that juxta-membrane staining was being quantified. Minima were determined from the regions of the line overlapping the cytoplasm of either of the two cells. These minimum and maximum AnkyrinB signal values were the used to calculate the membrane localization index value using the equation index=$(AnkyrinB_{max} - AnkyrinB_{min})/AnkyrinB_{min}$. Index values were averaged for experimental cells (NGF or EGF treated) and for control cells (not NGF or EGF treated). The average values for control cells were standardized to 1 unit, and the values for experimental cells were normalized with respect to the control values.

Results

To further show that L1-CAM stationary behavior is mediated by ankyrin binding, the cellular localization of L1-CAM and ankyrin proteins following growth factor treatment of expressing cells was examined. The L1-CAM-dependent recruitment of ankyrinB to the cytoplasmic membrane has been used in the past as an indicator of L1-CAM-ankyrin interactions in intact cells (Zhang et al. J Biol Chem 1998; 273:30785-30794 and Needham et al. J Neurosci 2001;21: 1490-1500). Furthermore, it has been reported that tyrosine phosphorylation of L1-CAM family members at the FIGQY motif of the cytoplasmic tail is modulated by activation of a variety of membrane-linked tyrosine kinase receptors, including receptors for NGF, fibroblast growth factor (FGF), and epidermal growth factor (EGF) (Garver et al. J Cell Biol 1997;137:703-714) and by the Eph kinase Cek5 (Zisch et al, 1997).

Constructs encoding myc-tagged L1-CAM (pMyc-L1-CAM) or C-terminally GFP-tagged L1-CAM (pL1-CAM-GFP) were transfected into human kidney 293 cells. These cells were chosen for this experiment based upon their low level of background binding of ankyrin to the membrane (Zhang et al. J Biol Chem 1998;273:30785-30794).

Figure 4A:
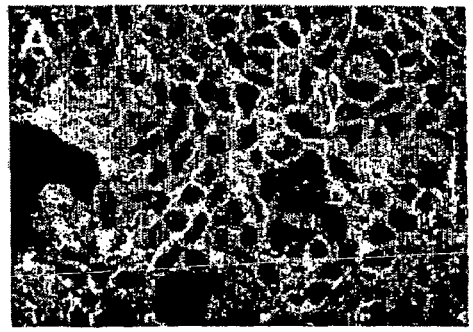
FIGS. 4(A-E) contains data to show that growth factor treatment inhibits ankyrin binding to L1-CAM. The pMyc-L1-CAM expression construct was transfected into 293 cells that were not treated with EGF and into cells that were treated with EGF. 4(A-D). AnkyrinB and L1-CAM proteins were detected by indirect immuno-fluorescence in double-labeled confocal sections through cell aggregates to permit the visualization of L1-CAM and ankyrinB proteins at the cell membrane. 4A. Ankyrin staining in cells that were not treated with EGF. 4B. Ankyrin staining in cells that were treated with EGF. 4C. L1-CAM staining in cells that were not treated with EGF. 4D. L1-CAM staining in cells that were treated with EGF. 4E. A bar graph depicts results from direct quantification of ankyrin B co-localization with L1-CAM at the membrane in the cells that had not been treated with EGF ("Control") and in cells that had been treated with EGF ("EGF"). Error bars: +/− standard deviation. 4F. A confocal micrograph illustrates the method for quantifying ankyrinB localization to the membrane using densitometry of a line scan. AnkyrinB staining is shown. The white line perpendicular to the cell-cell junction indicates the scanned line. The inset contains the intensity profile of the indicated scanned line.
Figure 4B:
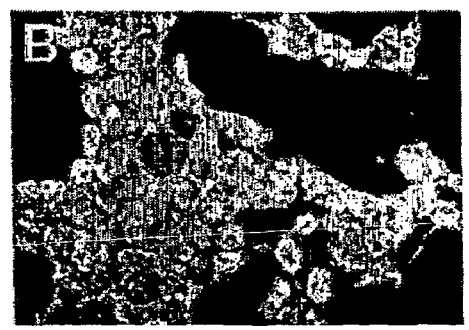
Figure 4C:
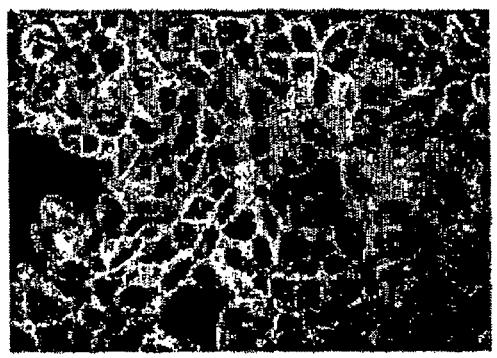
Figure 4D:
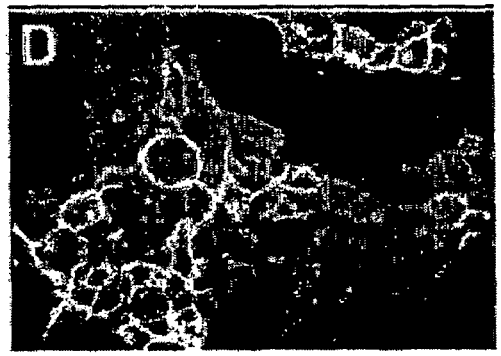

Ankyrin and L1-CAM were detected by indirect immunofluorescence in double-labeled confocal sections through cell aggregates to permit the visualization of L1-CAM and ankyrinB at the cell membrane. Combined micrographs indicated clear co-distribution of ankyrin (FIG. 4A) and L1-CAM (FIG. 4C) signals at the cell membrane in the absence of growth factors. In contrast, in the presence of EGF, L1-CAM staining remains at the membrane (FIG. 4D), but ankyrinB staining appears as a uniform distribution throughout the cytosol (FIG. 4B).

Figure 4E:
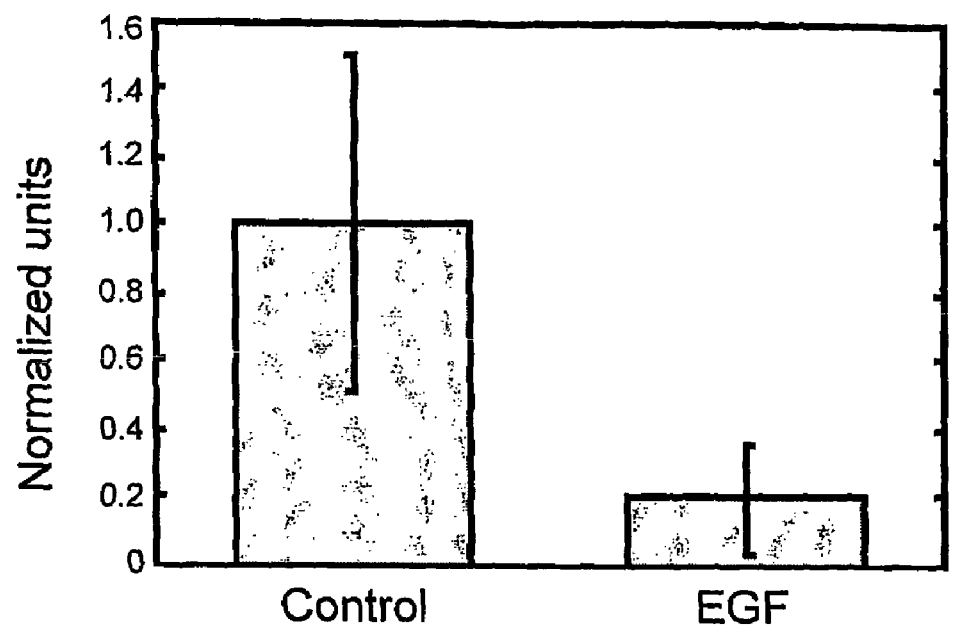
Figure 4F:
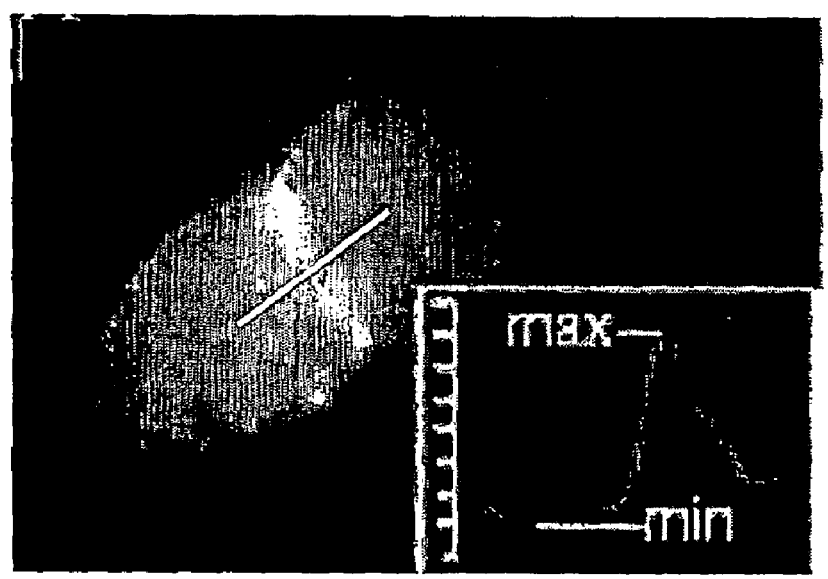

Direct quantification of the ankyrin signal shows a significant reduction of ankyrin B colocalization with L1-CAM at the cell membrane following treatment with EGF ($p<0.01$; FIG. 4E). The method for quantifying ankyrinB localization to the membrane uses densitometry of a line scan across a cell-cell junction where L1 is expressed (see FIG. 4F, showing ankyrinB signal and scanned line). The resulting ankyrin intensity profile from the scanned line (FIG. 4F inset) is used to determine a minimum signal for comparison to the value of the ankyrinB signal at the point where the maximum signal in the L1 channel occurs.

Similar results were obtained using transfected ND-7 cells treated with NGF, suggesting that these cells, derived from primary sensory neurons, have maintained their sensitivity to NGF.

Discussion

In transfected 293 cells, ankyrin was recruited to the membrane in an L1-CAM dependent manner. Treatment of these cells with EGF or NGF inhibited ankyrin membrane localization, consistent with a phosphorylation-dependent inhibition of L1-CAM-ankyrin binding. Measurement of ankyrin immunolocalization along a line drawn across the junction of L1-positive cells demonstrated a quantifiable and significant change in ankyrin-membrane association following EGF or NGF treatment.

As discussed in Example 5, treatment of ND-7 cells expressing myc-tagged L1-CAM with NGF caused a shift in the ratio of stationary to retrograde-moving beads similar to that seen in cells expressing L1-CAM-YH (18.2% stationary, 100% retrograde; FIG. 3). The observed correlation between the shift to retrograde movement and the disruption of L1-CAM-ankyrin cell membrane association upon NGF treatment indicates that ankyrin binding negatively modulates L1-CAM-mediated traction-force generation.

Example 7

Peptides Derived from the L1-CAM Tail Inhibit Ankyrin Binding to L1-CAM, and Inhibit L1-CAM Stationary Behavior While Promoting L1-CAM Retrograde Movement Material and Methods Design and synthesis of inhibitory peptides: An inhibitory peptide, AP-YF, of amino acid sequence RQIKINWQNRRMKWKKQFNEDGSFIGQF (SEQ ID NO: 3) was generated as a fusion between the 16 amino acid penetratin domain of antennapedia (in bold) and the ankyrin binding domain amino acid sequence of L1-CAM in which the carboxy-terminal tyrosine has been changed to phenylalanine (underlined). A control peptide, AP-scramble, of amino acid sequence RQIKIWFQNRRMKWKKFQGIFSGDENFQ (SEQ ID NO: 23) was generated as a fusion between the 16 amino acid penetratin domain of antennapedia (in bold) and amino acid sequence that is the reverse of the L1-CAM ankyrin binding domain amino acid sequence (underlined). Both the inhibitory (AP-YF) and control (AP-scramble) peptides included an amino-terminal biotin moiety.

Inhibitory (AP-YF) and control (AP-scramble) peptides were synthesized using ABI 431 Peptide employing FastMoc Chemistry (Tufts University Core Facility, peptide synthesis service). N-terminal biotin was added during peptide synthesis. The synthesized peptides were purified by high pressure liquid chromatography (HPLC), and their purity determined to be >97% using mass spectrometry (Tufts University Core Facility, peptide synthesis service). The purified peptides were dissolved in Hank's Balanced Salt Solution (HBSS; Gibco) at 1 mg/ml and diluted into cell culture medium at a final concentration of 1.4 µg/ml.

Cell culture and transfection: For the ankyrin recruitment assays, human kidney 293 cells were cultured and transfected with pMyc-L1-CAM or pL1-CAM-GFP expression constructs as described in Example 6, supra. For the L1-CAM diffusion behavior assays, ND-7 cells (rat neuroblastoma/DRG hybrid cells) were plated and transfected with the pMyc-L1-CAM or pMyc-L1-CAM-YH expression constructs as described in Example 3, supra. In both cases, cells were cultured for 16-32 hours prior to assay, and treated with a final concentration of 1.4 µg/ml peptide for 30 minutes prior to the start of the assay.

Ankyrin recruitment assays: For the ankyrin recruitment assays, Immunohistochemistry and Quantification of ankyrin immunolocalization were performed on the transfected 293 cells as described in Example 6, supra.

L1-CAM diffusion behavior assays: For the L1-CAM diffusion behavior assays, Bead preparation and Video microscopy, laser tweezers and data analysis were performed on the transfected ND-7 cells as described in Example 3, supra. In addition, the mean velocity of movement (in nm per second "$nm\ s^{-1}$" was calculated for beads showing directed retrograde movement.

Results and Discussion

To further examine the role of ankyrin binding in the directed movement of L1-CAM, peptides to inhibit L1-CAM-ankyrin interactions in live cells were designed. The inhibitory peptide (RQIKIWFQNRRMKWKKQFNEDGSFIGQF; SEQ ID NO: 3), called AP-YF, is a fusion between the membrane permeable penetratin domain of antennapedia and the ankyrin-binding region of the L1-CAM cytoplasmic tail. The penetratin domain amino acid sequence (RQIKIWFQNRRMKWKK; SEQ ID NO: 6) mediates translocation of the peptide across the plasma membrane and into the cytoplasm of cells (see, e.g., Derossi et al. Trends Cell Biol 1998;8:84-87). The inhibitory domain amino acid sequence (QFNEDGSFIGQF; SEQ ID NO: 2) was derived from the 12 amino acid conserved region of the L1-CAM tail that has been shown to be required for ankyrin binding to other L1-CAM family members (Zhang et al. J Biol Chem 1998;273:30785-30794) including a Y to F substitution to mimic the dephosphorylated, ankyrin-binding protein. Inhibitory peptide activity on L1-CAM expressing-cells was compared to that of a control peptide (RQIKIWFQNRRMKWKKFQGIFSGDENFQ; SEQ ID NO: 23), called AP-Scramble, in which the sequence of the inhibitory domain was reversed.

Figure 5A:
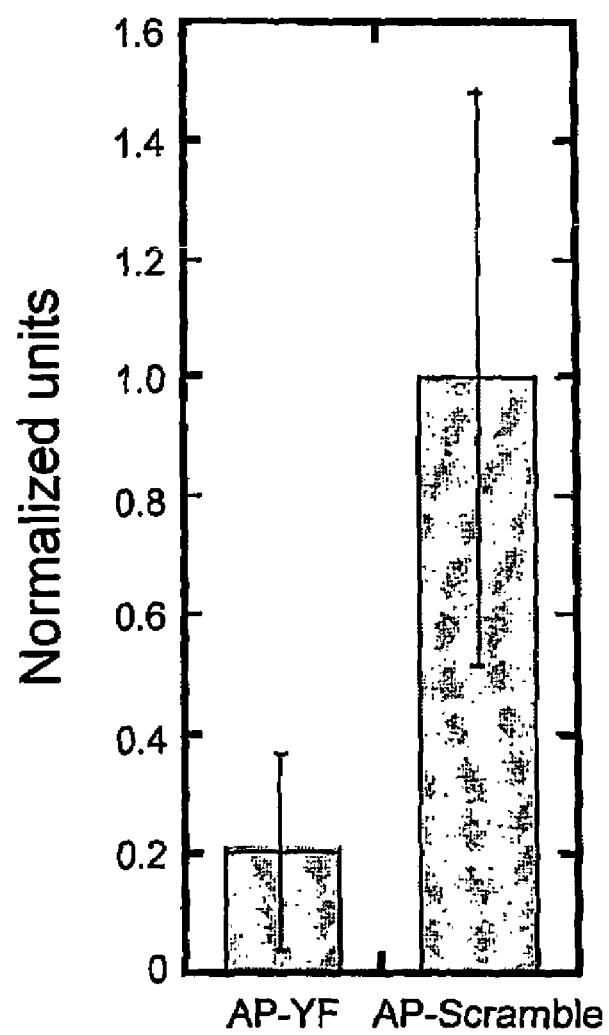
FIGS. 5(A and B) depicts bar graphs of data showing that the AP-YF peptide inhibits L1-CAM-ankyrin interactions and promotes both the frequency and velocity of L1-CAM retrograde movement. 5A. A bar graph depicts results from direct quantification of ankyrinB co-localization with L1-CAM at the membrane (given in normalized units of ankyrin staining intensity) in cells that had been treated with the inhibitory peptide ("AP-YF") and in cells that had been treated with the control peptide ("AP-Scramble"). Error bars: +/− standard deviation. 5B. A bar graph shows the percentage of trials showing stationary behavior (grey bars), retrograde directed movement (black bars), or diffusing behavior (white bars) of L1-CAM-bound beads on cultured neuronal cells expressing myc-L1-CAM which were untreated ("Control"), treated with the AP-YF peptide ("AP-YF"), or treated with the AP-Scramble peptide ("AP-Scramble"). 5C. A bar graph shows the mean velocity (in nm per second, "nm s$^{-1}$") of L1-CAM-bound beads showing directed movement across cultured rat neuronal cells. The cells were transfected with pMyc-L1-CAM ("Wild-type") and either treated with the AP-YF peptide ("AP-YF"), treated with the AP-Scramble peptide ("AP-Scramble"), or untreated ("---"). Other cells were transfected with pMyc-L1-CAM-YH ("YH") and left untreated ("---"). Error bars: +/− standard deviation.

To test the function of the AP-YF, its capacity to inhibit L1-CAM-mediated recruitment of ankyrin to the cell membrane in adherent, L1-CAM-expressing 293 cells was examined (as described in Example 6, supra). In membrane recruitment assays which directly quantified ankyrin co-localization with L1-CAM at the cell membrane of transfected 293 cells in the presence of AP-YF versus AP-Scrambled peptides, the AP-YF peptide significantly ($p<0.0002$) inhibited L1-CAM-ankyrin interactions (FIG. 5A). Thus, in the presence of peptide AP-YF, ankyrinB was almost entirely absent from sites of cell-cell contact of L1-CAM expressing cells. In contrast, in the absence of peptide or in the presence of the control AP-Scrambled peptide, ankyrinB appeared at the cell membrane where L1 was expressed. Thus, the control peptide (AP-Scramble) had no detectable effects on L1-CAM-ankyrin interactions. These results indicate that the AP-YF peptide is an effective inhibitor of L1-CAM-ankyrin interactions in live cells.

Figure 5B:
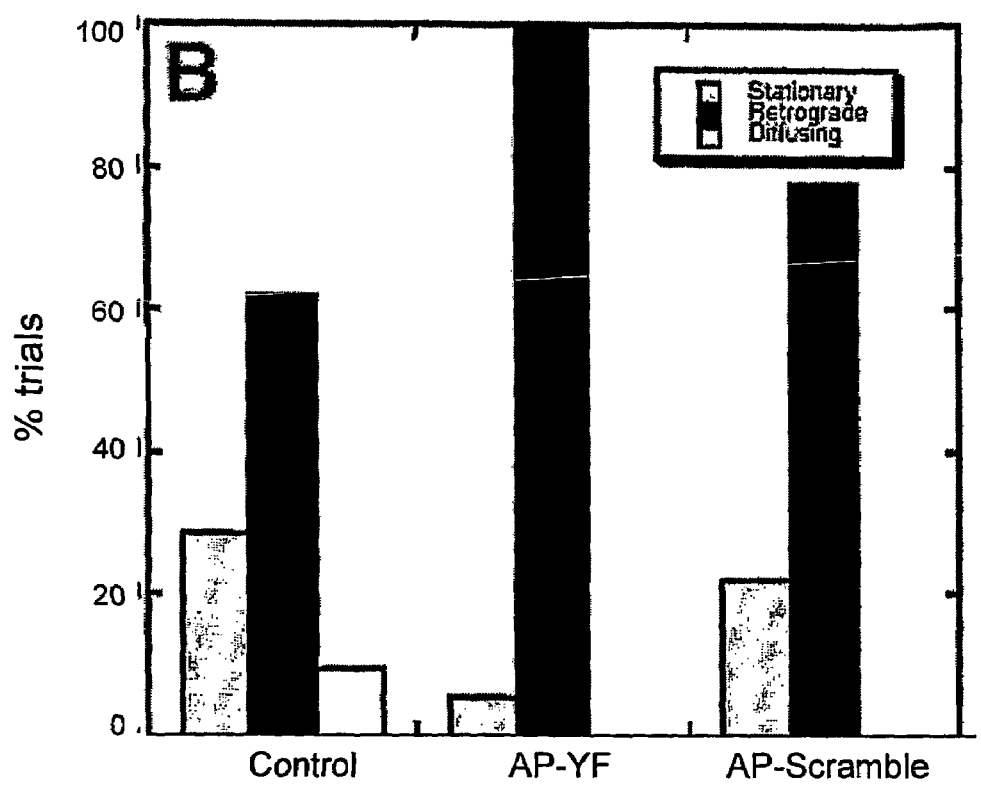

In assays to determine the effect of the AP-YF peptide in L1-CAM movement in transfected ND-7 cells, quantification of bead movement showed that the AP-YF peptide reduced the percentage of beads showing stationary behavior when bound to cell-surface myc-L1-CAM, with an accompanying increase in the percentage of trials undergoing retrograde movement (FIG. 5B, $n=18$, $p<0.05$). Cells treated with the control AP-Scramble peptide behaved in a manner similar to untreated cells (FIG. 5B, $n=9$, $p>0.05$). These results confirm that inhibition of L1-CAM-ankyrin binding by the peptide AP-YF selectively inhibits the low diffusion, stationary state of L1-CAM on the cell surface. This observation indicates that ankyrin mediates L1-CAM interactions with stationary components of the cytoskeleton. Moreover, the increase in the percentage of trials undergoing retrograde movement on the cell surface following inhibition of L1-CAM-ankyrin binding indicates that ankyrin binding inhibits the directed movement of L1-CAM on the cell surface.

Figure 5C:
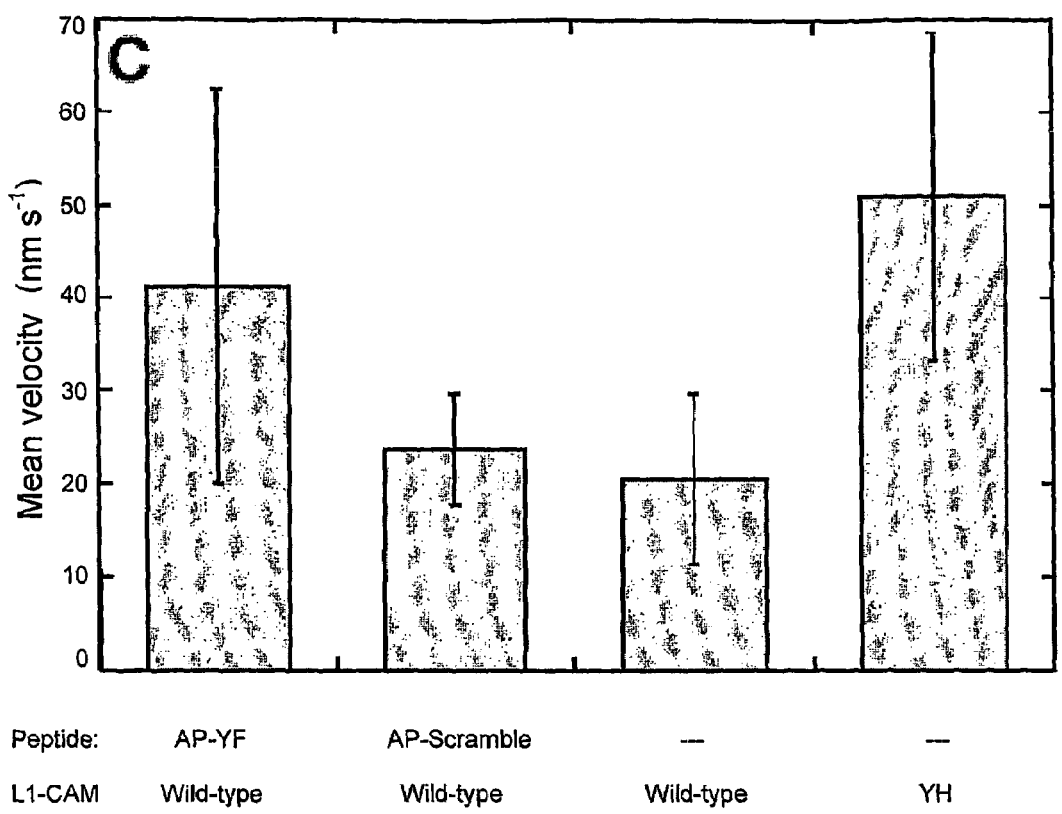

The velocity of bead movement for trials showing retrograde translocation of L1-CAM-bound beads on the cell surface of cells treated with the of AP-YF or AP-Scramble peptides was then quantified. Myc-L1-CAM expressing cells cultured in the presence of the inhibitory AP-YF peptide showed on average a 2-fold increase in the velocity of L1-CAM directed movement on the cell surface as compared to cells treated with control peptide (FIG. 5C; $p<0.009$) or untreated cells ($p<0.003$). The AP-Scrambled peptide had no significant effect on bead velocity compared to untreated controls. Similarly, cells expressing myc-L1-CAM-YH showed a significant increase in the rate of directed bead movement on the cell surface as compared to untreated cells expressing myc-L1-CAM ($p<10^{-4}$). These changes in mean velocity do not merely reflect the decrease in the percentage of stationary beads, as beads with no mean velocity were not included in the calculated average velocity. Together, these results confirm the role of L1-CAM-ankyrin interactions in the regulation of L1-CAM directed movement on the cell surface, and indicate that L1-CAM-mediated traction force generation may be promoted by inhibiting the binding of ankyrin to L1-CAM.

Example 8

Peptide Inhibitors of Ankyrin Binding to L1-CAM Stimulate L1-CAM-mediated Neurite Outgrowth Materials and Methods For neurite outgrowth assays, chick Ng-CAM was purified from chick brain using an antibody-based affinity column according to techniques well known in the art. The anti-Ng-CAM antibody was antibody 8D9 (Developmental Studies Hybridoma Bank, University of Iowa). Then purified chick Ng-CAM (50 µg/ml) or mouse laminin (Invitrogen, 100 µg/ml) was spotted on a 35 mm plastic culture dish at room temperature (RT) for 1 hr. After washing with PBS, the plastic surface was blocked with 1% Bovine Serum Albumin in phosphate buffered saline (13SA/PBS) at RT. Negative control dishes were coated with 1% Bovine Serum Albumin in phosphate buffered saline (BSA/PBS) at RT.

Cerebellar cells were prepared from postnatal day 4 (P4) mouse by trypsinization followed by trituration. Postnatal day 4 (P4) mouse cerebellum was minced in Calcium/Magnesium-free phosphate buffer (Ca/Mg-free PBS). Minced cerebellum was then treated with 0.05% Trypsin (Gibco) in Ca/Mg-free PBS for 15 minutes at 37° C. Trypsinization was halted by addition of 10% Fetal Calf Serum (Hyclone). Trypsinized cells were then triturated 5 times with a fire-polished Pasteur pipette to dissociate the cells. The remaining cell clumps were allowed to settle, and the suspended cells were plated and maintained for use in the neurite outgrowth assays.

Cultured cerebellar cells were resuspended in BME/B-27 medium (BME medium plus B-27 supplement, both from Gibco) supplemented with penicillin/streptomycin (Gibco) to a cell density of $5\times10^5$ cells/ml. Then 250 µl of this cell suspension was plated on the dishes. AP-YF or AP-Scramble peptides dissolved in Hank's Balanced Salt Solution (Gibco) were added to the plated cells at final concentration of 30 µg/ml. Cultures were incubated at 37° C. for 24 hrs in 5% $CO_2$. These cultures were fixed with 4% paraformaldehyde and images were collected on a Zeiss Axiovert 100TV microscope using a 100× plan neofluor objective. Neurite outgrowth measurements were performed using NIH image software. Data was expressed as average neurite length in µm (+/– standard deviation). P-values were determined using Student's t-test analysis. Microsoft Excel was used to plot the data as % neurites of length greater than Xpm versus neurite length X (in µm).

Results and Discussion

To demonstrate that regulation of ankyrin binding to L1-CAM may be used in vivo to differentially regulate the adhesion and migration of growing neurons, mouse cerebellar granular neurons were cultured in the presence of either inhibitory AP-YF or control AP-Scramble peptides. Mouse cerebellar granular neurons use cell-surface L1-CAM as the primary receptor for substrate-bound L1-CAM ligands (Dahme et al. Nature Genetics 1997; 17:346-349), and therefore may be used to directly test L1-CAM function in neurite extension.

Mouse cerebellar granular neurons were plated on tissue culture dishes coated with chick Ng-CAM, a chick homolog of L1-CAM, or on tissue culture dishes coated with mouse laminin. The Ng-CAM substrate interacts with cell-surface L1-CAM, while laminin substrate interacts with cell surface integrins and therefore serves as the negative control. These cultures were treated with either AP-YF or AP-Scramble peptides. After 24 hours of culture, the neurons were fixed and neurite outgrowth lengths w-ere measured by NIH image software degree (in µm).

Neurons grown on Ng-CAM, a chick homolog of L1-CAM, extend 21 µm (+/–2) after 24 h in culture in the presence of control AP-Scramble peptides ($n=106$). In contrast, neurons cultured in the presence of AP-YF extend 55% above control levels (32 µm +/–2; $p<0.01$, $n=105$)). Axon extension on laminin, which promotes outgrowth through interactions with cell surface integrins (Felsenfeld et al. Neuron. 1994 12:675-690), was not significantly affected by AP-YF peptide treatment (p>0.05, n=322) versus treatment with AP-Scramble peptide (n=273). These experiments show that peptide inhibitors of L1-CAM-ankyrin interactions selectively stimulate L1-CAM-mediated neuronal growth.

Figure 6:
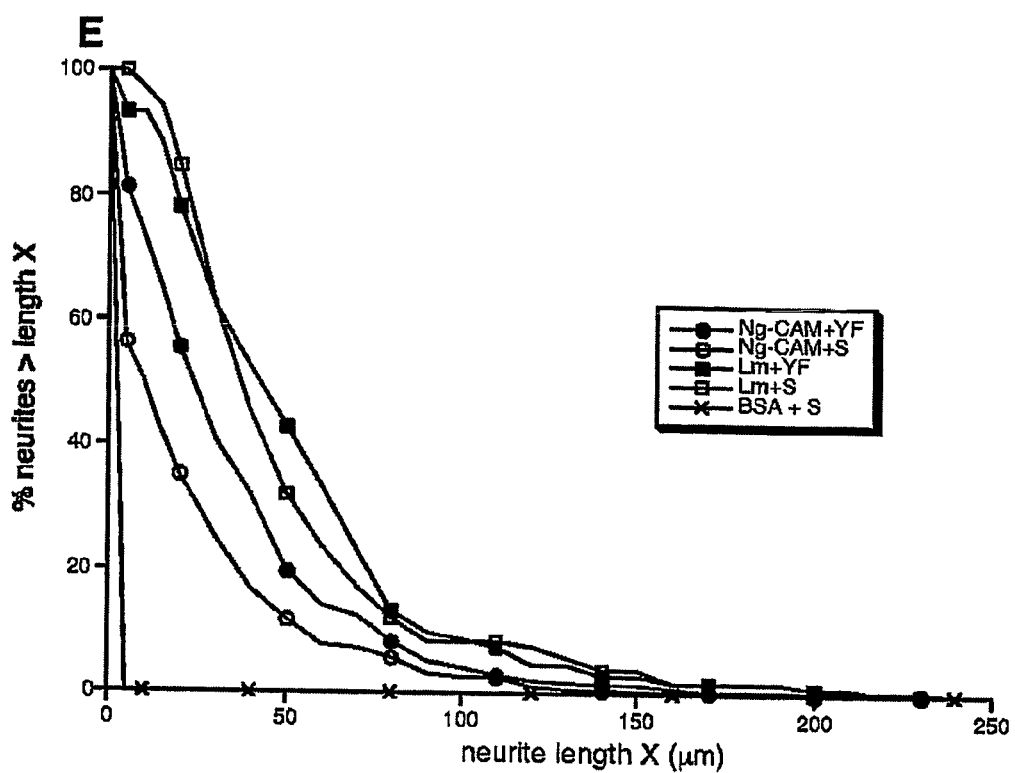
FIG. 6 depicts data showing that peptide inhibitors of L1-CAM-ankyrin interactions selectively stimulate L1-CAM-mediated neuronal growth. This graph shows the percentage of neurons with neurites longer than a given length (y-axis, % neurite>length X) versus the given neurite lengths (x-axis, neurite length X in μm). "Ng-CAM+YF"=mouse cerebellar granular neurons plated on tissue culture dishes coated with chick Ng-CAM and treated with AP-YF peptide (n=322). "Ng-CAM+S" =mouse cerebellar granular neurons plated on tissue culture dishes coated with chick Ng-CAM and treated with AP-Scramble peptide (n=273). "Lm+YF"=mouse cerebellar granular neurons plated on tissue culture dishes coated with mouse laminin and treated with AP-YF peptide (n=105). "Lm+S"=mouse cerebellar granular neurons plated on tissue culture dishes coated with mouse laminin and treated with AP-Scramble peptide (n=106). "BSA+S" (negative control)=mouse cerebellar granular neurons plated on tissue culture dishes coated with bovine serum albumin and treated with AP-Scramble peptide.

FIG. 6 is a graph showing the percentage of neurons (y-axis, % neurite) with neurites longer than a given length (x-axis, neurite length in lam). Note that treatment of culture on Ng-CAM substrate with YF peptide (closed circle) shifted profile plot to the right compared to control treatment with S peptide (open circle), indicating that the AP-YF peptide stimulated neurite outgrowth. Conversely, whereas peptide treatment did not affect the profile plot of neurons grown on the laminin substrate (squares). Control substrate (BSA) did not promote neurite extension (x).

Example 9

Test of Peptide Inhibitors of Ankyrin Binding to L1-CAM in an Animal Model of Spinal Cord Injury L1-CAM is expressed in descending corticospinal tract neurons in the dorsal spinal cord (Cohen et al. Current Biology 1998;8:26). The effect of peptide inhibitors of ankyrin binding to L1-CAM on axon growth following spinal-cord injury is assessed in an animal model of spinal cord injury as described in Zheng et al Neuron 38 p213, 2003). In particular, the inhibitory peptide AP-YF peptide (amino acid sequence RQIKIWFQNRRMKWKKQFNEDGSFIGQF; SEQ ID NO: 3) is assessed in this model.

In brief, female mice 6-14 weeks old are anesthetized with Avertin (Sigma). Following, shaving and swabbing with Betadine, a midline incision is made over thoracic vertebrae, the paravertebral muscles are separated from the vertebral column, and laminectomy is performed at the desired level (T7-8). The spinal cord is injured by dorsal hemisection using a fine microknife. Following injury and before closing the wound, a cannula is implanted into the central canal or the sub-dural space to facilitate the delivery of peptide to the site of injury. After hemostasis is achieved, the muscle layers and skin are sutured and animals are placed on a heating pad until they have fully recovered from the anesthetic.

Peptides, either AP-YF or AP-Scramble control, are delivered to the site of injury via the implanted cannula using an osmotic pump (Alzet model 2ML4; Alzet Osmotic Pumps) at a rate of 2.5 μl/hr and a concentration range of 0.5-5 μg/ml for a period of 4 weeks.

To visualize the descending corticospinal tract axons, a traceable dye is injected at 5 weeks post injury (tetramethyl-rhodamine and biotin-conjugated dextran 10,000 MW, lysine fixable (mini-ruby; Molecular Probes)) bilaterally into the sensorimotor cortex. Animals are sacrificed at 7 weeks post-injury and, following fixation, spinal cords are subject to parasagittal sectioning to detect signs of axon regeneration across the site of injury.

Example 10

AP-YF Peptide Induces Removal of $Ca_v2.2$ Channels from the Plasma Membrane

Materials and Methods

Antibodies: Primary antibody: rabbit anti-pan $\alpha_1$ binds Ca channel (1:200 dilution, [1.5 μg/ml) [Alomone Labs; Jerusalem, Israel]. Secondary antibodies: (1:200 dilution, 10 μg/ml): tetramenthylrhodamine conjugated goat anti-rabbit IgG (H+L) [Molecular Probes; Eugene, OR]

Cell culture: Embryonic chicken sensory neurons were grown in culture according to methods described in Canfield and Dunlap, 1984 British J. Pharmacol. 82, 557-563. Dorsal root ganglia were dissected from 11 to 12 day old embryos, incubated for 30 min in saline containing nominal $Ca^{2+}$ and $Mg^{2+}$, and 0.05% collagenase (type A, Boehringer Mannheim). Ganglia were dissociated mechanically into single cells by trituration in culture medium containing Dulbecco's modified Eagle's medium supplemented with 10% horse serum, 5% chicken embryo extract, penicillin, streptomycin, glutamine, and nerve growth factor. Cells were plated at a density of ~50,000 cells/collagen-coated 35 mm tissue culture dish and studied between 1 and 3 days in vitro.

Immunohistochemistry: Cultures grown on poly-L-lysine cover glass slips were exposed to saline or 100 mM NE (norepinephrine), fixed and permeabilized in methanol at −20° C. for 15-minutes or 20 second (for residual experiment) followed by 3×5-min washes in PHEM Buffer [60 mM PIPES, 25 mM HEPES, 10 mM EGTA, 2 mM $MgCl_2$, pH 6.9]. Cells were alternatively fixed with 4% paraformaldehyde in PHEM buffer, pH 6.9 for 20-min, washed 3×3-min with PHEM buffer and permeabilization with 0.1% Triton X-100/PHEM buffer for 3-min. Blocking was performed using 5% BSA in PHEM Buffer for 1-h at 4 C. Following overnight incubation with primary antibody in 1% BSA and 1% normal goat sera in PHEM Buffer at 4 C. After washes with PHEM Buffer, cover slips were incubated with fluorophore-conjugated secondary antibodies in 1% BSA PHEM Buffer for 1.5 hours at room temperature in the dark. Cover glass slips were washed 4 times (5-min each) in 1% BSA PHEM Buffer and mounted on glass slides with one drop of Vectashield anti-fade reagent [Vector Laboratories, Burlingame, Calif.] and sealed.

Transmitter application: Transmitters were prepared fresh in HBS $Ca^{2+}$ external buffer (2.5 mM-KCl) at 100 mM concentrations (1000×) [(+/−) Norepinephrine (+) bitartrate salt [Sigma], γ-Aminobutyric acid (GABA) [Sigma], and (+/−) Baclofen (4-Amino-3-[4-chlorophenyl] butanoic acid, [Sigma]]. Transmitter was diluted in the appropriate HBS $Ca^{2+}$ external buffer immediately prior to experiments. Cells were washed once with HBS $Ca^{2+}$ external buffer (2.5 mM KCl) at room temperature followed by the addition of 2 ml of HBS $Ca^{2+}$ external buffer (60 mM KCl), with or without a final concentration of 100 mM transmitter for 20-sec or 5-min at room temperature.

Confocal Imaging: Confocal laser-scanning microscopy was performed at the MSSM-Microscopy Shared Resource Facility, using a Leica TCS-SP (UV) microscope in an inverted configuration. Images of fixed cells were obtained with a pinhole setting of 0.95 using a UV 100× 1.4NA oil Leica objective lens and an optical zoom between 1.4 and 2× at slow acquisition speed with 4× frame averaging accumulation. The number of sections was calculated by the Leica TCS software based on acquisition of sections at 240 nm intervals in the Z-plane. Images were subsequently converted to color using the provided color pallet or to black and white and were saved both as Leica TCS experiment files and as tiff export files. Confocal Z-stack images were also combined using the Leica TCS software package to create projected images, which were saved as tiff files.

Peptides; Peptides were synthesized by FastMoc chemistry at the Tufts University Core Facility and purified by HPLC with >97% purity as determined by mass spectrometry. An amino-terminal biotin was included in every peptide. Peptides were dissolved in 5 mM acetic acid at 1 mg/ml and diluted into the internal solution for electrophysiological experiments or HBSS for biochemical experiments.

The novel peptide of the present invention comprises the amino acid sequence of the L1-CAM ankyrin-binding domain in which the carboxy-terminal tyrosine has been changed to phenylalanine (QFNEDGSFIGQF (SEQ ID NO: 2)). In an exemplified embodiment, the peptide referred to as "AP-YF" comprises the amino acid sequence RQIKIWFQN-RRMKWKKQFNEDGSFIGQF (SEQ ID NO: 3), where the 16 amino acid penetratin domain of drosophila antennapedia protein, which mediates translocation of the peptide across the plasma membrane and into the cytoplasm of cells (see, e.g., Derossi et al. Trends Cell Biol 1998;8:84-87), is indicated in bold. A negative control AP-S (scrambled) comprises the reversed sequence of QFNEDGSFIGQF (SEQ ID NO: 2) C-terminal to the intact antennapedia domain AP-YF Peptide Treatment Peptide: AP-S (scrambled) and peptide AP-YF (SEQ ID NO: 3) were incubated 15-min at 37° C. prior to addition to DRG medium for a final concentration of 1.4 µg/ml. Cells were treated in the presence of peptide for 30-min in a CO2 incubator at 37° C. prior to saline or transmitter treatment for 1 hour.

For experiments determining the effect of AP-YF peptide on calcium channels distribution, calcium channels were detected by anti-pan $\alpha_{-1}$ antibody followed by a rhodamine-conjugated secondary antibody. Confocal images using indirect immunofluorescence were captured.

Results and Discussion

Figure 9:
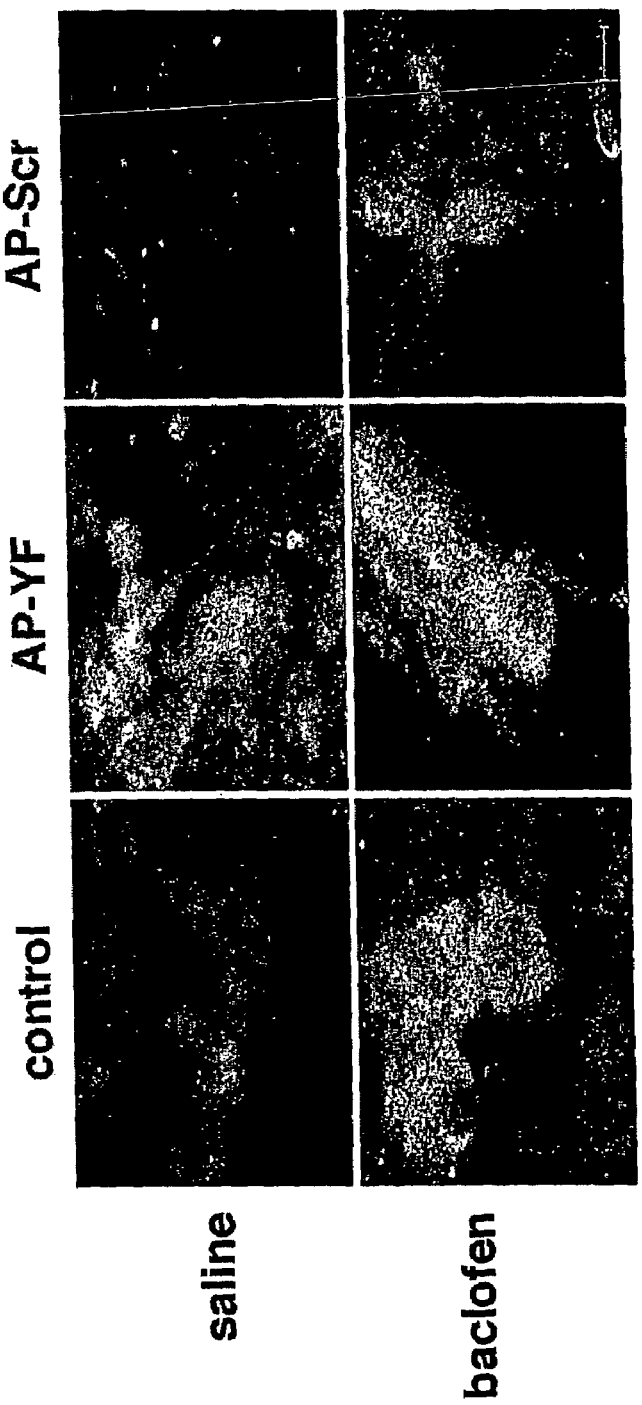
FIG. 9 is a set of confocal microscopy images showing the redistribution of fluorescently labeled calcium channels from the plasma membrane to the cytoplasm of the cell in response to various treatments. Column labels indicate cells with no pretreatment ("control"), or pretreated with the peptides AP-YF or AP-Scr. Top row has been treated with saline, bottom row has been treated with baclofen.

The fluorescence puncta observed when dorsal root ganglia cells were stimulated by NE and other G-proteins is likely to represent clusters of many calcium channels. Such clusters might require the interaction of the channels with cytoskeletal components. The receptor-induced removal of calcium channels from the membrane raises the possibility that activation of heterotrimeric G proteins causes disruption of cytoskeletal elements that might anchor the channels in the membrane. While the mechanisms of synaptic targeting of calcium channels have been widely studied (Maximov A, Bezprozvanny I. J Neurosci. 22: 6939-52), the molecular mechanisms involved in the retention of $Ca_v2.2$ channels at the plasma membrane are largely unknown. The best-characterized example of selective retention of a voltage-dependent ion channel is that of the anchoring of $Na_v$ channels through indirect interactions with L1 family member neurofascin in neurons (Jenkins S M and Bennett V. (2001). J. Cell Biol. 155: 739-46). Based on what is known about the retention and membrane organization of $Na_v$ channels, to test whether of the L1-CAM-ankyrin interaction plays a role in the retention of calcium channels in the membrane, a cell permeant peptide which disrupts L1-CAM-ankyrin interaction was employed (AP-YF peptide, Gil et al. (2003) J. Cell Biol. 162:719-30). This peptide has two domains: an antennopodia penetratin domain that allows the peptide to permeate the membrane and the 12 aa ankyrin interaction domain of L1-CAM with the terminal tyrosine residue replaced with a phenylalanine (Jenkins S M and Bennett V. (2001). J. Cell Biol. 155:739-46). Pretreatment of DRG neurons with AP-YF peptide (1.4 µg/ml, 30 min.) induces removal of $Ca_v2.2$ channels in a manner similar to that mediated by G proteins (FIG. 9). Calcium channels are found in the cytoplasm of the neurons. A scrambled peptide (AP-Scr) in which the L1-CAM domain sequence is reversed had no effect. These results suggest that L1-CAM-ankyrin interaction functions to retain $Ca_v2.2$ channels at the plasma membrane.

Example 11

L1-CAM Cytoskeleton Interactions Depend on L1-CAM Crosslinking

Material and Methods

Co-precipitation: $1 \times 10^6$ DRG cells were used for each condition. DRG neurons were exposed to control solution containing 100 µM bicuculline or 100 µM GABA in the presence of 100 µM bicuculline. After agonist treatment, DRG neurons were lysed with ice-cold buffer (phosphate buffered saline, pH 7.4, containing 250 µM sodium pervanadate, 1% (v/v) NP-40, 1 mM Pefabloc, 1 mM EDTA, 1 mM EGTA, 10 µg/ml pepstatin, 10 µg/ml leupeptin, and 100 µg/ml soybean trypsin inhibitor, 100 µg/ml calpain I and 100 µg/ml calpain II inhibitors. The $\alpha_1$ subunit of the $Ca_v2.2$ channel was immunoprecipitated as previously described (Schiff, M. L et al., (2000). Nature 408:723-726.).

Cell culture, transmitter application: Cell culture and transmitter application, were performed as described in Example 10, supra. For experiments determining the effect of activation of $GABA_B$ receptors upon L1-CAM-ankyrin-calcium channel interaction in DRG neurons, calcium channels were precipitated from DRG neurons treated with saline or baclofen for 20 seconds using anti-pan alpha 1 antibody and then immunoblotted for ankyrin (anti-ankyrin B antibody) or L1-CAM (8D9 anti-NgCAM).

Results and Discussion

Figure 10:
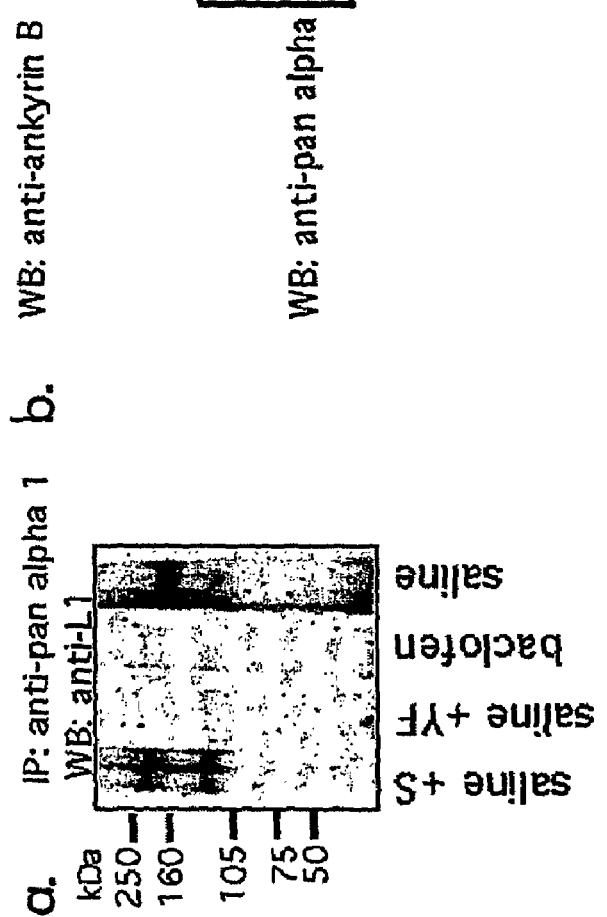
FIGS. 10(A and B) are photographs of Western Blots. 10A is a photograph of a Western blot of Ca$_v$2.2 proteins immunoprecipitated from dorsal root ganglion neurons ("IP") and probed with an antibody against L1-CAM ("WB"). The conditions for treatment of neurons are indicated under each lane from right to left: saline+peptide AP-Scr ("S"), saline+peptide AP-YF ("YF"), baclofen, and saline. 10B is a photograph of a Western blot of Ca$_v$2.2 channel proteins immunoprecipitated ("IP") from dorsal root ganglion neurons and probed with antibodies against either ankyrin B (top panel) or Ca$_v$2.2 (bottom panel, "anti-pan alpha") proteins. The conditions for treatment of neurons are indicated under each lane from right to left: saline, saline+peptide AP-YF ("YF"), peptide AP-Scr ("S"), baclofen, baclofen+peptide AP-YF ("YF"), and baclofen+peptide AP-Scr ("S").

Since AP-YF peptide mimics G protein-mediated removal of calcium channels from the membrane, the direct association between calcium channels with L1-CAM and ankyrin was tested, as was whether the activation of G protein-coupled receptors could alter the association. L1-CAM and ankyrin B co-precipitate with $Ca_v2.2$ channel protein from chick DRG neurons treated with saline, and pretreatment with AP-YF but not AP-Scr abolished the interaction (FIGS. 10a and b). Activation of GABA receptors (FIGS. 10a and b) or β2-adrenergic receptors reduced the amount of ankyrin and L1-CAM that co-precipitated with the calcium channel. These results suggest that activation of G protein-coupled receptors results in disruption of a complex containing L1-CAM, ankyrin B and $Ca_v2.2$. Furthermore, interaction with L1-CAM seems to be necessary for ankyrin B binding to the calcium.

Example 12

Disruption of L1-CAM-ankyrin Interaction Inhibits $Ca_v2.2$ Current and Secretion of Substance P Material and Methods Electrophysiology: Standard tight seal, whole-cell recording methods [Hamill et al.,1981 Pflugers Arch. 381, 85-10] were employed. Cells were incubated in an external solution containing 133 mM NaCl, 1 mM CaCl2, 0.8 mM MgCl2, 25 mM HEPES, 12.5 mM NaOH, 5mM glucose, 10 mM tetraethylammonium chloride, 0.3 mM tetrodotoxin (pH 7.4). Experiments were performed on the stage of an inverted microscope. Recording pipettes were fabricated from microhemnatocrit tubing (Fisher) and filled with an internal recording solution containing 150 mM CsCl, 5 BAPTA, 5 MgATP, 10 HEPES (pH 7.2). All salts were obtained from Fluka. Initial pipette resistances were 0.8-1.2 MΩ. Signals from a List EPC7 amplifier de-were filtered at 3 kHz, digitized at 10 kHz using an ITC16 A/D interface (Instrutech Corp, Great Neck, N.Y.), and stored for later analysis on a Macintosh computer with software by HEKAElektronik (Federal Republic of Germany). For extracellular application, agents were diluted into standard extracellular saline and applied via wide-bore pipette. For the experiments presented in this report calcium current has been corrected for rundown by measuring calcium current as a function of time in control cells without transmitter. Cells used for experiments exhibited a rundown of the current of less than 1%/1 minute. The external saline contained 133 mM NaCl, 1 mM $CaCl_2$, 0.8 mM $MgCl_2$, 10 mM tetraethylammonium chloride, 25 mM HEPES, 12.5 mM NaOH, 5 mM glucose, and 0.3 μM tetrodotoxin. The pipette internal solution contained 150 mM CsCl, 10 mM HEPES, 5 mM Mg ATP, and 5 mM bis (o-aminophenoxy)-ethane-tetraacetic acid (BAPTA). Pipettes resistances prior to forming high resistance seals ranged from 1-2 MΩ.

Drug delivery method: Where indicated, drug were diluted into the recording pipette solution and introduced into the cells by diffusion following whole cell access. For certain experiments, molecules were pressured injected into the cytosol. For these, injection pipettes were back filled with 3 μl of 10 ng/μl recombinant GRK (containing 1% fluorescein dextran) and mounted on an Eppendorf 5171 microprocessor-controlled micromanipulator. Cells on the stage of a Zeiss Axiovert 10 microscope were visualized with phase-contrast optics. An automated Eppendorf 5272 microinjector was used to introduce the recombinant GRKs into sensory neuron cell bodies. Standardized injection pressures (30-50 HPa) and time (0.3 s) were used to minimize variability in injection volumes (that are estimated to be about 0.5 nl).

Solutions containing norepinephrine (D,L-arterenol, Sigma) were made fresh on the day of their use; the drug was diluted to the desired concentration in external solution and applied by pressure ejection from a blunt-tipped (0.5 μm diameter) pipette positioned close to the cell of interest.

AP-YF (SEQ ID NO: 3) or scrambled peptide (1.4 ng/ml) was included in the recording pipette. Inward $Ca^{2+}$ current was evoked by stepping from −80 mV to 0 mV for 50 ms. A protocol with +80 mV, 20 ms prepulse and a 5 ms interval prior to the test pulse was used to measure the voltage-independent component of the inhibition. Bottom trace shows $Ca^{2+}$ current measured at 30 seconds after achieving whole-cell configuration and top trace shows $Ca^{2+}$ current after equilibration for 2 minutes with peptide-containing internal solution.

Electrophysiology Data Analysis—Data was filtered at 3 kHz, acquired at 10-20 kHz and analyzed using PulseFit (HEKA) and IgorPro (WaveMetrics) on a Macintosh G3 computer. Strong depolarizing conditioning pulses (to 80 mV) that precede test pulses (to 0 mV) reverse GABA-induced voltage-dependent inhibition without affecting voltage-independent inhibition. Such conditioning pulses have no effect on control currents recorded in the absence of GABA. During the application of the transmitter, test pulse currents measured before and after the conditioning pulse are subtracted to yield the voltage-dependent component. Test pulses measured following the conditioning pulse are subtracted from control currents (measured in the absence of GABA) to yield the voltage-independent component.

Secretion Assay: Secretion of substance P was analyzed using the single-cell immunoblot method adapted from Huang and Neher (Huang, L. Y., Neher, E. (1996) Neuron. 17, 135-45.). Briefly, polyvinylidene difluoride transfer membranes (Immobilon P brand from Millipore) were cut to 22×22 nm and placed in a 6-well plate. Membranes were pre-wetted with methanol for 20 s, rinsed with distilled water and allowed to equilibrate in test solution for >1 hr. In parallel, DRG cells plated were incubated with media containing AP-YF or AP-Scr (1.4 μg/ml) for 1 hour. This media was removed, and replaced with 70 μl of test solution. The membranes were then placed on top of the cells, and allowed to incubate at 37° C. in a humidified $CO_2$ incubator for 30 min. The membranes were then carefully removed from the cells and allowed to dry completely and fixed with powdered paraformaldehyde at 80° C. for 1 hr. Fixed membranes were rinsed in PBS (1 mM $KH_2PO_4$, 10 mM $Na_2HPO_4$, 137 mM NaCl, 2.7 mM KCl) containing 1% Triton X-100 (PBS-T) to remove excess paraformaldehyde, and blocked with PBS-T containing 3% fetal bovine serum (FBS) for 30 min at room temperature. The membranes were incubated with anti-substance P antibody (Santa Cruz) at 1:200 dilution in PBS-T with 1% FBS overnight in 37° C. incubator. The next day the membranes were developed with a peroxidase/diamninobenzidine (DAB) reaction using the ABC staining kit from Santa Cruz Biotechnology. Images were taken using a CCD camera, and analyzed using Photoshop and NIH image software. Data were plotted by assigning an upper and lower limit of gray values and plotting % of cells at a range within those limits. By plotting graphs as % of cells in a dynamic range, multiple experimental runs were pooled.

Results and Discussion

The effect of disrupting $Ca_v2.2$-L1-CAM-ankyrin B containing complexes on whole-cell calcium currents in embryonic chick DRG neurons was tested. AP-YF or AP-Scr peptide was introduced into the cytoplasmic environment by passive diffusion through the recording pipette, and calcium current was measured as a function of time. AP-YF peptide (1.4 ng/ml) inhibited calcium current by 83+17% after 2 minutes if recording (FIGS. 11a-b), whereas the scrambled peptide had no significant effect.

A prepulse to a positive potential (+80 mV) facilitates the current (FIG. 11b) suggesting that AP-YF peptide-induced calcium current inhibition has voltage-dependent and -independent components just like transmitter-mediated inhibition of $Ca_v2.2$ in chick DRG neurons (Bean B P. Nature. 1989 Jul. 13; 340(6229): 153-6.).

Figure 11:
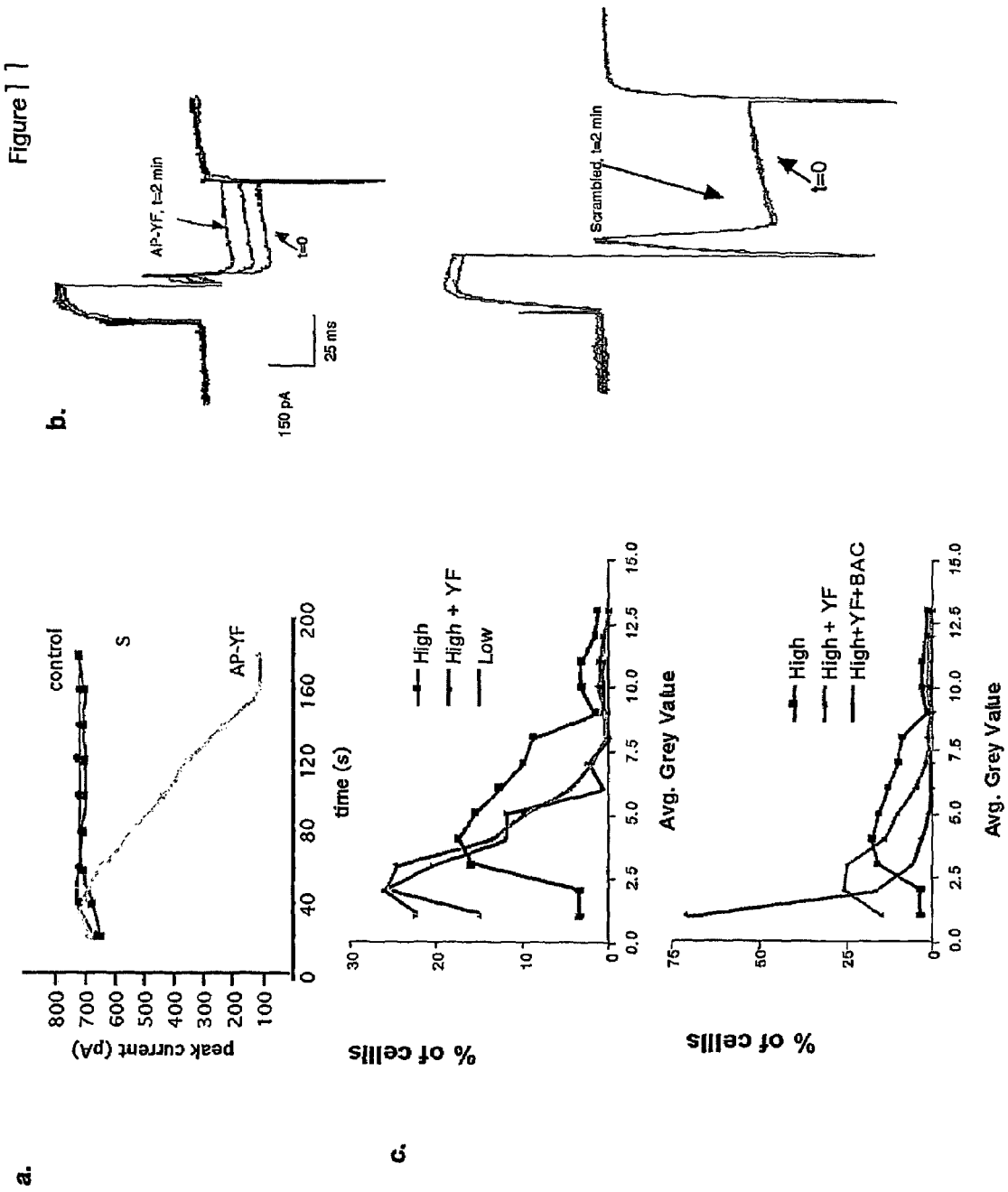
FIGS. 11A-C. 11A is a graph of the results of electrophysiology experiments showing peak current at various timepoints. Conditions for treatment are control, peptide AP-YF ("YF"), and peptide AP-Scr ("S"). 11B is a set of electrophysiology traces showing the ability of a single cell to carry current. The top panel was treated with AP-YF; bottom trace shows Ca$^{2+}$ current measured at 30 seconds after achieving whole-cell configuration, and top trace shows Ca$^{2+}$ current after equilibration for 2 minutes with AP-YF peptide-containing internal solution. The bottom panel shows the result of a cell treated with AP-S peptide ("Scrambled"). 11C is a set of graphs showing the percentage of cells (Y-axis) expressing Substance P (X-Axis, "Avg. Grey Value") for different experimental conditions. The conditions referred to are high K$^+$ ("High"), low K$^+$ ("Low"), with peptide AP-YF ("YF") and/or with baclofen ("BAC").

Inhibition of calcium influx by AP-YF peptide should result in alterations of calcium-dependent processes such as exocytosis. To examine this question directly, secretion of Substance P from chick DRG neurons was measured using single-cell blot secretion assays (Gruner W and Silva L R (1994). J. Neurosci 1994 May 14:2800-8). Following the method developed by Neher and colleagues, the density of the chemiluminescence signal for Substance P was measured for individual DRG neurons. The frequency of cells showing a given value or density was plotted for different experimental conditions. High K$^+$-induced depolarization causes secretion of substance P from DRG neurons while cells in low K$^+$ secrete low levels of substance P (FIG. 11c), Pre-iricubation of neurons with AP-YF peptide blocks high K$^+$-induced secretion, decreasing secretion to levels observed in low K$^+$ (FIG. 11c). Baclofen has an additional effect on AP-YF peptide induced inhibition of secretion with 75% of DRG neurons secreting low levels of Substance P. The scrambled peptide did not affect secretion significantly. These results demonstrate that under experimental conditions where removal of calcium channels was observed, AP-YF peptide causes a robust inhibition of high K$^+$-induced secretion of Substance P. The results from the secretion assays show that the disruption of the L1-ankyrin B interaction results in a decrease in the K$^+$-induced secretion to the levels observed under non-depolarizing conditions. This is consistent with a loss of calcium channels in the plasma membrane; even if the neurons are depolarized, calcium influx is reduced.

Example 13

Complex Involved in the Retention of Ca$_v$2.2 Channels at the Plasma Membrane

Material and Methods

This scheme summarizes the major findings of Examples 9-11: i. L1-CAM and ankyrin B are associated with Ca$_v$2.2 channel, ii-Activation of G$_{i/o}$ protein-coupled receptors or addition of AP-YF peptide disrupt L1-CAM-ankyrin interaction, iii. Disruption of the complex induces removal of Ca$_v$2.2 channel from the membrane and sequestration into vesicles (iv.), which leads to a decrease in calcium signaling and a blockade of Substance P secretion.

Example 14

Test of Peptide Inhibitor of Ca$_v$2.2 Channel Plasma Membrane Retention in an Animal Model of Pain Transmission AP-YF peptide will be tested in a rat model system for chronic pain as described (Fox, A., C. Gentry, S. Patel, A. Kesingland, and S. Bevan. 2003. Comparative activity of the anti-convulsants oxcarbazepine, carbamazepine, lamotrigine and gabapentin in a model of neuropathic pain in the rat and guinea-pig. Pain. 105:355-62.). Tactile allodynia will be induced by partial, unilateral sciatic nerve ligation in male Wistar rats (120-150 g). After 12-15 days of recovery post surgery, foot withdrawal in response to foot pad stimulation will be evaluated in the presence of AP-YF or AP-scramble (control) peptides as described in Example 10, supra. Peptides will be administered by intrathecal injection adjacent to the dorsal horn at lumbar segment 5 (L5) or sacral segment 1(S1) where the sciatic nerve impinges on the spinal cord. Foot withdrawal response will be evaluated initially at 30 minutes, 1, 4 and 8 hours after injection.

The present invention is not to be limited in scope by the specific embodiments described herein. Indeed, various modifications of the invention in addition to those described herein will become apparent to those skilled in the art from the foregoing description and the accompanying figures. The invention is therefore to be limited only by the terms of the appended claims, along with the full scope of equivalents to which the claims are entitled.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. An isolated peptide derived from the ankyrin binding domain of an L1-CAM family member protein, wherein said peptide (i) does not contain transmembrane and extracellular portions of the L1-CAM family member protein, (ii) comprises the amino acid sequence of QFNEDGSFIGQF (SEQ ID NO: 2), and (iii) promotes neurite outgrowth.

2. The peptide of claim 1 comprising the amino acid sequence of QFNEDGSFIGQF (SEQ ID NO: 2) linked to the amino acid sequence of RQIKIWFQNRRMKWKK (SEQ ID NO: 6), wherein said sequences are linked by a disulfide bond.

3. A pharmaceutical composition comprising the peptide of claim 1 and a pharmaceutically acceptable carrier.

4. An isolated peptide consisting of the amino acid sequence of QFNEDGSFIGQF (SEQ ID NO: 2).

5. The peptide of claim 1, which comprises a targeting sequence comprising the amino acid sequence of RQIKIWFQNRRMKWKK (SEQ ID NO: 6).

6. An isolated peptide consisting of the amino acid sequence of RQIKIWFQNRRMKWKKQFNEDGSFIGQF (SEQ ID NO: 3).

7. A method for promoting outgrowth of a mammalian neuron comprising contacting said neuron with the peptide of claim 1.

* * * * *

UNITED STATES PATENT AND TRADEMARK OFFICE
CERTIFICATE OF CORRECTION

PATENT NO. : 7,737,250 B2
APPLICATION NO. : 10/561015
DATED : June 15, 2010
INVENTOR(S) : Dan P. Felsenfeld et al.

Page 1 of 1

It is certified that error appears in the above-identified patent and that said Letters Patent is hereby corrected as shown below:

Page 1, (column 1, line 21) – delete "The research leading to this invention was supported, in part, by Grant No. GM63192-01 and Grant No. N537443 awarded by the National Institutes of Health. Accordingly, the United States government may have certain rights to this invention" and insert -- This invention was made with government support under grant No. GM063192 awarded by the National Institutes of Health. The government has certain rights in the invention. --

Signed and Sealed this
Fifteenth Day of March, 2011

David J. Kappos
*Director of the United States Patent and Trademark Office*

SEQUENCE LISTING

```
<160> NUMBER OF SEQ ID NOS: 27

<210> SEQ ID NO 1
<211> LENGTH: 12
<212> TYPE: PRT
<213> ORGANISM: Artificial sequence
<220> FEATURE:
<223> OTHER INFORMATION: synthetic protein

<400> SEQUENCE: 1

Gln Phe Asn Glu Asp Gly Ser Phe Ile Gly Gln Tyr
1               5                   10

<210> SEQ ID NO 2
<211> LENGTH: 12
<212> TYPE: PRT
<213> ORGANISM: artificial sequence
<220> FEATURE:
<223> OTHER INFORMATION: sythetic protein

<400> SEQUENCE: 2

Gln Phe Asn Glu Asp Gly Ser Phe Ile Gly Gln Phe
1               5                   10

<210> SEQ ID NO 3
```

```
<211> LENGTH: 28
<212> TYPE: PRT
<213> ORGANISM: artificial sequence
<220> FEATURE:
<223> OTHER INFORMATION: synthetic protein

<400> SEQUENCE: 3

Arg Gln Ile Lys Ile Trp Phe Gln Asn Arg Arg Met Lys Trp Lys Lys
1               5                   10                  15

Gln Phe Asn Glu Asp Gly Ser Phe Ile Gly Gln Phe
            20                  25

<210> SEQ ID NO 4
<211> LENGTH: 3797
<212> TYPE: DNA
<213> ORGANISM: Rattus rattus

<400> SEQUENCE: 4
gctagctatg gtcgtgatgc tgcggtacgt gtggcctctc ctcctctgca gcccctgcct      60
gctcatacag attcctgatg aatataaagg acaccatgta ctagagccac ctgtcatcac     120
ggaacagtct ccacggcgcc tggttgtctt cccaacagat gacataagcc tcaaatgtga     180
agccagaggc agaccccaag tggagttccg ctggacgaaa gatggcatcc acttcaaacc     240
taaggaagaa ttgggtgtag tggtacacga ggcaccctat tctggctcct tcaccatcga     300
aggcaacaac agctttgccc agaggtttca gggcatctat cgctgctatg ccagcaataa     360
tctaggaact gccatgtcgc atgagatcca gctcgtggct gagggtgccc ccaaatggcc     420
gaaggagact gtaaaacccg tggaagtgga ggaaggagaa tcagtagttc taccttgcaa     480
tcctccaccc agtgcagccc acttaggat ctactggatg aacagcaaga ttttgcacat     540
caaacaagat gagcgggtgt ccatgggcca gaatggagac ctatattttg ccaatgtgct     600
tacctcagac aatcattcag actacatctg caatgcccac ttccctggca cccggaccat     660
cattcaaaag gaacctattg acctccgggt caagcccacc aacagcatga ttgaccggaa     720
gccacgcctg ctcttcccca caactccag cagtcacctc gtggccttgc agggccagtc     780
attaatcctg gagtgcattg ctgagggatt ccctacaccc accatcaagt ggctgcaccc     840
cagtgacccct atgccaacag accgtgttat ctaccagaac cataacaaga cactgcagct     900
cctcaatgtg ggcgaggaag atgatggcga gtatacctgc cttgctgaga ctcactgggg     960
cagtgctcgg catgcctact atgtcactgt ggaagctgcc ccatactggc tgcagaagcc    1020
ccagagtcat ttgtatgggc aggagagac tgcccgccta gactgccaag tccagggcag    1080
gccccaacca gaggtcactt ggagaatcaa cggaatgtct atagagaagg tgaacaagga    1140
ccagaagtac cggattgagc aggggtcttt gatcctgagt aatgtgcaac caagtgacac    1200
aatggtgacc cagtgtgaag ctcgcaacca gcatgggctc ctactagcca atgcctatat    1260
ctatgttgtc cagctgccag ccaggatcct aacaaaagac aatcagacat acatggcagt    1320
agagggcagt actgcttact tgctgtgcaa agcctttgga gctcctgttc cagtgtcca    1380
gtggctggat gaggaaggaa ccacagtgct tcaggatgaa agattttttcc cctatgccaa    1440
tggaacgctg ggcatcagag atcccaggc caatgacact ggacgctatt ctgccaggc    1500
tgccaatgac cagaacaatg tgaccatttt ggctaaccta caggttaaag aagcaaccca    1560
gatcacacaa ggaccccgga gcacaattga agaaaaggt gcaagggtga cattcacgtg    1620
ccaggcctcc tttgacccct ctttacaagc cagcatcact tggcgtggag atgggagaga    1680
cctccaggaa cgtggagaca gtgacaagta tttcatgaa gatgggcaac ttgtcatcca    1740
```

```
gagcctggac tacagtgacc agggcaacta cagttgtgtg gccagcactg aactggatga    1800
ggtggagagc agggcacaac tcttagtggt gggaagccct gggccagtgc ctcacctgga    1860
gctgtccgac cgccacttgc tgaagcagag ccaggtgcac ttgtcttgga gccctgctga    1920
agaccacaac tctcccattg agaaatatga cattgaattt gaggacaagg aaatggctcc    1980
tgagaaatgg ttcagtctag gcaaggtgcc aggaaatcag acctctacta ccctcaagct    2040 gtcccctat gtccactata cctttcgggt cactgccatt aacaaatatg gtcccggaga    2100
acccagccct gtctctgaga ctgtagtcac acctgaggca gccccagaga agaaccctgt    2160
ggatgtgaga ggggaaggaa atgagaccaa caatatggtc atcacatgga agccccttcg    2220
gtggatggat tggaatgccc ccagattca gtaccgtgta cagtggcgac cactgggcaa    2280
acaagagacc tggaaggaac agaccgtgag cgacccctcc tggtggtgt ctaacacttc    2340 cacatttgtg ccttatgaga tcaaagtcca ggcagtgaac aaccagggga agggccctga    2400
gccccaggtc accattggct attcagggga agactacccc caggtgagcc ctgagcttga    2460
agacatcaca atcttcaact caagcactgt gctggtcagg tggaggcctg tggacttggc    2520
ccaggttaag ggccacctca ggggatacaa tgtaacgtac tggtggaagg gcagtcagag    2580
aaagcacagc aagaggcatg tccacaaaag tcacatggtg gtacctgcga acaccaccag    2640
tgccatcctc agtggtttgc gtccttacag ctcttatcat gtggaggtac aggccttaa    2700 tgggcggggc ttaggcctg caagtgaatg gaccttcagc accccagagg gagtgcctgg    2760
ccaccctgag gcattacatc tggagtgcca gtcggacact agcctgctac tgcactggca    2820
gccaccactc agccacaatg gagtgctcac tggctacctg ctctcttacc atcccttgga    2880 tgggaaagc aaagagcagt tgttcttcaa cctttcggac ccagagctcc ggactcataa    2940
tctcaccaac ctcaaccctg atctacagta ccgcttccag cttcaggcca ccacccaaca    3000
gggtcctggt gaggccattg tgcgtgaagg aggcactatg gccctatttg gcaagccaga    3060
ttttggcaac atttcagtca cagcaggtga aaactacagt gtggtctcct gggtccctcg    3120
ggagggccag tgcaatttca ggttccacat cctgttcaaa gccttgccag aagggaaagt    3180
gagccctgat caccagcctc agcctcaata tgtgagctac aatcagagct cctacacaca    3240
gtgggaccta cagcctgaca ccaaatatga gatccacctg atgagggaga aggtcctctt    3300
gcaccatctg gctgtgaaga ctaatggcac tggccccgtg cgagtgtcga ctaccggtag    3360 cttttgcctcc gagggctggt tcatcgcctt tgtcagtgct atcattctct tgctcctcat    3420
cctgctcatc ctctgcttca tcaaacgcag caagggcggc aaatattcag tgaaggacaa    3480
ggaggacact caggtagatt ccgaggcccg gccatgaaaa gacgagacct tcggcgagta    3540
caggtccctg agagtgacaa tgaagagaa ggccttcggc agcagccagc catctctcaa    3600
tggagacatc aaacccctag gcagtgatga cagtctggct gattatgggg gcagtgtgga    3660
tgtccagttc aatgaggatg ctctctttca tggccaatac agtggcaaaa agagaagga    3720 ggcagcggga ggcaatgaca gctcaggggc tacctctcct atcaatcctg cagtagccct    3780
agaatagcaa gctcgag                                                  3797

<210> SEQ ID NO 5
<211> LENGTH: 1259
<212> TYPE: PRT
<213> ORGANISM: Rattus rattus

<400> SEQUENCE: 5
```

-continued

```
Met Val Val Met Leu Arg Tyr Val Trp Pro Leu Leu Leu Cys Ser Pro
1               5                   10                  15

Cys Leu Leu Ile Gln Ile Pro Asp Glu Tyr Lys Gly His His Val Leu
                20                  25                  30

Glu Pro Pro Val Ile Thr Glu Gln Ser Pro Arg Arg Leu Val Val Phe
            35                  40                  45

Pro Thr Asp Asp Ile Ser Leu Lys Cys Glu Ala Arg Gly Arg Pro Gln
    50                  55                  60

Val Glu Phe Arg Trp Thr Lys Asp Gly Ile His Phe Lys Pro Lys Glu
65                  70                  75                  80

Glu Leu Gly Val Val Val His Glu Ala Pro Tyr Ser Gly Ser Phe Thr
                85                  90                  95

Ile Glu Gly Asn Asn Ser Phe Ala Gln Arg Phe Gln Gly Ile Tyr Arg
            100                 105                 110

Cys Tyr Ala Ser Asn Asn Leu Gly Thr Ala Met Ser His Glu Ile Gln
    115                 120                 125

Leu Val Ala Glu Gly Ala Pro Lys Trp Pro Lys Glu Thr Val Lys Pro
130                 135                 140

Val Glu Val Glu Glu Gly Glu Ser Val Val Leu Pro Cys Asn Pro Pro
145                 150                 155                 160

Pro Ser Ala Ala Pro Leu Arg Ile Tyr Trp Met Asn Ser Lys Ile Leu
                165                 170                 175

His Ile Lys Gln Asp Glu Arg Val Ser Met Gly Gln Asn Gly Asp Leu
            180                 185                 190

Tyr Phe Ala Asn Val Leu Thr Ser Asp Asn His Ser Asp Tyr Ile Cys
    195                 200                 205

Asn Ala His Phe Pro Gly Thr Arg Thr Ile Ile Gln Lys Glu Pro Ile
210                 215                 220

Asp Leu Arg Val Lys Pro Thr Asn Ser Met Ile Asp Arg Lys Pro Arg
225                 230                 235                 240

Leu Leu Phe Pro Thr Asn Ser Ser Ser His Leu Val Ala Leu Gln Gly
                245                 250                 255

Gln Ser Leu Ile Leu Glu Cys Ile Ala Glu Gly Phe Pro Thr Pro Thr
            260                 265                 270

Ile Lys Trp Leu His Pro Ser Asp Pro Met Pro Thr Asp Arg Val Ile
    275                 280                 285

Tyr Gln Asn His Asn Lys Thr Leu Gln Leu Leu Asn Val Gly Glu Glu
290                 295                 300

Asp Asp Gly Glu Tyr Thr Cys Leu Ala Glu Asn Ser Leu Gly Ser Ala
305                 310                 315                 320

Arg His Ala Tyr Tyr Val Thr Val Glu Ala Pro Tyr Trp Leu Gln
                325                 330                 335

Lys Pro Gln Ser His Leu Tyr Gly Pro Gly Glu Thr Ala Arg Leu Asp
            340                 345                 350

Cys Gln Val Gln Gly Arg Pro Gln Pro Glu Val Thr Trp Arg Ile Asn
    355                 360                 365

Gly Met Ser Ile Glu Lys Val Asn Lys Asp Gln Lys Tyr Arg Ile Glu
370                 375                 380

Gln Gly Ser Leu Ile Leu Ser Asn Val Gln Pro Ser Asp Thr Met Val
385                 390                 395                 400

Thr Gln Cys Glu Ala Arg Asn Gln His Gly Leu Leu Leu Ala Asn Ala
            405                 410                 415

Tyr Ile Tyr Val Val Gln Leu Pro Ala Arg Ile Leu Thr Lys Asp Asn
```

```
                420             425             430
Gln Thr Tyr Met Ala Val Glu Gly Ser Thr Ala Tyr Leu Leu Cys Lys
        435             440             445
Ala Phe Gly Ala Pro Val Pro Ser Val Gln Trp Leu Asp Glu Glu Gly
        450             455             460
Thr Thr Val Leu Gln Asp Glu Arg Phe Phe Pro Tyr Ala Asn Gly Thr
465             470             475             480
Leu Gly Ile Arg Asp Leu Gln Ala Asn Asp Thr Gly Arg Tyr Phe Cys
                485             490             495
Gln Ala Ala Asn Asp Gln Asn Asn Val Thr Ile Leu Ala Asn Leu Gln
                500             505             510
Val Lys Glu Ala Thr Gln Ile Thr Gln Gly Pro Arg Ser Thr Ile Glu
        515             520             525
Lys Lys Gly Ala Arg Val Thr Phe Thr Cys Gln Ala Ser Phe Asp Pro
        530             535             540
Ser Leu Gln Ala Ser Ile Thr Trp Arg Gly Asp Gly Arg Asp Leu Gln
545             550             555             560
Glu Arg Gly Asp Ser Asp Lys Tyr Phe Ile Glu Asp Gly Gln Leu Val
                565             570             575
Ile Gln Ser Leu Asp Tyr Ser Asp Gln Gly Asn Tyr Ser Cys Val Ala
                580             585             590
Ser Thr Glu Leu Asp Glu Val Glu Ser Arg Ala Gln Leu Leu Val Val
        595             600             605
Gly Ser Pro Gly Pro Val Pro His Leu Glu Leu Ser Asp Arg His Leu
        610             615             620
Leu Lys Gln Ser Gln Val His Leu Ser Trp Ser Pro Ala Glu Asp His
625             630             635             640
Asn Ser Pro Ile Glu Lys Tyr Asp Ile Glu Phe Glu Asp Lys Glu Met
                645             650             655
Ala Pro Glu Lys Trp Phe Ser Leu Gly Lys Val Pro Gly Asn Gln Thr
                660             665             670
Ser Thr Thr Leu Lys Leu Ser Pro Tyr Val His Tyr Thr Phe Arg Val
        675             680             685
Thr Ala Ile Asn Lys Tyr Gly Pro Gly Glu Pro Ser Pro Val Ser Glu
        690             695             700
Thr Val Val Thr Pro Glu Ala Ala Pro Glu Lys Asn Pro Val Asp Val
705             710             715             720
Arg Gly Glu Gly Asn Glu Thr Asn Asn Met Val Ile Thr Trp Lys Pro
                725             730             735
Leu Arg Trp Met Asp Trp Asn Ala Pro Gln Ile Gln Tyr Arg Val Gln
                740             745             750
Trp Arg Pro Leu Gly Lys Gln Glu Thr Trp Lys Glu Gln Thr Val Ser
        755             760             765
Asp Pro Phe Leu Val Val Ser Asn Thr Ser Thr Phe Val Pro Tyr Glu
        770             775             780
Ile Lys Val Gln Ala Val Asn Asn Gln Gly Lys Gly Pro Glu Pro Gln
785             790             795             800
Val Thr Ile Gly Tyr Ser Gly Glu Asp Tyr Pro Gln Val Ser Pro Glu
                805             810             815
Leu Glu Asp Ile Thr Ile Phe Asn Ser Ser Thr Val Leu Val Arg Trp
                820             825             830
Arg Pro Val Asp Leu Ala Gln Val Lys Gly His Leu Arg Gly Tyr Asn
        835             840             845
```

-continued

```
Val Thr Tyr Trp Trp Lys Gly Ser Gln Arg Lys His Ser Lys Arg His
    850                 855                 860

Val His Lys Ser His Met Val Pro Ala Asn Thr Thr Ser Ala Ile
865                 870                 875                 880

Leu Ser Gly Leu Arg Pro Tyr Ser Ser Tyr His Val Glu Val Gln Ala
                    885                 890                 895

Phe Asn Gly Arg Gly Leu Gly Pro Ala Ser Glu Trp Thr Phe Ser Thr
                900                 905                 910

Pro Glu Gly Val Pro Gly His Pro Glu Ala Leu His Leu Glu Cys Gln
                915                 920                 925

Ser Asp Thr Ser Leu Leu Leu His Trp Gln Pro Pro Leu Ser His Asn
    930                 935                 940

Gly Val Leu Thr Gly Tyr Leu Leu Ser Tyr His Pro Leu Asp Gly Glu
945                 950                 955                 960

Ser Lys Glu Gln Leu Phe Phe Asn Leu Ser Asp Pro Glu Leu Arg Thr
                965                 970                 975

His Asn Leu Thr Asn Leu Asn Pro Asp Leu Gln Tyr Arg Phe Gln Leu
                980                 985                 990

Gln Ala Thr Thr Gln Gln Gly Pro  Gly Glu Ala Ile Val  Arg Glu Gly
                995                1000                1005

Gly Thr Met Ala Leu Phe Gly Lys Pro Asp Phe Gly  Asn Ile Ser
    1010                1015                1020

Val Thr Ala Gly Glu Asn Tyr  Ser Val Val Ser Trp  Val Pro Arg
    1025                1030                1035

Glu Gly Gln Cys Asn Phe Arg  Phe His Ile Leu Phe  Lys Ala Leu
    1040                1045                1050

Pro Glu Gly Lys Val Ser Pro  Asp His Gln Pro Gln  Pro Gln Tyr
    1055                1060                1065

Val Ser Tyr Asn Gln Ser Ser  Tyr Thr Gln Trp Asp  Leu Gln Pro
    1070                1075                1080

Asp Thr Lys Tyr Glu Ile His  Leu Met Arg Glu Lys  Val Leu Leu
    1085                1090                1095

His His Leu Ala Val Lys Thr  Asn Gly Thr Gly Pro  Val Arg Val
    1100                1105                1110

Ser Thr Thr Gly Ser Phe Ala  Ser Glu Gly Trp Phe  Ile Ala Phe
    1115                1120                1125

Val Ser Ala Ile Ile Leu Leu  Leu Leu Ile Leu Leu  Ile Leu Cys
    1130                1135                1140

Phe Ile Lys Arg Ser Lys Gly  Gly Lys Tyr Ser Val  Lys Asp Lys
    1145                1150                1155

Glu Asp Thr Gln Val Asp Ser  Glu Ala Arg Pro Met  Lys Asp Glu
    1160                1165                1170

Thr Phe Gly Glu Tyr Arg Ser  Leu Glu Ser Asp Asn  Glu Glu Lys
    1175                1180                1185

Ala Phe Gly Ser Ser Gln Pro  Ser Leu Asn Gly Asp  Ile Lys Pro
    1190                1195                1200

Leu Gly Ser Asp Asp Ser Leu  Ala Asp Tyr Gly Gly  Ser Val Asp
    1205                1210                1215

Val Gln Phe Asn Glu Asp Gly  Ser Phe Ile Gly Gln  Tyr Ser Gly
    1220                1225                1230

Lys Lys Glu Lys Glu Ala Ala  Gly Gly Asn Asp Ser  Ser Gly Ala
    1235                1240                1245
```

Thr Ser Pro Ile Asn Pro Ala Val Ala Leu Glu
    1250             1255

<210> SEQ ID NO 6
<211> LENGTH: 16
<212> TYPE: PRT
<213> ORGANISM: artificial sequence
<220> FEATURE:
<223> OTHER INFORMATION: synthetic protein

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 5
<212> TYPE: PRT
<213> ORGANISM: artificial sequence
<220> FEATURE:
<223> OTHER INFORMATION: synthetic protein

<400> SEQUENCE: 7

Tyr Arg Ser Leu Glu
1               5

<210> SEQ ID NO 8
<211> LENGTH: 5
<212> TYPE: PRT
<213> ORGANISM: artificial sequence
<220> FEATURE:
<223> OTHER INFORMATION: synthetic protein

<400> SEQUENCE: 8

Phe Ile Gly Gln Tyr
1               5

<210> SEQ ID NO 9
<211> LENGTH: 10
<212> TYPE: PRT
<213> ORGANISM: artificial sequence
<220> FEATURE:
<223> OTHER INFORMATION: synthetic protein

<400> SEQUENCE: 9

Glu Gln Lys Leu Ile Ser Glu Glu Asp Leu
1               5                   10

<210> SEQ ID NO 10
<211> LENGTH: 18
<212> TYPE: PRT
<213> ORGANISM: artificial sequence
<220> FEATURE:
<223> OTHER INFORMATION: synthetic protein

<400> SEQUENCE: 10

Ile Pro Asp Glu Gln Lys Leu Ile Ser Glu Glu Asp Leu Tyr Lys Gly
1               5                   10                  15

His His

<210> SEQ ID NO 11
<211> LENGTH: 34
<212> TYPE: DNA
<213> ORGANISM: primer

<400> SEQUENCE: 11
attacccggg ctagctatgg tcgtgatgct gcgg                              34

```
<210> SEQ ID NO 12
<211> LENGTH: 45
<212> TYPE: DNA
<213> ORGANISM: primer

<400> SEQUENCE: 12
tagatcctct tcacttatta acttctgttc atcaggaatc tgtat            45

<210> SEQ ID NO 13
<211> LENGTH: 45
<212> TYPE: DNA
<213> ORGANISM: primer

<400> SEQUENCE: 13
cagaagttaa taagtgaaga ggatctatat aaaggacacc atgta            45

<210> SEQ ID NO 14
<211> LENGTH: 24
<212> TYPE: DNA
<213> ORGANISM: primer

<400> SEQUENCE: 14
cttccacagt gacatagtag gcat                                   24

<210> SEQ ID NO 15
<211> LENGTH: 33
<212> TYPE: DNA
<213> ORGANISM: primer

<400> SEQUENCE: 15
ggctctttca tcggtcaatt cagtggcaaa aaa                         33

<210> SEQ ID NO 16
<211> LENGTH: 33
<212> TYPE: DNA
<213> ORGANISM: primer

<400> SEQUENCE: 16 tttttttgcca ctgaattgac cgatgaaaga gcc                        33

<210> SEQ ID NO 17
<211> LENGTH: 33
<212> TYPE: DNA
<213> ORGANISM: primer

<400> SEQUENCE: 17
ggctctttca tcggtcaaca cagtggcaaa aaa                         33

<210> SEQ ID NO 18
<211> LENGTH: 33
<212> TYPE: DNA
<213> ORGANISM: primer

<400> SEQUENCE: 18 tttttttgcca ctgtgttgac cgatgaaaga gcc                        33

<210> SEQ ID NO 19
<211> LENGTH: 33
<212> TYPE: DNA
<213> ORGANISM: primer

<400> SEQUENCE: 19
```

```
ttcatcaaac gcagttaggg tggcaaatac tca                                33
```

<210> SEQ ID NO 20
<211> LENGTH: 33
<212> TYPE: DNA
<213> ORGANISM: primer

<400> SEQUENCE: 20

```
ctgagtattt gccaccctaa ctgcgtttga tga                                33
```

<210> SEQ ID NO 21
<211> LENGTH: 32
<212> TYPE: DNA
<213> ORGANISM: primer

<400> SEQUENCE: 21

```
ccgcggaagc ttgaggtaca ggcctttaat gg                                 32
```

<210> SEQ ID NO 22
<211> LENGTH: 30
<212> TYPE: DNA
<213> ORGANISM: primer

<400> SEQUENCE: 22

```
gggcccaagc ttttctaggg ctactgcagg                                    30
```

<210> SEQ ID NO 23
<211> LENGTH: 28
<212> TYPE: PRT
<213> ORGANISM: artificial sequence
<220> FEATURE:
<223> OTHER INFORMATION: synthetic protein

<400> SEQUENCE: 23

```
Arg Gln Ile Lys Ile Trp Phe Gln Asn Arg Arg Met Lys Trp Lys Lys
1               5                   10                  15
Phe Gln Gly Ile Phe Ser Gly Asp Glu Asn Phe Gln
            20                  25
```

<210> SEQ ID NO 24
<211> LENGTH: 17
<212> TYPE: PRT
<213> ORGANISM: artificial sequence
<220> FEATURE:
<223> OTHER INFORMATION: synthetic protein

<400> SEQUENCE: 24

```
Arg Gln Ile Lys Ile Trp Phe Gln Asn Arg Arg Met Lys Trp Lys Lys
1               5                   10                  15
Ser
```

<210> SEQ ID NO 25
<211> LENGTH: 13
<212> TYPE: PRT
<213> ORGANISM: artificial sequence
<220> FEATURE:
<223> OTHER INFORMATION: synthetic protein

<400> SEQUENCE: 25

```
Ser Gln Phe Asn Glu Asp Gly Ser Phe Ile Gly Gln Phe
1               5                   10
```

<210> SEQ ID NO 26
<211> LENGTH: 13

```
<212> TYPE: PRT
<213> ORGANISM: artificial sequence
<220> FEATURE:
<223> OTHER INFORMATION: synthetic protein

<400> SEQUENCE: 26

Gln Phe Asn Glu Asp Gly Ser Phe Ile Gly Gln Phe Ser
1               5                   10

<210> SEQ ID NO 27
<211> LENGTH: 17
<212> TYPE: PRT
<213> ORGANISM: artificial sequence
<220> FEATURE:
<223> OTHER INFORMATION: synthetic protein

<400> SEQUENCE: 27

Ser Arg Gln Ile Lys Ile Trp Phe Gln Asn Arg Arg Met Lys Trp Lys
1               5                   10                  15

Lys
```